United States Patent [19]

Gozani et al.

[11] Patent Number: 5,078,952
[45] Date of Patent: Jan. 7, 1992

[54] MULTI-SENSOR EXPLOSIVE DETECTION SYSTEM

[75] Inventors: Tsahi Gozani, Palo Alto; Patrick M. Shea, Sunnyvale; Z. Peter Sawa, Oakland, all of Calif.

[73] Assignee: Science Applications International Corporation, San Diego, Calif.

[21] Appl. No.: 463,036

[22] Filed: Jan. 10, 1990

Related U.S. Application Data

[63] Continuation-in-part of Ser. No. 367,534, Jun. 16, 1989, abandoned, which is a continuation-in-part of Ser. No. 321,511, Mar. 9, 1989, Pat. No. 5,006,299, which is a continuation of Ser. No. 53,950, May 26, 1987, abandoned.

[51] Int. Cl.$^5$ .............................................. G21G 1/06
[52] U.S. Cl. .................................. 376/159; 376/158; 376/161; 364/22; 364/933
[58] Field of Search .................. 376/159, 161, 158; 382/16, 17; 364/513

[56] References Cited

U.S. PATENT DOCUMENTS 3,808,444  4/1974  Schneeberger et al. ............ 250/492
4,851,687  7/1989  Ettinger et al. .................. 250/390.04
4,882,121 11/1989  Grenier ............................ 376/159

OTHER PUBLICATIONS

Detection of Explosives in Checked Airline Baggage Using an Artificial Neural System, by Patrick M. Shea et al. IJCNN Jun. 1989, pp. 11-31-11-34.
Gozani et al., "Nuclear-Based Techniques", *Journal of Energetic Materials*, vol. 4:377–414, (1986).

*Primary Examiner*—Donald P. Walsh
*Assistant Examiner*—Meena Chelliah

*Attorney, Agent, or Firm*—Fitch, Even, Tabin & Flannery

[57] ABSTRACT

A nuclear detection system and method efficiently detects explosives in checked airline baggage or other parcels with a high probability of detection (PD) and a low probability of false alarms (PFA). The detection system detects the presence of nitrogen and its rough density distribution within the object under investigation by performing a nuclear-based analysis of the object. The detection system includes a source of thermal neutrons; an array of gamma ray detectors; a neutron detector; means for irradiating the object being examined to neutrons from the neutron source, which neutrons interact with the atomic nuclei of one or more specific elements, e.g., nitrogen, chlorine, or hydrogen present within the object so as to cause elemental-specific gamma rays to be emitted; means for capturing and counting the elemental-specific gamma rays and determining their approximate origin within the object, thereby providing a rough measure of the density distribution of these specific elements within the object; and means for detecting neutrons that pass through the object without substantially interacting with atomic nuclei, thereby providing an image of the atomic density distribution of the object similar to conventional neutron radiography. One embodiment of the invention includes an artificial neural system (ANS) of analyzing the recorded gamma rays and efficiently discriminating between objects carrying explosives and objects not carrying explosives. Another embodiment utilizes a spectral correlation method (SCM) to remove undesirable background noise from the spectrum of detected gamma rays. Still another embodiment uses a X-ray system to generate an electron density image of the object being investigated, which electron density image helps confirm the presence of explosives within the object.

25 Claims, 6 Drawing Sheets

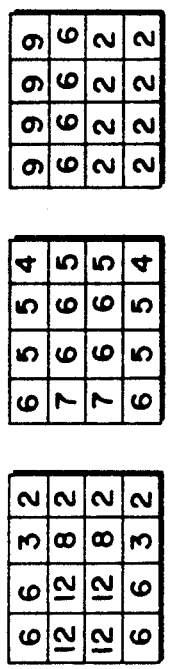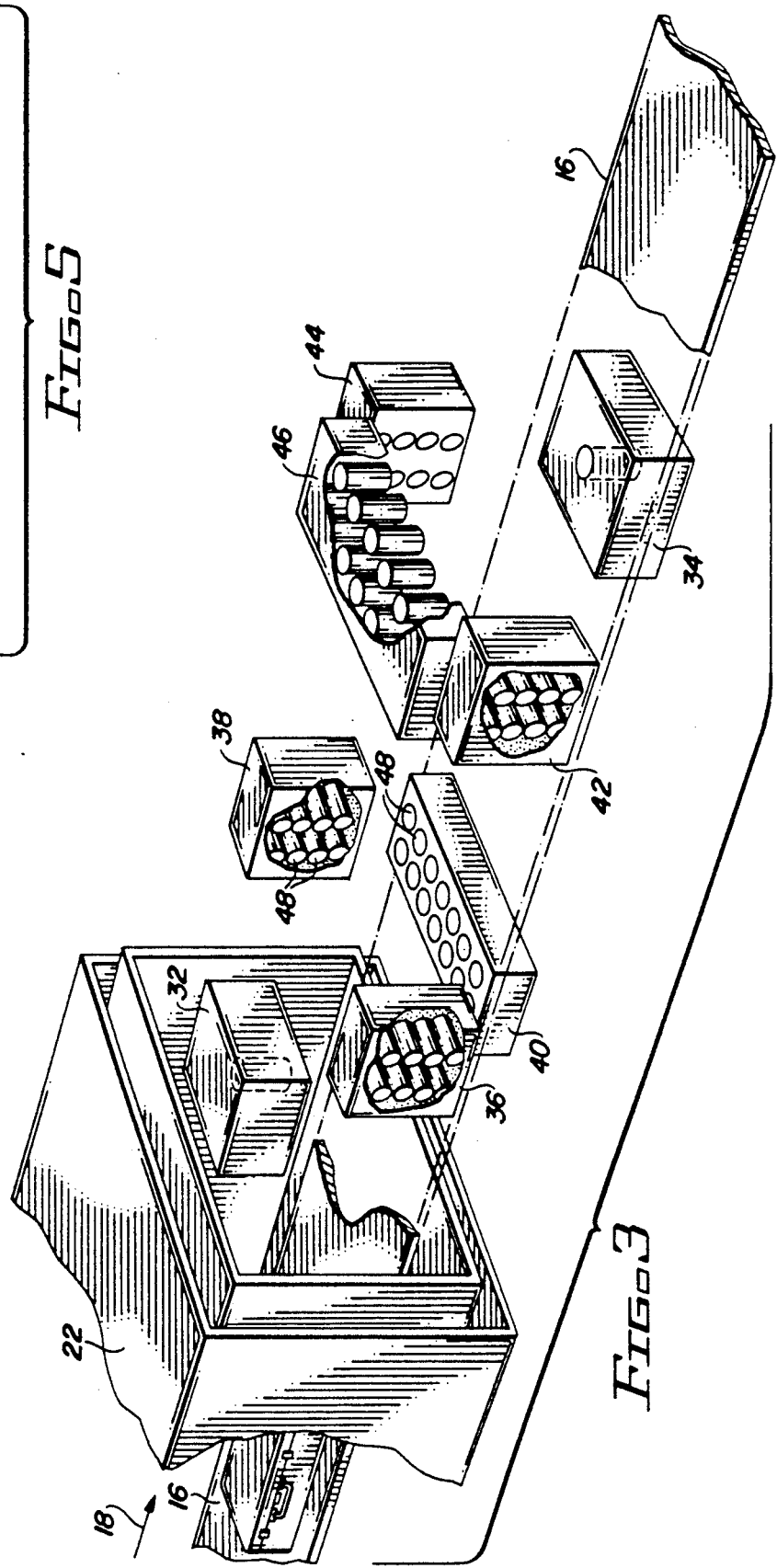
FIG. 5
FIG. 3

MULTI-SENSOR EXPLOSIVE DETECTION SYSTEM

This invention was made with Government support under one or more contracts awarded by the Federal Aviation Administration (FAA), including FAA Contract DTFA03-85-C-00053. The Government has certain rights in this invention.

RELATED APPLICATIONS

This application is a continuation-in-part of application Ser. No. 07/367,534, filed Jun. 16, 1989 now abandoned, which is a continuation-in-part of application Ser. No. 07/321,511, filed Mar. 9, 1989, which is a continuation of application Ser. No. 07/053,950, filed May 26, 1987 now abandoned, which applications are incorporated herein by reference. Application Ser. No. 07/321,511 is now U.S. Pat. No. 5,006,299.

BACKGROUND OF THE INVENTION

The present invention relates to an explosive detection system used to detect explosives in checked airline baggage. More specifically, the present invention relates to a nuclear-based explosive detection system that accurately discriminates between parcels with and without explosives. The system includes, in addition to a neutron source and an array of gamma ray detectors, a neutron detector, means for removing background noise from the ensuing gamma ray spectrum, an X-ray system, and/or an artificial neural system (ANS).

A great need exists for the scanning of luggage, baggage and other parcels for the detection of any explosive material contained or concealed within their confines. For example, a large number of pieces of luggage (estimated at over 2,000,000) are checked and/or carried onto aircraft daily by close to seven hundred and fifty thousand (750,000) passengers within six hundred (600) airports extending across the country. Many more packages move through the mails or are shipped to sensitive buildings. There is a possibility, albeit small, that any one piece of luggage or parcel might contain explosive material. It is, therefore, desirable to protect the public by providing detection systems to scan the luggage and parcels to detect the presence of any explosive material.

It thereby follows that any system of checking luggage or parcels must have a very high probability of detection (PD) in order to be effective. Because of the large number of parcels processed, a high throughput is necessary for practicality. In addition, any detection system, because of the large number of scanned items, is bound to occasionally give a false alarm. The probability of these false alarms (PFA) must be minimized in order to provide for an effective explosive detection system. This is because when an alarm occurs it is not known, at that time, whether it is true or false. This means that each time an alarm occurs, a passenger or parcel must be detained for further investigation. If false alarms are significantly high the nuisance level and the delays could be unacceptable to the public. It is, therefore, important that any explosive detection system must have a very high probability of detection (high PD), a high throughput rate, and yet at the same time have a very low probability of false alarms (low PFA). These conflicting criteria have hampered efforts in the past to build a reliable and usable system.

In general, prior art systems have not met the desired characteristics of having a high probability of detection (PD) with a low probability of false alarms (PFA) at acceptable throughput rates. As an example, one such prior art system is shown in U.S. Pat. No. 3,832,545. This patent provides for a system for the detection of nitrogen, which is generally present in the explosive materials to be detected. As described in the referenced patent, a rough two-dimensional profile of the nitrogen content within the object being inspected is provided. This profile is then used in an attempt to determine whether explosive materials are present. Unfortunately, however, because of the types of detectors used by the invention described in the '545 patent (liquid or plastic scintillators), the processing of the detector signals is quite slow and cumbersome, thereby limiting the throughput rate. Moreover, the two-dimensional limitation allows many materials to be positioned in the object being examined so as to defy detection, thereby providing an unacceptably low PD.

Other types of prior art explosive detection systems depend upon the prior seeding of explosive materials with a tracer material, such as a radioactive tracer. Although this type of system could be very useful if all explosive material were manufactured with such tracer material, because of the large amount of explosive material which has already been manufactured and because of the difficulty of controlling the manufacture of all explosive material so as to contain such tracer material, this type of system is not practical. A useable system must be able to detect the presence of explosive material of a conventional type and of an unconventional type, whether disposed within an object either in its original manufactured form, or if deployed within the object so as to attempt to confuse or evade the detection system. The prior art systems have not met these various criteria and cannot produce the desired high probability of detection with the relatively low production of false alarms.

An acceptable response to the explosive threat to aviation, mails, or shipping requires detection techniques that are highly sensitive, specific, rapid and non-intrusive. The efficient detection of nitrogen, at this point, offers the best overall solution, although other elements could also be detected. It is, therefore, important that the detection of nitrogen be provided to give the maximum information of the physical parameters of the explosive, such as density and spatial distribution. The use of nuclear based techniques which subject the luggage or parcels to thermal neutrons can be the basis of a system to produce the desired results, but this system cannot be based on the prior art techniques. It is important that the intensity, energy and spatial distribution of the detected radiations from the object under observation be provided in a way to help determine the presence or absence of explosives, and this has not yet been accomplished.

In addition to high detection sensitivity and low false alarm, the detection of the explosive should be independent of the specific configuration and must be non-intrusive in order to protect privacy. The detection equipment, of course, must be non-hazardous to the contents of the checked items and to the operating personnel and environment. Other more general criteria are that the system must be reliable, easily maintained and operable by relatively unskilled personnel and that the cost must be low enough so as to be non-burdensome to airlines and airports. Finally, it is desirable, when all other requirements are achieved, that the size of the system be relatively small so that the system may be useful in a wide variety of environments.

In addition to the nuclear based systems described above, non-nuclear systems have also been investigated. These systems have occasionally achieved relatively high efficiencies of detection for some types of explosives, but generally have relatively high false alarm rates and have long screening times. These type of non-nuclear systems, therefore, by themselves cannot achieve the desired results. However, some features of such non-nuclear systems may advantageously be combined with a nuclear system as described herein, to significantly improve the overall detection capabilities of the system.

In order to develop a proper explosive detection system, an understanding is required of the properties of the various explosives relevant to the specific techniques to be used. Although there are a large number of explosive types, a general classification into six major groups with minor variations, has been proposed. The proposed classification scheme includes the following types of explosives: (1) nitroglycerine based dynamites, (2) ammonium nitrate based dynamites, (3) military explosives, (4) homemade explosives, (5) low order powders, and (6) special purpose explosives.

In general, all of these explosive types contain a relatively high amount of nitrogen ranging from nine to thirty five percent by weight. The nominal density of these explosives is typically 1.6 g/cm$^3$, with ranges between 1.25 to 2 g/cm$^3$ or more. These physical properties demonstrate that the most unique signature of explosives is the high concentration and density of the nitrogen content. Also the presence of other elements in combination with the presence of nitrogen can be considered. Physical factors may also help identify explosives. One physical factor, for example, is a minimum propagation thickness or diameter in order for most explosives to be effective. This minimum propagation thickness requires a sizeable contiguous body of explosives in the other two dimensions. This information is useful to the detection of explosives without making a specific assumption of the actual shape of the explosive.

It can be seen, therefore, that a nuclear detection technique can provide for the detection of the nitrogen content, which nitrogen content can provide some indication as to the presence of an explosive. However, the frequent occurrence of nitrogen in non-explosive materials limits the level of detection sensitivity and merely detecting the presence of absence of nitrogen alone is generally not sufficient. Therefore, additional information is required beyond simply sensing the presence of the nitrogen. The present invention provides for this additional information.

SUMMARY OF THE PRESENT INVENTION

The present invention provides a nuclear-based detection system and method that efficiently detects explosives in checked airline baggage or other parcels with a high probability of detection (PD) and a low probability of false alarms (PFA). The detection system advantageously combines several detection criteria to improve the speed and performance with which the detection system is able to discriminate between objects (parcels, suitcases, packages, etc.) with explosives and objects without explosives.

The first and foremost criteria used by the present invention to detect explosives is to ascertain a high content and concentration of nitrogen in the object under examination. The content and concentration of other elements in combination with nitrogen is also selectively used. To this end, the present invention uses thermal neutron activation (TNA) to immerse the object in a bath of thermal neutrons, which neutrons interact with the atomic nuclei causing prompt gamma rays to be emitted. If nitrogen is present, the gamma rays have a unique energy (10.8 MeV). If other prescribed elements are present, the gamma rays have other known energies. The presence of such nitrogen-specific (or other element-specific) gamma rays thus comprises one "signature" of an explosive. A main function of the present invention is thus to detect such nitrogen-specific (or other element-specific) gamma rays.

In order to achieve the highest possible sensitivity to nitrogen, the detection scheme employed by the invention provides the highest possible count-rate of gamma rays due to nitrogen with as low a background (of gamma rays not due to nitrogen) as possible. This is accomplished by utilizing a properly designed detector array that surrounds the object under examination as it is submersed in the thermal neutron bath, and appropriate signal processing techniques to perform the gamma ray counts. The 10.8 Mev gamma ray count-rate from each detector within the array is then combined with a suitable reconstruction algorithm to yield a rough two or three-dimensional image of the nitrogen bearing material within the object. This rough image helps identify explosives because it provides a course measure of the nitrogen density. (This density measure is inherently course due to the practical sizes of the gamma detectors and the large detectors.) The invention described in applicant's first application, Ser. No. 07/053,950, of which this application is a continuation-in-part, was the first known disclosure of a TNA based system that advantageously provided both a high nitrogen count rate and coarse three-dimensional imaging capabilities.

To improve upon the invention described in applicants' first patent application, the present invention, in accordance with one embodiment thereof, enhances the spatial resolution of the nitrogen image (and thus improves the measurement of nitrogen density) by correlating the low resolution gamma ray imaging with a high-resolution two-dimensional density image obtained using X-ray radiography. This technique enhances the detection of explosives because explosives are generally high in physical density as well as nitrogen content. Advantageously, the resolution and precision obtained using such well accepted and tested X-ray systems is far beyond that which neutron based systems can provide. Thus, by correlating the coarse (but very nitrogen specific) image obtained from the gamma ray detector with the high spatial resolution (but non-nitrogen specific) image delivered by the X-radiography system, a much more meaningful image of dense nitrogen-bearing materials in the object under examination is obtained.

The combination of gamma and X-ray imaging advantageously provides enhanced features that neither alone can provide. For example, if an X-ray image of an object under examination indicates the presence of an item that could be an explosive during an on-line operation, the combined image of the object may be presented to the operating personnel responsible for detecting such explosives. The gamma ray image can then be used to "color" the X-ray image so that the explosive can be readily picked out from other items seen in the X-ray image. The form of the explosive can also be determined with sufficient accuracy, thus allowing explosives to be shipped, e.g., as ammunition, if declared, in order to confirm that only explosives in the proper form are present.

Another embodiment of the improved explosive detection system of the present invention includes the use of a neutron detector. The neutron detector advantageously allows neutron flux to be measured, which neutron flux provides yet another means for obtaining density information concerning the contents of the object being examined. That is, by counting the number of neutrons that are able to pass through the object without interacting with atomic nuclei, similar to that which is done in conventional neutron radiography, another measure of the density of the elements within the object is obtained. This additional information further improves the imaging resolution capabilities of the system.

Yet a further embodiment of the present invention includes means for improving the manner in which the gamma ray count signals are processed, and more particularly the manner in which background noise (gamma ray counts due to non-nitrogen elements) is removed from the measured gamma ray spectra. In accordance with this technique, background noise at one point of the gamma ray spectrum is measured, appropriately weighted, and subtracted from the gamma ray spectrum at the point of interest, e.g., 10.8 MeV, in order to remove background noise from the point of interest. This technique of background subtraction is referred to hereafter as the "spectral correlation method" (SCM).

A still further embodiment of the present invention includes the use of an artificial neural system (ANS), a form of a parallel distributed processing technique in order to improve the speed and performance with which the detection system is able to distinguish objects with explosives from objects without explosives.

The present invention may thus be summarized as a TNA-based explosive detection system that includes various combinations of the following improvements: (1) an X-ray system; (2) a neutron detector; (3) means for using a SCM, or an equivalent technique, to remove background noise from the gamma ray spectra; and/or (4) an ANS to improve the speed and accuracy with which the decision concerning the presence of explosives is made.

In operation, the present invention functions as follows: neutrons from a neutron source are directed to the object under examination. The neutrons are of a high enough energy to easily penetrate into the object being examined, e.g., through the walls or sides of the parcels or luggage. These neutrons are absorbed by or interact with the atomic nuclei of the elements that make up the materials carried within the object being examined. Different elements emit gamma rays at different characteristic energy levels after such neutron absorption or interaction (much like fluorescence). For example, gamma rays emitted from nitrogen have a different characteristic energy level than do gamma rays emitted from oxygen or carbon for the same neutron exposure. The emitted gamma rays have a high enough energy so that they also easily penetrate through the walls of the object being examined. A suitable detector array is positioned to effectively surround the object as it is examined. This detector array catches or captures the emitted gamma rays and records the number of gamma-rays (i.e., counts the gamma rays) observed at a selected characteristic energy (for example 10.8 MeV, corresponding to nitrogen.) The number of gamma rays of a particular characteristic energy (the gamma ray count) detected by a particular detector depends upon the amount of the element present within the material being examined, the location of the element within the parcel under investigation, the number of neutrons present (the neutron concentration), and the probability that the element will capture a neutron and emit that gamma ray. Because the number of neutrons present is known (or can be measured, which measurement is facilitated by use of the neutron detector), and the probability that the element will capture a neutron and emit a gamma ray is a known constant for any particular element, an analysis of the recorded gamma rays of the selected energy, as well as the neutron flux as measured by the neutron detector, thus provides sufficient information to determine the amount of each element and its location within the material being examined. This determination, in turn, leads to an indication as to whether an explosive material is present within the object under examination.

Advantageously, an even more accurate count of the gamma rays emitted from nitrogen (i.e., gamma rays at 10.8 MeV) is made possible in accordance with the present invention by effectively removing the background noise from the gamma ray spectra at 10.8 MeV using the spectral correlation method (SCM) described herein.

The determination of whether an explosive material is present within the object may also be greatly facilitated, further in accordance with the teachings of the present invention, with the probability of detection (PD) being increased, while maintaining the probability of false alarm (PFA) at acceptably low levels, through the use of the ANS system. The ANS system efficiently processes in parallel the recorded data from all of the numerous detectors within the detector array. Further, the ANS system, unlike conventional statistical discriminate analysis (which may also be used to make the explosive/non-explosive decision), does not require complex and labor-intensive calibration procedures. Rather, by using an ANS, the detection system learns to detect explosive materials by simply being presented with representative examples of objects containing explosive materials. Such a system is not only brought up to speed much quicker than prior detection systems, but is also more adaptable to changing circumstances. For example, the system can in theory be used to detect materials other than explosive materials, e.g., contraband.

The present invention includes, in one embodiment, a specific arrangement and type of detectors, positioned relative a source of thermal neutrons, to detect or count the number of gamma rays so as to provide the proper information needed to ascertain the presence and density distribution of nitrogen. The information may then be readily analyzed by the detection system to indicate the possible presence of an explosive threat. A high count rate of detected gamma rays of a particular energy, for example, immediately indicates the presence of a great deal of nitrogen. The ANS can then quickly determine with a high PD whether the presence of the nitrogen indicates the presence of an explosive material, or whether it indicates the presence of some other benign nitrogen-rich material. Advantageously, with the ANS, the system of the present invention is also capable of detecting explosives in unconventional configurations while maintaining the number of false alarms to a relatively low level. The prior art detector systems, in contrast, while providing for the gross detection of explosives, cannot provide for the more sensitive detection of the unconventional explosive configurations concurrent with a relatively low level of false alarms.

A preferred embodiment of the explosive detection system of the present invention includes the use of efficient inorganic scintillators capable of resolving closely spaced high energy gamma ray lines. Specifically, sodium iodide scintillators are used to provide for detection. It is to be appreciated, however, that other inorganic scintillators such as cesium iodide, bismuth germinate and barium fluoride scintillators may also be used. In addition, inorganic solid state detectors such as lithium-drifted germanium, high purity germanium or mercuric iodide may be used.

The inorganic scintillators of the present invention are arranged to form at least one ring of detectors so as to provide for a detection of a plurality of slices or parallel successive planes of the object under inspection as the object is moved continuously through the ring of detectors. In a specific embodiment of the invention, this ring is broken into sets of C-rings; and in order to provide for a better three dimensional representation, two spaced sets of C-ring detectors may be used with the open ends of the C-rings facing each other so as to provide for a detection completely around the object and with the plurality of successive planes building up a three dimensional profile of the object under inspection. These rings need not all be in the same plane, nor must they be shaped similarly.

The detectors included in the detector arrays of the present invention may include one or more neutron detectors. Such neutron detector(s) are typically separate and may be apart from the C-ring array of gamma ray detectors. Each detector is coupled to appropriate processing circuitry. This processing circuitry may include an artificial neural system (ANS). The ANS allows the signals from each detector to be processed in a parallel distributed processing scheme that provides for a very rapid, yet accurate analysis of the complete data set. In effect, the ANS learns and merges features in the detector observations and automatically generates classification criteria. The ANS has the ability to learn patterns and classify objects based on these patterns. This learning ability is advantageously inherent in the ANS and does not require programming or algorithmic development. The ANS needs only examples from which to learn.

The system of the present invention is further capable of scanning a continuous flow of objects, such as luggage and parcels carried on a conveyor belt. In addition, the operation of the system may be fully automatic so that the system does not depend on operator experience or interpretation, thereby providing for the automatic detection of explosives.

It is a feature of the present invention to provide an explosive detection system that can continuously examine objects for explosive materials at an acceptably high throughput rate, e.g., not slower than approximately one object every six seconds.

It is another feature of the invention to provide such a detection system that does not damage film or magnetic recording media.

A further feature of the invention is to provide a detection system that exhibits a high PD at an acceptably low PFA, and that provides an alarm signal indicating the probable presence of an explosive in a particular object prior to the time the object exits the system.

It is yet another feature of the invention to provide an explosive detection system wherein complex and labor-intensive calibration procedures can be minimized, thereby allowing the system to be quickly installed and easily operated.

Still another feature of the invention provides a nitrogen image of the object under investigation. In one embodiment, the spatial resolution of this nitrogen image may be significantly enhanced through the use of X-ray radiography.

A further feature of the invention allows background noise at a specific point in the gamma ray spectrum to be removed, thereby greatly improving the sensitivity of the system to detecting gamma rays at that specific point.

It is another feature of the invention that additional elements, e.g., hydrogen, chlorine, may be identified within the object under investigation, and from that identification improved discrimination of contraband, e.g. explosives or drugs, can be obtained.

Another feature of the invention allows the detection system to learn patterns from examples and classify objects based on these learned patterns, without the need for programming or algorithmic development.

It is still a further feature of the invention to provide a detection system that is readily adaptable to detect a wide variety of different types of explosive or other materials, and/or to quickly correct itself in the event of misclassifying a particular object.

BRIEF DESCRIPTION OF THE DRAWINGS

The above and other features and advantages of the present invention will be more apparent from the following description, drawings and appendices wherein:

FIG. 3 illustrates one possible arrangement of a conveyer path for the system showing the positioning of a pair of thermal neutron sources and sets of inorganic scintillator detectors comprising a C-ring detector array;

FIGS. 5(a), (b) and (c) illustrate typical spatial profiles of nitrogen concentration for explosive and non-explosive materials;

Appendix A contains a description of the manner in which an electron density image obtained from a conventional X-ray system is correlated with the nitrogen density image obtained from the gamma ray detectors in order to detect explosives;

Appendix B describes the background subtraction technique used by one embodiment of the invention in order to improve the sensitivity of the system to detecting and counting 10.8 MeV gamma rays; and Appendix C provides representative test data of one particular embodiment of the present invention wherein Californium is used as the neutron source

DESCRIPTION OF THE PREFERRED EMBODIMENT

The following description is of the best mode presently contemplated of carrying out the invention. This description is not to be taken in a limiting sense, but is made merely for the purpose of describing the general principles of the invention. The scope of the invention should be determined with reference to the appended claims.

Figure 1:
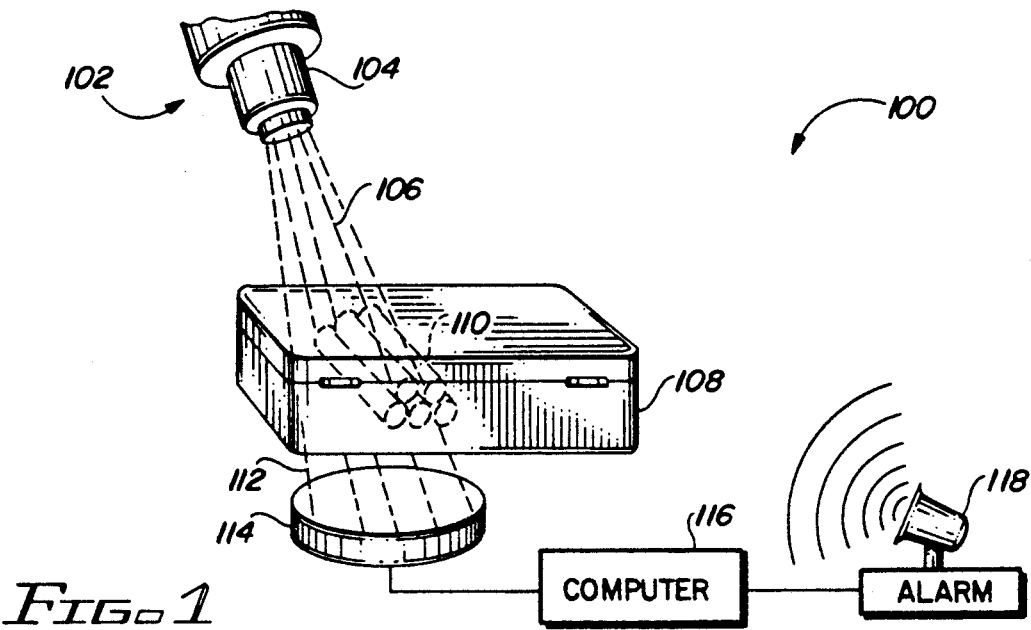
FIG. 1 is a simplified schematic diagram of a nuclear-based explosive detection system.

Referring first to FIG. 1, a simplified schematic diagram of a nuclear-based explosive detection system 100 is illustrated. The system includes a radioactive source 102 that emits thermal neutrons 106. The thermal neutron source 102 may include a nozzle 104, or equivalent structure, that directs the neutrons 106 towards the object under examination, such as luggage 108, so as to irradiate or immerse the luggage and its contents with neutrons. Nitrogen contained within an explosive material 110, placed inside of the luggage 108, interacts with the probing neutron radiation and emits prompt gamma rays 112 of a particular energy level. Non-explosive materials within the luggage may have other elements that also interact with the probing neutron radiation, but the gamma rays emitted from such other elements have a different energy than do those from nitrogen. The number and energy of the gamma rays are measured in detector 114, which detector generates an appropriate output signal for each gamma ray of a particular energy that is received. A computer 116 monitors the output of the detector 114 and, after appropriate signal processing, makes a determination as to whether explosive material is present within the luggage. If so, an alarm 118 sounds, or is otherwise generated (e.g., visually) which alarm alerts operating personnel that explosive material 110 may be present within the luggage 108 so that appropriate action may be taken. Such action may include, for example, automatically diverting the suspect luggage away from the other luggage so that an extensive manual or other search of the luggage and its contents can be made.

Figure 2A:
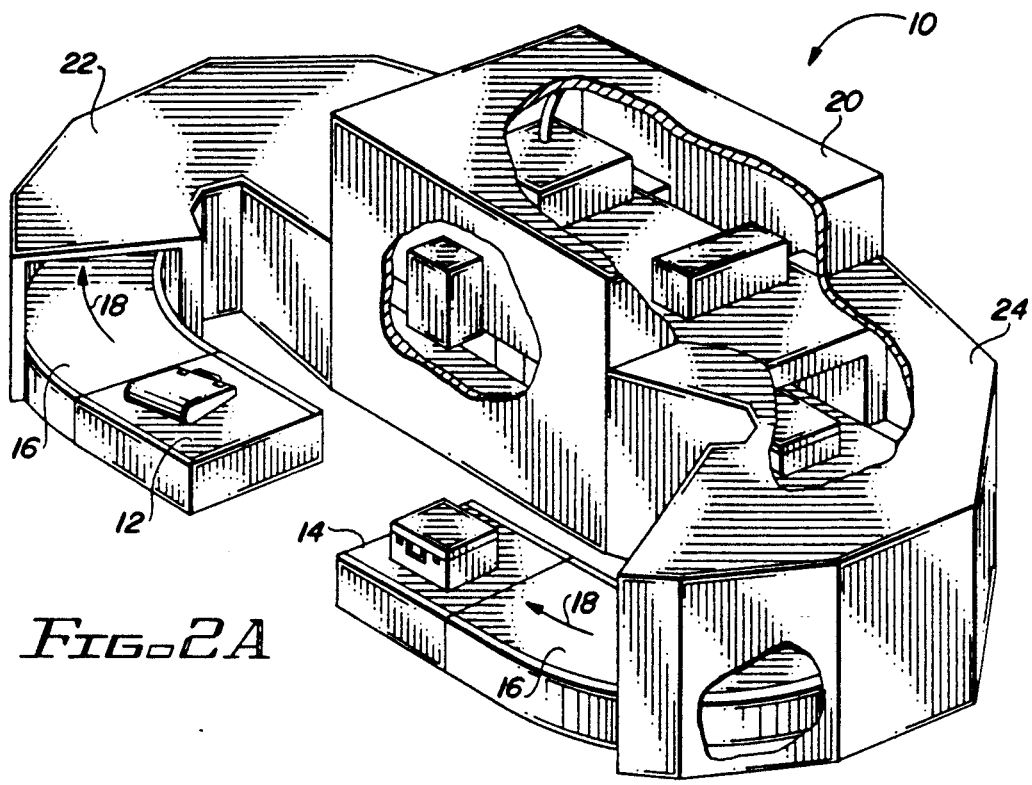
FIG. 2A illustrates a perspective view of one embodiment of a luggage and parcel inspection system.

As shown in FIG. 2A, one type of an explosive detection system 10 in accordance with the present invention includes a loading station 12 (which may consist of a scale to weigh the luggage) and an unloading station 14 (which may consist of a diverter to separate the alarmed luggage from the rest). The loading station leads to a continuous conveyer belt 16 which extends from the loading station 12 to the loading station 16 and has a continuous motion as indicated by the arrows 18. A central shield structure 20 encloses the explosive detection system and with two external wing portions 22 and 24 extending from the central structure 20 to enclose the conveyer belt 16 leading from and to the loading and unloading stations 12 and 14.

Figure 2B:
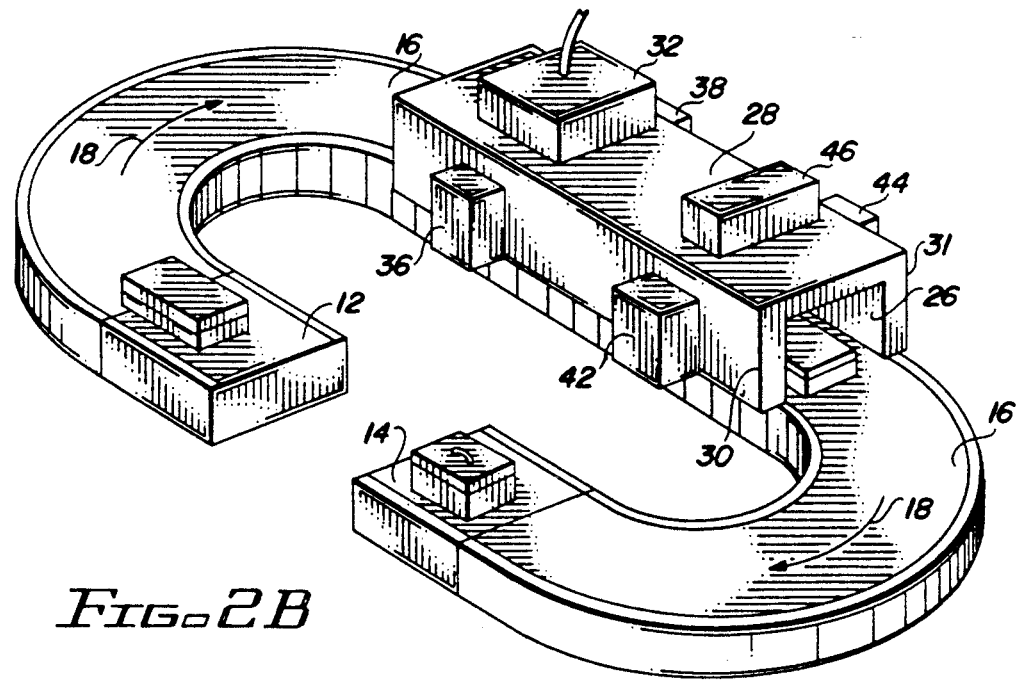
FIG. 2B illustrates the system of FIG. 1 with a shield portion of the system removed.

As can be seen in FIG. 2B, wherein the shields 20, 22 and 24 are removed, the explosive detection system is positioned over a central portion of the conveyer belt 16. Specifically, the explosive detection system includes a cavity structure 26 through which the conveyer belt 16 passes. As shown in FIGS. 2A and 2B, various articles of luggage and parcels may be positioned on the loading station 12 and may then be carried thorough the cavity 26 to the unloading station 14 by the conveyer belt 16.

The cavity is formed by external wall members including a top wall 28, side walls 30 and 31 and a bottom wall (not shown) which is positioned below the conveyer belt 16. Extending through the wall members are thermal neutron sources, such as source 32 positioned at the top of the cavity, and as shown in FIG. 3, neutron source 34 spaced from the neutron source 32 and positioned at the bottom of the cavity. Also as shown in FIGS. 2 and 3, detector structures are positioned to form two C-rings of detectors having their opened ends facing the neutron sources. This may be seen in FIG. 3 wherein the side detector structures 36 and 38 together with the bottom detector structure 40 are all associated with the neutron source 32. Similarly, side detector structures 42 and 44 together with the top detector structure 46 are all associated with the neutron source 34.

As shown in FIG. 3, the side detector structures may be provided by two sets of four detectors located in each side detector structure 36 and 38. The bottom detector structure 40 includes two sets of seven detectors. The detectors associated with the neutron source 34 similarly include two sets of four detectors located in each side detector structure 42 and 44 and with two sets of seven detectors located in the top detective structure 46. The detectors associated with the neutron source 32, therefore, form a C-ring of detectors having the opened portion of the C facing upward. In an opposite fashion the detectors associated with the neutron source 34 form a C-ring with the opened portion of the C facing downward. The combination of the two sets of C-ring detectors thereby provide for the detection of a complete ring around the object under inspection to produce a better three dimensional profile of the nitrogen distribution within any particular object passing through both sets of detectors.

While the invention is described with reference to the use of two C-ring detector structures and with each C-ring including two sets of parallel rows and columns of detectors, it should be appreciated that only a single C-ring structure may be used with only a single row and column of detectors. The use of the additional parallel sets of detectors improves a visualization of the profile of the concentration of nitrogen, but a simpler system could be used with a single C-ring and single rows and columns of detectors. It is also to be appreciated that more or less detectors could be used. A full or partial ring of detectors could also be placed out of the plane of the source, around the cavity.

The actual structure of the neutron source and its environment, such as the structures 32 and 34, may be of any type. For example, the neutron source may be a radioisotope (such as $^{252}$Cf) or an electronic neutron source (such as (D,D) or (D,T) generators). By collisions, mostly with the nuclei of the selected materials surrounding the source the neutrons are slowed down to create a cloud of low energy thermal neutrons within the cavity. The low energy thermal neutrons specifically interact with the variety of nuclei in the luggage or parcel. The interaction of the low energy thermal neutrons produces characteristic high energy gamma rays which are detected by the external rows and columns forming the C-ring detectors.

Each detector in the rows and columns preferably are formed of inorganic scintillators. Specifically, all of the detectors, such as represented by a detector 48, may be formed of an inorganic scintillator material, such as sodium iodide (NaI). Other inorganic materials may be used, for example, inorganic scintillator materials such as cesium iodide (CsI), bismuth germanate (BGO-$Bi_4 Ge_3 O_{12}$) or barium fluoride ($BaF_2$) Solid state detectors also may be used to provide for the detectors, such as lithium-drifted germanium (Ge(Li)), high purity germanium (HPGe) or mercuric iodide ($HGI_2$). The particular details of a specific detector structure do not form a part of the present invention, but the specific use of an inorganic scintillator with good energy resolution and efficiency to detect gamma rays produced by thermal neutrons provides for a unique detection of nitrogen and/or other elements do form a part of the present invention.

Although inorganic scintillators have been used in the past with thermal neutrons, this use was not for the detection of nitrogen in explosives, but rather to provide for the detection of chlorine, iron, chromium, etc. as a background component and not specifically for the detection of the nitrogen component and spatial distribution of the explosive material. Other uses of inorganic scintillators have been in combination with fast neutron sources so as to detect nitrogen, but this different type of neutron source provides for a different type of detection.

The present invention contemplates the combination of a thermalized neutron source with an appropriate scintillator, e.g. an inorganic scintillator, such as a sodium iodide detector. This specific combination provides for the capability of resolving closely spaced high energy gamma ray lines and specifically for detecting the particular gamma ray lines representative of the nitrogen content of explosives. These particular high energy gamma ray lines occur at 10.8 MeV. The inorganic scintillator detector is preferably used because it is a very efficient detector and because it provides acceptable features in a number of areas. These areas include level of total count rate, the shape of the detector, availability of detector, reliability and cost. It is to be appreciated that the inorganic scintillator may also be used to detect other elements representative of an explosive.

As indicated above, the currently preferred inorganic material is sodium iodide, but other inorganic materials may be used. For example, bismuth germinate has a high effective atomic number because of the bismuth and a higher density than the sodium iodide. The efficiency of a bismuth germinate scintillator is, therefore, higher than that of sodium iodide. However, bismuth germinate scintillators are inferior to sodium iodide in energy resolution and the cost for a bismuth germante scintillator is much higher than that for sodium iodide, and it also has a background component that can interfere with the nitrogen signal. However, both of these inorganic structures are superior to the organic scintillators used in the prior art devices.

The main advantage of the prior art organic scintillators, which may be plastic or liquid, is their very fast response time permitting exceedingly high count rates. Because of the very high count rates, a high background from other neutron reactions can be handled easily and thereby eliminate the need for sophisticated cavity design. Another advantage of the organic scintilators is their relatively low cost and ease of manufacture. Even with these advantages, however, the use of inorganic scintillators, and specifically in the particular C-ring configuration of the present invention, provides for a higher resolution and thereby a more efficient detection of any explosive material. The organic scintillators are inefficient detectors for high energy gamma rays and their gamma spectroscopical qualities are poor. Organic scintillators thereby have poor energy resolution and make the separation between nitrogen and deleterious signals, such as occur with Cl, Fe, Cr or Ni, very difficult.

As can be seen in FIG. 3, any item to be scanned, such as a piece of luggage, passes through the cavity on the conveyer 16 and is subjected to the thermal neutrons produced by the thermal neutron source 32. At successive positions of the piece of luggage, the individual detectors 48, forming the row 40 and columns 36 and 38, provide for a cross sectional profile of any material containing nitrogen. The C-ring of detectors thereby provides for a two dimensional slice or plane of the nitrogen concentration and with a three dimensional profile built up by the successive slices produced as the luggage moves through the C-ring of detectors.

The two dimensional plane provided by the detector structures 36, 38 and 40 has less resolution at the upper end since the C-ring is not complete. Although a detector structure could also be provided along the upper surface of the cavity such detector structure could interfere with the production of the thermal neutrons by the source 32 of such neutrons. A more efficient way of completing the ring is to have a second C-shaped group of detector structures provided downstream of the first group so that the luggage moves from the first C-ring of detector structures to the second C-ring of detector structures and with the open ends of the C-rings in the first and second sets being opposite to each other. The information from the two sets of C-rings of detector structures may be merged electronically in a computer to provide for a complete picture. As indicated above, this picture forms a three-dimensional image of the container such as the luggage and its contents by building up the successive slices or planes of information.

Figure 4:
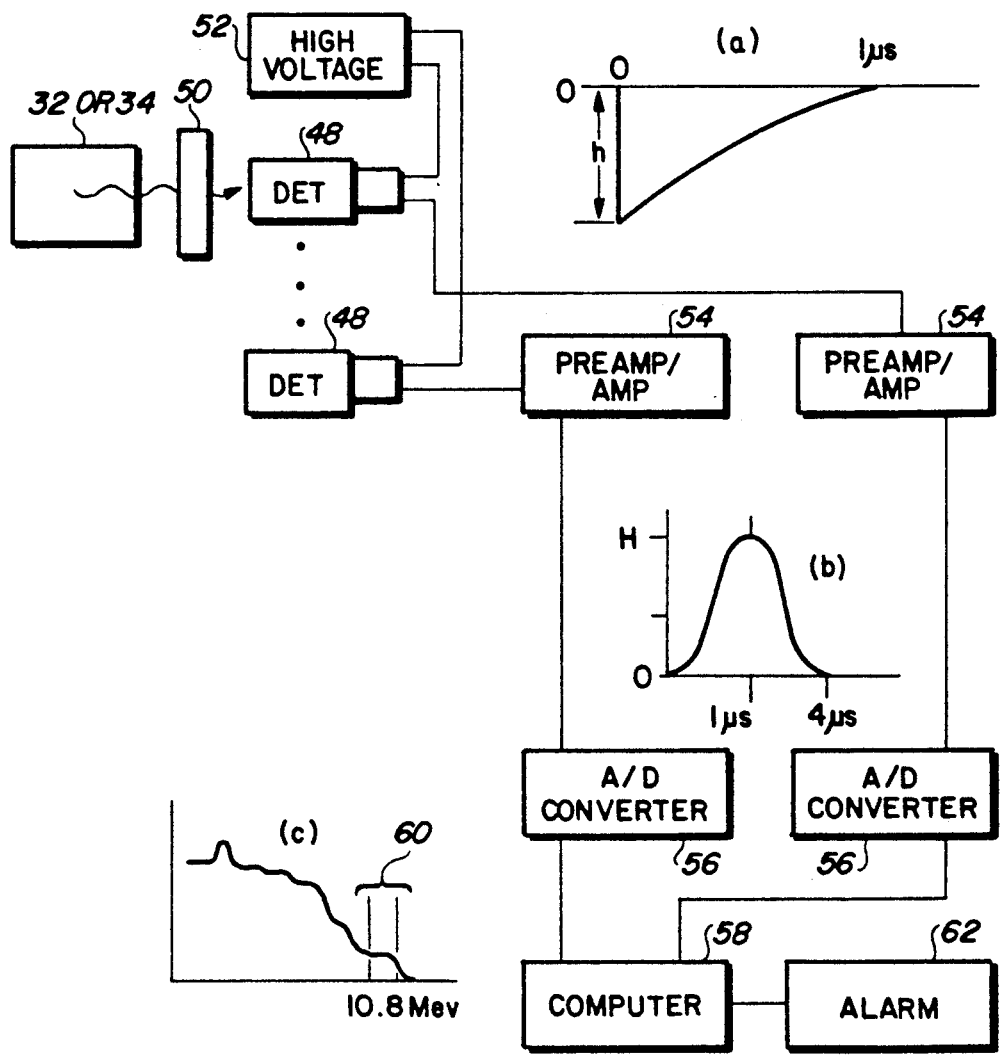
FIG. 4 is a block diagram of the system showing the detection of particular gamma rays used in the detection of explosive material, with waveforms (a), (b) and (c) in FIG. 4 being representative of the signals at particular points in the system.

FIG. 4 illustrates in general the detection of the information by any one of the individual detectors 48. As shown in FIG. 4, neutrons from the sources, either 32 or 34, are thermalized and impinge on a piece of luggage or parcel as represented by the block 50. The individual detectors 48 forming the C-ring detector structures, each detect the production of gamma rays. The reaction between the thermal neutrons and the nitrogen in the explosive or other material, is as follows:

$$^{14}_7N + _0^1n_{th} \rightarrow ^{15}_7N + \gamma$$

The first factor in the above equation is the nitrogen in the explosive or other material within the luggage. For example, wool, cotton, etc. all contain nitrogen. The nitrogen when bombarded with thermal neutrons, as shown by the second factor, produces nitrogen in a changed form (another isotope of nitrogen) plus gamma rays, of which approximately 14% are at 10.8 MeV. Each gamma ray as detected by a detector 48 produces an output from the detector as shown in waveform (a) in FIG. 4. As can be seen, the detector 48 produces an output signal having a height "h" and decaying exponentially to zero in approximately one micro second. The detectors 48 are supplied with a high voltage from a high voltage source 52. The height "h" and the area under the decaying signal are both proportional to the gamma ray energy.

The output from each detector 48 is passed directly through a preamp and amplifier 54 to produce an output signal as shown in waveform (b) in FIG. 4. It can be seen that the individual gamma ray is converted from the exponentially decreasing signal to a pulse signal having a height "H" which is proportional to the area under the signal shown in waveform (a). It is to be appreciated that each gamma ray received by each detector 48 produces successive signals representing the concentration of nitrogen.

The output from the preamp/amplifier 54 is passed through an analog to digital (A-to-D) converter 56 to produce a digital number representing the height "H" of the waveform (b) of FIG. 4. It can be seen, therefore, that the outputs from A-to-D converters 56 are a series of digital numbers representing the detection of gamma rays, which in turn represent the concentration of nitrogen. A small range of the digital numbers correspond to the gamma rays of interest. As more and more gamma rays are detected at each detector, the digital number from the A-to-D converters 56 at each point in time is counted. The counts of each digital number which occurs, which is proportional to the number of nitrogen gamma rays incident on the detector, are then coupled into a computer 58 for computation of a profile for each slice or plane of the object under observation and for the production a three dimensional representation of the concentration of nitrogen of the object. Waveform (c) illustrates the profile of the spectrum received by the detectors 48 and with the space 60 between the two lines representing the area of interest, more specifically the gamma rays representing nitrogen.

An alternative technique (and a preferred technique in most instances) for processing the detector signals, and in particular for accurately counting the signals at a high rate, is described in Drndarevic, Ryge & Gozani, "A Signal Processor for High Counting Rate gamma ray Spectroscopy with NaI(Tl) Detectors," *IEEE Proceedings of Nuclear Science* (Feb. 1988), which article is incorporated herein by reference. The processor described in the referenced article advantageously addresses the problem of "pile up" and allows very few valid pulses to be lost while minimizing interfering background noise.

FIGS. 5(a), (b) and (c) illustrate typical profiles for explosive material in a block form; non-explosive materials, such as a wool coat or jacket; and explosive material in sheet form. As can be seen in FIG. 5(a), which represents the detection from one column of detectors at four successive planes as the object moves past the detectors, the high readings of 12 in two successive planes and 8 in the third successive plane, represent a high concentration of nitrogen rich material probably representative of a block of explosive material. The detectors in the other column and along the row would confirm the presence of such block material. The large difference between readings in the profile of FIG. 5(a) show an unusual density of nitrogen material not typical in other types of items which contain nitrogen.

For example, FIG. 5(b) illustrates an item such as a wool coat or suit which may contain a relatively high amount of nitrogen, but with the nitrogen spread out in a diffuse pattern which would not be representative of an explosive material. Although the overall nitrogen content of the wool article is quite high, the concentration does not reach the levels of explosive material.

FIG. 5(c) illustrates an explosive material in a sheet form along one side or edge of the luggage and again, the concentration of nitrogen and high readings relative to the lower readings indicates the presence of something having a relative high concentration of nitrogen, plus a relatively high density for this concentration. This again would typically be a profile of an explosive material. The computer 58, therefore, may be programmed to identify such specific profiles and provide for an alarm such as through an alarm 62 so that the luggage or parcel may be subjected to a more thorough inspection.

Figure 6:
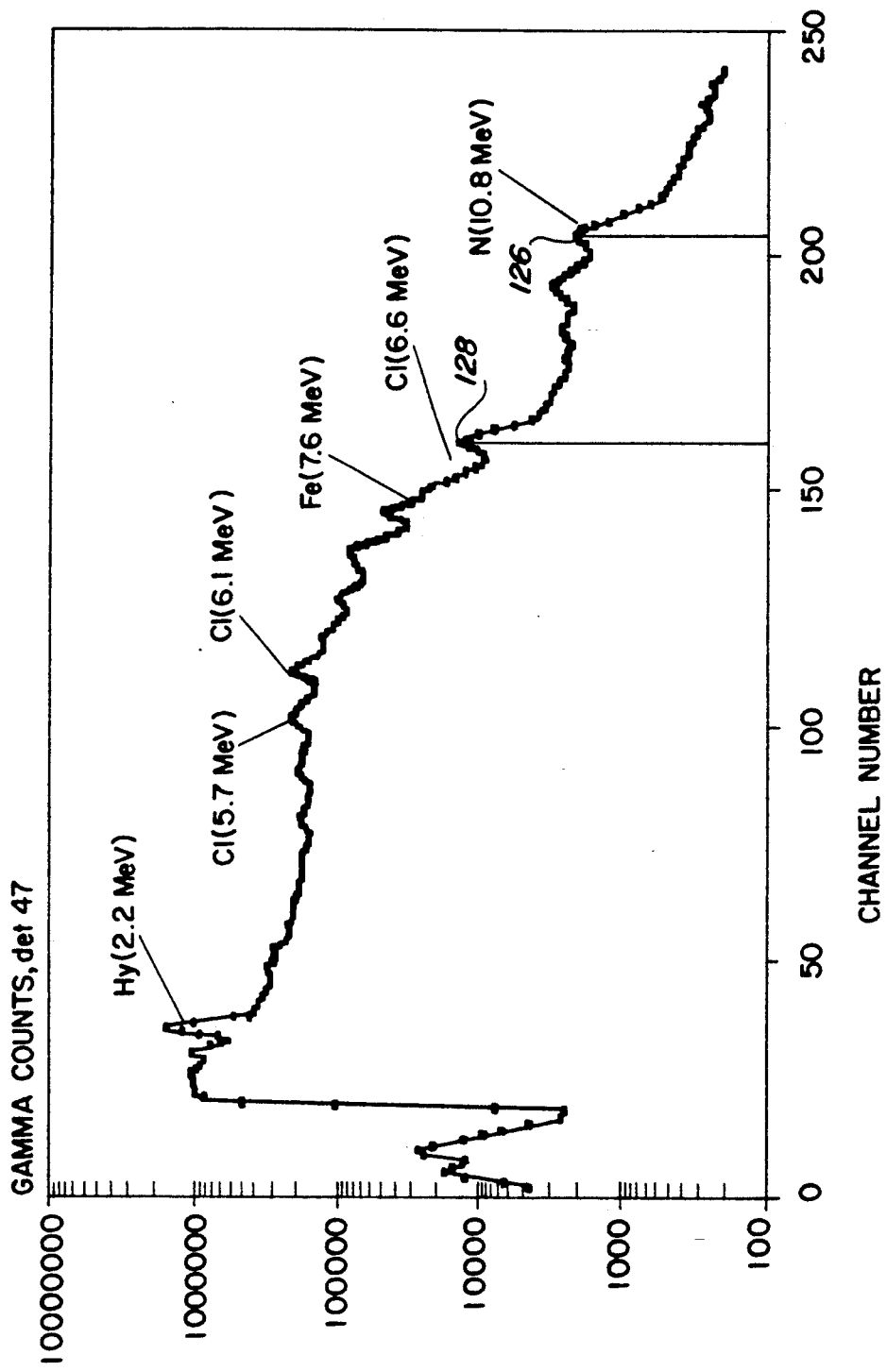
FIG. 6 illustrates a typical thermal neutron activation gamma spectrum, and further illustrates the manner in which background noise form one area of the spectrum is subtracted from another area of the spectrum in order to remove background noise.

Referring next to FIG. 6, a typical thermal neutron activation gamma ray spectrum is illustrated. The vertical axis represents the gamma ray count; the horizontal axis represents the particular channel number through which the count is detected. As each channel is set up to measure a particular energy level, the horizontal axis is thus proportional to the various energy levels of the detected gamma rays. A good description of the types of instruments and measurement techniques used to detect nuclear radiation, such as gamma rays, may be found in, e.g., *Nuclear Instrumentation*, Section 1.5, pp. 4–18 (McGraw-Hill Series in Nuclear Engineering).

In FIG. 6, it is seen that the gamma ray peak 126 corresponding to nitrogen, labeled "N (10.8 MeV)", has a smaller amplitude than does the surrounding background noise. Thus, in order to better detect the gamma rays occurring at 10.8 MeV, the present invention contemplates using a spectral correlation method (SCM), or similar technique, to reduce the background noise. A preferred SCM is described in Appendix B, filed herewith and incorporated herein by reference. Essentially, the SCM described in Appendix B determines the background noise at the desired location of the spectrum i.e., the nitrogen peak, by correlation with other spectral regions such as near the chlorine peak 128 (8.6 Mev). Interferences from weak peaks in the desired region can be determined by measuring as associated strong peak elsewhere in the spectrum and subtracting the appropriate fraction from the region of interest. As the sources of background noise in the system are fundamentally related over the entire spectrum, i.e., the noise at one location is related to the noise at another location, this background subtraction technique has the desired effect of removing much of the background noise near the spectral peak of interest.

FIG. 6 also shows additional gamma ray peaks which correspond to other elements, e.g. hydrogen, chlorine. Gamma rays detected in these peaks can be used to measure the amount of elements other than nitrogen present in the object under investigation. Measurements of these elements are used to further enhance the detectability of contraband, e.g. explosives, in the object. For example, explosives typically exhibit hydrogen in combination with nitrogen. Thus, the presence of a characteristic nitrogen signal without a characteristic hydrogen signal is not typical of most explosives, whereas the presence of a characteristic nitrogen signal in combination with a characteristic hydrogen signal is typical of most explosives.

Figure 7:
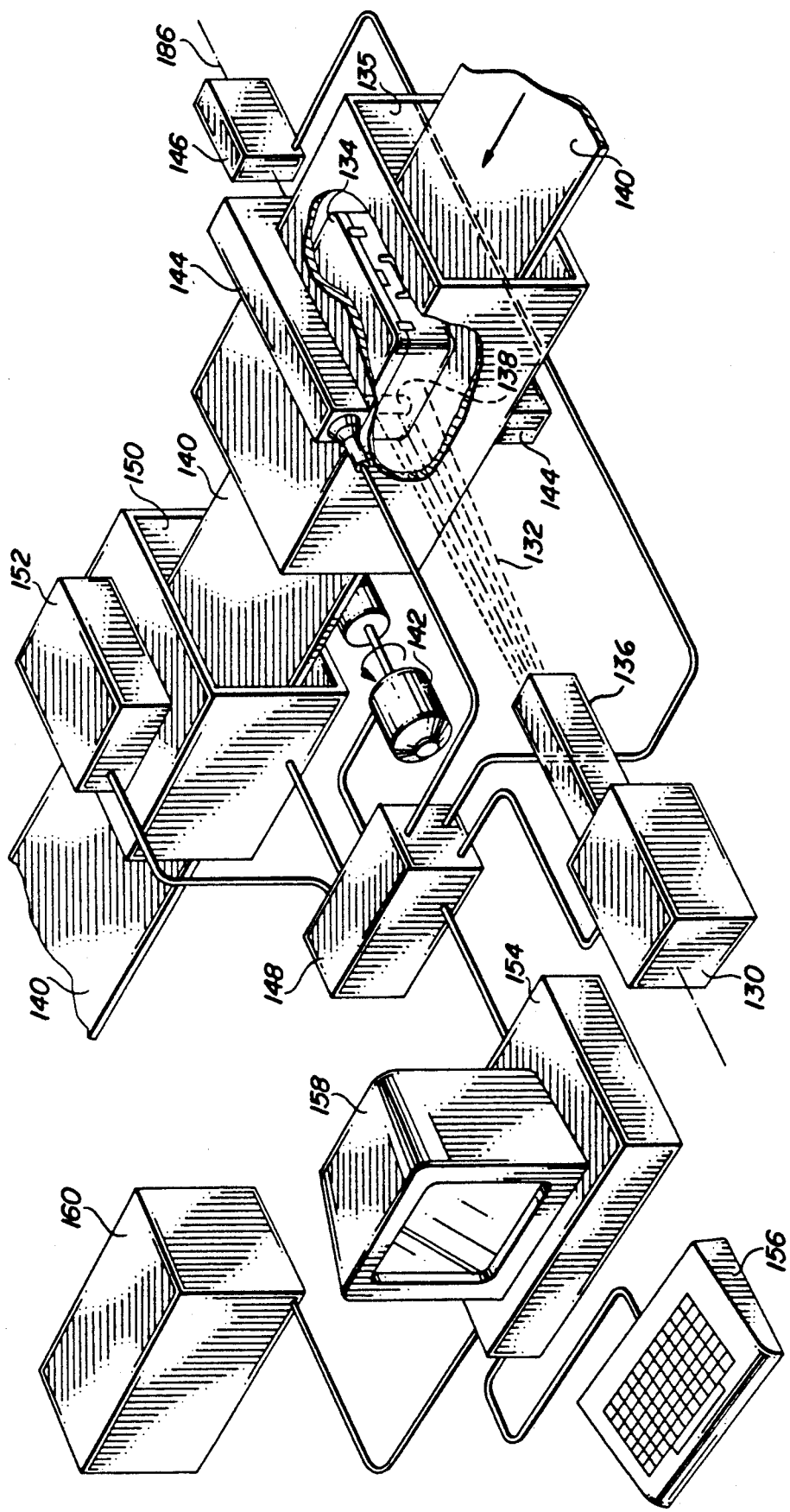
FIG. 7 schematically illustrates the neutron detection system of the present invention combined with an X-ray system.

Referring to FIG. 7, a schematic representation of the principal hardware components that may be included in a further embodiment of the present invention is illustrated. A source of neutrons 130 directs thermal neutrons 132 to a parcel or object 134, the contents of which are to be investigated. If desired, a collimator 136 may help direct the neutrons 132 so as to irradiate a desired cross sectional shape at the point where the neutrons enter the object 134. As shown in FIG. 4, for example, the cross sectional shape of the irradiated portion may assume that of a narrow rectangle 138.

The object 134 is carried past the source 130 of thermal neutrons 132 within a shielded chamber 135 on a conveyor belt 140, or equivalent parcel-carrying mechanism. The conveyor belt 140 is driven by a motor 142 in a continuous or step-wise fashion. The conveyor belt 140 continues to carry the object 134 through a chamber of a conventional X-ray system 150 wherein a source of X-rays 152 and a corresponding detector (not shown) are used to produce an ordinary electron density image of the object and its contents.

An array 144 of gamma ray detectors are selectively positioned around the object 134 near the region where the object is irradiated by the neutron beam 132 within the shielded chamber 135. It is to be appreciated that while only one array 144 of such detectors is shown positioned above the object 134, several such arrays may be used, e.g., one above the object as shown, one below the object, and one behind the object, thereby forming a C-ring that effectively encircles the object 134 as it is irradiated, as shown in FIG. 3. In addition to the array of gamma ray detectors 144, at least one neutron detector 146 is placed behind the object 134 opposite the source of neutrons 130. This neutron detector 146 captures many of the neutrons that pass through the chamber 135 and the object 134 without interacting with any atomic nuclei. Additional neutron detectors may be placed at other locations in the cavity.

Appropriate control circuits 148 interface with the above-described components. The control circuits, in turn, are monitored or driven by a suitable computer 154. the computer 154 includes conventional input/output devices, such as a keyboard 156, a terminal display screen 158, and/or a printer (not shown). A non-volatile memory storage device 160, such as a disk or tape memory, may also be coupled to the computer 154, as required, in order to retrieve or track the large amounts of data that may be needed to examine a large quantity of objects for specified contraband.

In operation, the object 134 is irradiated by the neutrons 132 in sections or slices as the object moves past the beam. The gamma rays resulting from the interaction of the neutrons with atomic nuclei in the object are detected in the gamma ray detector array 144. Neutrons that pass through the chamber 135 and object 134 are detected in the neutron detector by each detector 146. The number of gamma rays at specified energy levels detected by each detector in the array provides a measure of the particular element, or combination of elements, present within the irradiated slice or section of the object characteristic of that level of gamma ray emission. By combining this information from all of the detectors, as well as by considering the number of neutrons that pass through the object without interacting with atomic nuclei (as sensed by the neutron detector 146), a density distribution of the elements within the irradiated section of the object may be obtained. By combining such density information for all of the slices of the object that are created as the object moves past the neutrons 132, a three-dimensional density image of the contents of the object can thus be formulated.

Advantageously, the nuclear density information obtained using the gamma ray and neutron detectors as above described can be further enhanced by combining it with the electron density information obtained from the X-ray system 150. If such combined density information suggests the presence of contraband, the object is flagged for further investigation (e.g., diverted off of the conveyor belt for a manual search). A preferred manner in which the X-ray image of the electron density is correlated with the gamma ray image of the nitrogen density is set forth in Appendix A, filed herewith, and incorporated herein by reference.

As suggested in the embodiment of the invention shown in FIG. 7, it may be desirable (although not mandatory) that the neutrons 132 be directed toward the interrogated object 134 through a collimator 136. The collimator 136 may be of conventional design, well known in physics, and is comprised of neutron scattering and absorbing materials of densities that ensure a desired tailoring of the cross section of the neutron beam, including the reduction of the neutron flux impinging on the gamma ray detectors. The gap of the collimator thus defines a narrow fan-shaped beam of source neutrons that fall upon and enter a known section or volume element (voxel) of the interrogated object. The use of the collimator 136 advantageously allows a set of fan-shaped neutron beams to be generated, thus facilitating the building of independent irradiation stations and assuring greater economy of the source neutrons.

Referring back to the embodiment of the invention in FIG. 4, it is seen that the outputs of the A/D converters 56 are directed to a computer 58. It is one of the main functions of the computer 56 to analyze the data (e.g., the number of gamma rays at a particular energy) sensed by each of the detectors 48 in order to accurately and rapidly classify an object as one with or without explosives. A similar function must be performed by the computer 154 shown in the embodiment of FIG. 7. (Other functions, such as record keeping and miscellaneous housekeeping functions associated with the explosive detection system may also be performed by the computers 58 or 154, but such functions are viewed as conventional functions and will not be described herein.)

There are a number of data analysis techniques that can be used within the computers to achieve their classification function. Two such approaches are described herein: (1) standard decision analysis; and (2) artificial neural system (ANS) analysis. Of these two approaches, the preferred approach is ANS because, as indicated below, it provides a PD that is as much as 2.5% greater than the PD achieved using standard decision analysis at the same throughput and PFA levels.

Regardless of which approach is used, however, it is helpful in some instances (but not all instances) to first identify certain "features" that are present in the detector and other data. By identifying such features within the data, and presenting such features to the ANS system (as opposed to presenting raw detector data to the ANS system) the classification function can be significantly simplified, even though the set-up and calibration of the ANS system (i.e., the process of determining the features) may be somewhat more complicated.

Each individual detector in the system produces some information about the amount and location of the elements, e.g., nitrogen, in the object under examination. Unfortunately, due to interference with other elements, statistical fluctuations, and the like, there is a substantial amount of noise present in the system. In fact, the signal-to-noise ratio for any single detector is rather low. This low signal-to-noise ratio can be improved somewhat by combining the information from several detectors with overlapping fields of view. For example, by averaging two detectors, the signal-to-noise ratio can be improved by a factor of the square root of two. Generally, however, combining more and more detectors worsens the spatial resolution of the system. Hence, a tradeoff must be sought that provides an acceptable signal-to-noise ratio on the one hand and an acceptable spatial resolution on the other hand. Both criteria are required to improve the ability of the system to detect explosives.

To satisfy both the spatial resolution and signal-to-noise ratio requirements, it is thus helpful in many instances to define a set of "features" with different amounts of noise resistance that still provide helpful and adequate spatial information. A "feature" may thus be any combination of detector signals in the detector array. Some of the features may be simple; others may be complicated (such as the reconstructed three-dimensional nitrogen density distribution), and may require imaging techniques. A set of features can be defined by: (1) calculating or estimating certain anticipated features that would normally be present for a set of typical objects (e.g., pieces of luggage) containing explosives; (2) developing calibration techniques using different sets of these features; and (3) testing the performance of the calibration techniques on a test set of data.

Experiments have shown that the variance for any feature is roughly the same for objects with explosives as it is for objects without explosives, even though, of course, the values of the feature may differ between the two classes of objects. It is also true that the distribution of "bombness" (i.e., the likelihood of explosive materials being present) in objects, such as suitcases, is decidedly non-normal. Most suitcases, for example, contain little nitrogen, and are thus quite easy to classify as non-threatening (containing no explosives). However, a significant percentage of the pieces of luggage encountered in airports and similar locations contain sufficient nitrogen and other interfering materials to falsely alarm the detection system, absent some further classification criteria. The distribution of "bombness" thus follows (roughly) the distribution of nitrogen, that is, with most pieces of luggage occurring at low levels of threat but with an extensive tail to the distribution. The addition of a simulated threat shifts the distribution without distorting its shape. This results in the variance for any feature being the same for objects with and without threats, as stated above.

Standard Decision Analysis

The first (and more conventional) approach used to classify the objects under examination as containing or not containing explosives is referred to as standard decision analysis. The basic technique used in standard decision analysis is linear discriminant analysis. In linear discriminant analysis, a discriminant value is computed by a linear combination of the values of a set of features measured for a piece of luggage. If the discriminant value is greater than some prescribed threshold, e.g., zero, the piece of luggage is classified as containing a threat; otherwise, the piece of luggage is cleared.

Geometrically, the features are axes which define the classification hyperspace. The measurement of any particular piece of luggage (e.g., suitcase) is plotted as a point in this space. The points for suitcases without threats cluster separately from those with threats. The hyperplane that best separates the two clusters may be viewed as a dividing surface that results from the linear discriminant function. In fact, the computed discriminant value is just the normal distance of the hyperplane from the point which represents the piece of luggage, with the sign (positive or negative) representing which "side" of the hyperplane the point is on. Quadratic or other functional forms may be used for the discriminant, which will result in dividing surfaces which are something other than planes.

Application of the usual least squares technique to the classification problem results in the dividing hyperplane being perpendicular to the line that joins the centers of the two clusters. This plane is also halfway between the two centers, if the distance is measured after normalization by the covariance matrix. Any overlap between the two clusters determines the possible tradeoff between detection and false alarm rates. By moving the dividing hyperplane along the line joining the two centers (which is equivalent to changing the threshold the discriminant value must exceed) this tradeoff can be set to any level, from zero false alarm rate (and a low detection rate) to 100% detection and a commensurately higher false alarm rate. In addition, the value of the discriminant implies a "sureness" for the decision. This value may be used in some kind of Bayesian analysis or may simply map onto the tradeoff curve as the PD/PFA point that would result if the threshold were set at that value.

Unfortunately, in practice, the development of the discriminant is a complicated problem. First, a classification of the detector data set must be made so that pieces of luggage which result in similar instrument responses are grouped together. For example, large heavy suitcases are analyzed as one group. Next, the set of features to be used in each group must be chosen. The computation of the discriminant coefficient is relatively straightforward once the features are chosen. A variety of computer programs are commercially available for performing this computation. Some adjustments must be made to improve performance by allowing some regions of the decision space to have special decisions made. These are situations where a "by hand" technique takes advantage of the fact that the distribution of the objects under investigation is non-normal. Finally, the resulting calibration is tested on a set of data not used in the calibration and, eventually, on-line during the supervised tests. Experience using this technique has revealed that a separate calibration must usually be developed for the bulk and sheet explosives due to their different measured response in the system. Unfortunately, a significant amount of time, e.g., several days of statistical analysis, is typically required in order to correctly perform this discriminant development and calibration.

It is preferred that the robustness of this calibration procedure be tested, and that based on such test, adjustments be made as required in order to provide a robust calibration. Testing robustness may be performed by taking a large data set (obtained from passing a large number of pieces of luggage through a detection system as herein described) and breaking it into several different groups or subsets. A calibration may then be performed on all but one group of subset, and then tested on this last subset. Each subset in turn is then used as the test subset in a manner similar to that used in jackknife analysis. The difference between the performance of the calibration on itself and on the test subset provides a measure of robustness. A large difference indicates poor robustness. The number of classification groups and features in each group may then be chosen and adjusted as required until the calibration becomes robust.

Representative data obtained from a particular embodiment of the present invention (using a Californium-based neutron source), including a detailed description of the calibration procedures, is included in Appendix C, filed herewith, and incorporated herein by reference.

Artificial Neural System (ANS) Analysis

An (ANS) may be described as a collection of simple processors (neurons) that are connected in a massively parallel network. In one embodiment of an ANS, each neuron accepts inputs from several others with a different weight applied to each link. If the sum of the weighted inputs exceeds some present value, the neuron "fires" and sends its output signal to other neurons. Some neurons (the input layer) connect directly to the available inputs to the ANS. Other neurons (the output layer) connect to the desired output signal (which, in the case of an explosive detection system, comprise output signals ranging from "no threat" to "must be a threat"). Training or calibration objects are presented in the form of the input signals corresponding to a desired output, and the weights in the network are adjusted according to a learning rule until the network predicts the correct desired output. The weights are then frozen, and the trained ANS is then used on a test set of data to identify threats. Advantageously, the training step requires no operator intervention once the data is assembled; the network is simply allowed to iterate to a solution. If the proper network architecture has been established, the ANS can be trained with far less operator involvement than with the discriminant analysis approach described above.

Figure 8:
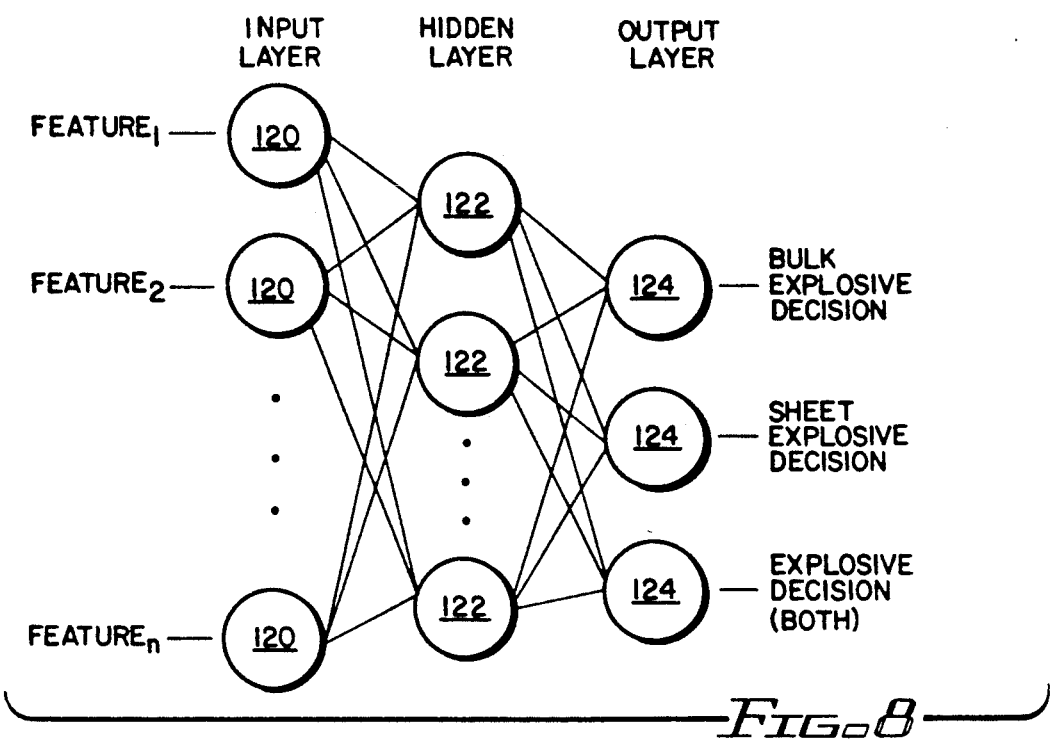
FIG. 8 depicts a three layer back propagation network of a preferred ANS that may be used in analyzing the detector data of the present invention for the purpose of classifying whether the object under investigation carries explosives.

It is seen that an ANS is simply one form of a parallel distributed network (PDN) made up of processing elements (PE's) that are interconnected via information channels called interconnects. Where these PE's perform a simple function, such as "on" if the weighted inputs thereto exceed a prescribed threshold, and "off" if not, these PE's may be referred to as "neurons." Each PE or neuron may have multiple input signals, but typically only one output signal (although this output signal may be connected to several different locations within the ANS). The PE's are arranged in several different layers. A first or input layer of PE's is generally characterized by each PE having an input that comprises one of the input signals to the PDN. An output layer of PE's is characterized by each PE providing one of the output signals of the PDN. The output signals from each PE in the input layer comprise the input signals to the PE's of other layers, either in a feedforward or feedback interconnect, and these interconnections, as indicated, may be weighted by an appropriate factor. For simple PDN applications, two layers of PE's may be sufficient, in which case the PDN comprises only an input layer and an output layer. For more complex applications, one or more hidden layers of PE's may be required intermediate the input and output layers. The complexity of the PDN is largely governed by the number of layers of PE's. The general structure of a three-layer PDN or ANS, for example, is illustrated in FIG 8. This particular three-layer ANS is further discussed below.

Parallel distributed networks are described in the art. See, e.g., Rumelhart, et al., *Parallel Distributed Processing*, Vol. I (MIT Press, 1986). In general terms, such systems are characterized as including: (1) a set of processing units or elements; (2) a state of activation (i.e., the current state of the element); (3) an output function for each element (i.e., a function that defines the output signal as some function of the input signals); (4) a pattern of connectivity among the processing elements; (5) a propagation rule for propagating patterns of activities (signals) through the pattern of connectivities; (6) an activation rule for combining the inputs impinging of a processing element with the current state of that element to produce a new level of activation for the element; (7) a learning rule whereby patterns of connectivity may be modified by experience; and (8) an environment within which the system operates.

One advantage of using an PDN or ANS is that it can adapt or self-adjust the strength of the interconnections between processing elements. Self-adaptation allows an ANS to "learn" and to eventually improve in overall system performance.

Learning results from application of a selected learning rule. Most learning rules comprise variants of the Hebbian learning rule which states that it two units (processing elements) are highly active, the strength of the interconnect between these two units should be strengthened. A variation of this learning rule is the delta rule. According to the generalized delta rule, the amount of learning (i.e., the strength or weight of the interconnect between two processing elements) is proportional to the difference (or delta) between the actual activation achieved and a target activation provided by a teacher. This delta rule is discussed at length in Chapters 8 and 11 of Rumelhart reference, cited above, and several variations or extensions of the rule exist. The delta rule, its variations and/or extensions, provides the primary learning rule utilized by the ANS of the present invention. Although other learning rules, known or yet to be developed, could of course be used with the explosive detection system, use of the delta rule advantageously provides an effective way to accurately teach the ANS how to recognize an object containing an explosive based on using objects having known explosives as the "teacher".

The particular learning rule selected for a given application is often referred to in the art as a "paradigm of learning." As indicated, numerous paradigms of learning exist and are documented in the art.

Two variations of an ANS-based explosive detection system are contemplated by the present invention: (1) a system wherein the raw data from the detectors (the detector counts) comprise the input signals to the ANS; and (2) a system wherein developed "features" from the raw detector data, as described above, comprise the input signals to the ANS.

In accordance with the first variation, the ANS is initially taught by presenting to it detector counts for objects being examined and the category of each object (whether or not an explosive is present). These objects comprise a training set of objects. The ANS then adjusts the interconnection strengths between th various processing elements, using an appropriate learning rule, such as the delta rule, to assure the correct classification of each object in the training set. Observations (e.g., detector counts) for different objects (not in the training set) are next presented to the ANS, which in turn, classifies each object based on the strength of the interconnections resulting from the training set. Advantageously, using raw data from the detectors, (as opposed to using "features" of the detectors), significantly reduces or eliminates the time-consuming steps of computing and developing features. Disadvantageously, use of raw detector data requires a significantly longer training time for the ANS. This is because the number of detectors, and hence the number of inputs to the ANS, is significantly larger than is the number of detector features, resulting in a much more complex (increased number of levels) ANS that must be used. For example, use of raw detector data (assuming detectors similar in scope to these shown in FIGS. 2 and 3) requires around 200 input neurons (signal connections) to the ANS. With 200 input signal lines, two hidden layers of PE's in the ANS are required in order to achieve a reasonable performance. In contrast, use of detector features requires only around 20 input neurons, and thus greatly simplifies the complexity of the ANS. For this reason, the use of detector features is preferred over the use of raw detector data as inputs to the ANS neurons.

In accordance with the second variation of the ANS-based detection system, "features" are developed from the detector signals as described above. These features comprise the input signals to the ANS. A diagram of a preferred ANS used with this variation is shown in FIG. 8. This ANS comprises a three-layer, fully connected, feedforward network. The network includes a first layer (input layer) of neurons (or PE's) 120. This input layer receives a set of pre-computed feature vectors from the explosive detection system that have been normalized to gray scale values between −0.5 and 0.5. A middle layer (hidden layer) of neurons 122 learns to encode features that are not explicitly present in the input patterns. A last layer (output layer) of neurons 124 produces a gray scale value that can be compared to a threshold to obtain a decision. The output layer is coded with +0.5 if the object being examined contains an explosive threat, and −0.5 if it does not. While the steps of computing and developing such "features" for use with this second variation may consume a noticeable amount of time, once a set of features has been developed, the number of input neurons for the ANS can be significantly reduced, and the complexity of the ANS network can be greatly simplified, over that which would be required if the first variation were used (raw detector data connected directly to the input neurons of the ANS).

Advantageously, by using the network shown in FIG. 8, no preclassification (large, small, etc.) of the objects, such as is used in the discriminant analysis approach, is required. The list of features fed into the network may include all those that are used with the discriminant functions, which features may include some which have significant collinearity. Training of the network is accomplished by presenting a training data set to the network over and over again, at a relatively low learning rate. Advantageously, such training can occur with only minimal human supervision. Back Propagation (BP) is used as the paradigm of learning for the system. BP is based on the generalized delta rule, mentioned above, and is well documented in the art. Essentially, this rule is a steepest descent method of computing the interconnection weights between neurons of the ANS that minimizes the total squared output error over a set of training vectors. Evaluation of the effectiveness of the ANS network may be judged by simply observing the residual error (as the network can be expected to make errors and have false positives), and/or by simply measuring the PD and PFA rates for a test set of objects.

Figure 9:
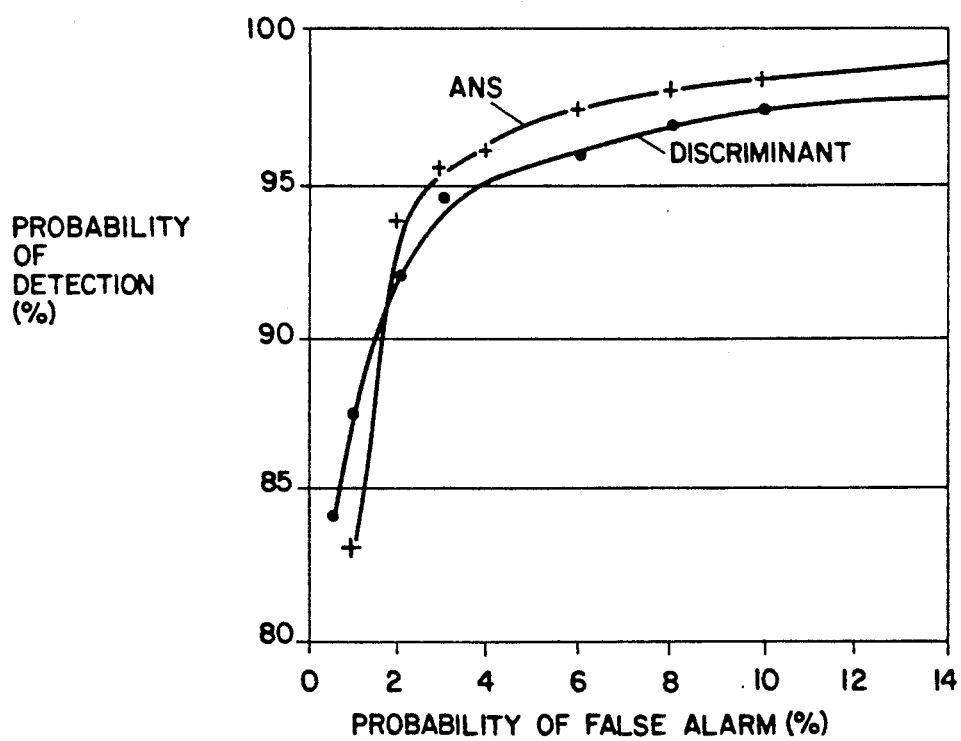
FIG. 9 is a graph that compares the probability of detection and the probability of false alarms obtained with an explosive detection system using an ANS analysis of the detector data verses an explosive detection system using a more conventional discriminate analysis of the detector data.

A performance comparison between an explosive detection system using the discriminant analysis approach and one using an ANS trained by the BP technique is depicted in FIG. 9. The performance of both techniques is evaluated on a test set of objects that is different from the training set. Since the outputs of both techniques produce gray scale values, different thresholds ca be applied to get different performance points on the PD PFA tradeoff curve. Each curve in FIG. 9 was generated by changing the thresholds for the decision over the applicable range.

FIG. 9 clearly shows that the ANS approach performs better than the discriminant analysis approach for false alarm rates greater than 1.75%. For example, at the operating point of 95% detection (which is a typical operating point for a viable explosive detection system), the ANS reduces the false alarm rate by around 1.5–2.0%. Advantageously, for an explosive detection system having a high throughput of objects, this results in substantially fewer objects having to be scanned or checked by secondary techniques. At slightly higher detection rates, e.g., 96%, the ANS reduces the difference between the PFA rates still further (even though the value of the PFA goes up for both approaches).

One advantage offered by the BP-trained ANS network over the discriminant analysis approach is that ANS takes relatively less human supervision. As noted above, calibration of the discriminant analysis may require several days of statistical analysis. With the BP technique, only a few hours of set up time are required by a computer literate person, and a day or two of computer time (to train the system).

As seen in FIG. 9, the performance of the ANS network at low false alarm rates (less than 1.75%) is substantially lower than for the discriminant analysis technique. This is believed to be caused by the particular activation function used in the ANS network. (The activation function is that function which defines the relationship between the output of a particular neuron and its input(s).) The sigmoid function was used, and this function is very steep in the middle (i.e., at net input values close to zero). Consequently, most of the output activation values tend to cluster around −0.5 and +0.5. Inevitably, there will be a few non-threatening objects that have similar characteristics to threatening objects. In these instances, the non-threatening objects will also have a value close to +0.5. In order to remove these objects, the threshold would need to be adjusted close to +0.5. However, doing so would cause the detection rate to drop rapidly. Hence, it is believed that a better solution to this problem (of low performance at low PFA rates) is to use a smoother activation function.

The ANS portion of the present invention may be implemented through custom software and/or hardware installed in or coupled to the computer 116 (FIG. 1) or the computer 58 (FIG. 4), hereafter the "host" computer. One implementation, for example, includes an array processor network, or "card", that is installed in or coupled to the host computer. A suitable array processor network that can perform this function is described in U.S. patent application Ser. No. 07/191,207, filed May 6, 1988 (assigned to the same assignee as is this application), which patent application is incorporated herein by reference. The advantage of using an array processor of the type described in the referenced patent application is that the ANS computations can be quickly performed, with many of the computations being performed in parallel.

Another implementation involves modeling the ANS using software. A suitable modeling program that simulates an ANS network on a conventional IBM PC/AT or compatible computer, for example, is commercially available from Science Applications International Corporation (SAIC), San Diego, Calif. 92121 under the name of "ANSim." By using the ANSim program, an IBM PC/AT or compatible computer, and related equipment as detailed in applicants'prior application, Ser. No. 07/367,534, which application is incorporated herein by reference, it is thus possible to readily model the ANS portions of the present invention.

In conclusion, the present invention is directed to an explosive detection system using neutrons from a source to impinge on a object potentially containing explosive material and with the neutrons reacting with the nitrogen or other elements contained in the object to produce gamma rays. The gamma rays are detected by suitable detectors, such as inorganic scintillators, and in a preferred embodiment, the scintillators are arranged so as to surround the object to provide for detection of a two dimensional slice or plane of the object under observation. A neutron detector may also be used to measure neutron flux in the same vicinity as the gamma ray detectors. The object is moved continuously through the ring of detectors so that successive slices or planes provide for the build up of a three dimensional profile of the nitrogen bearing material within the object under observation. The three dimensional profile may then be used to determine of the concentration and distribution of the nitrogen bearing material and to make a determination whether such nitrogen bearing material has a profile likely to be an explosive material, such as high nitrogen density. This determination is enhanced by correlating the nitrogen density image thus obtained with an X-ray image of the same object. In one embodiment, the determination is further facilitated through the use of an Artificial Neural System, or equivalent parallel distributed network. Use of an ANS advantageously results in a PD for the system that is increased and/or a PFA of the system that is decreased over that which is achievable using conventional standard decision analysis.

In one embodiment, the inorganic scintillator is sodium iodide, and two oppositely disposed C-ring detectors having their open ends facing each other are used to provide for a complete profile of each slice or plane along all four sides. In addition, the gamma ray detectors may be formed of sets of detectors in rows and columns to increase the detection capability by receiving additional gamma rays produced by the interaction of the thermal neutrons and nitrogen in the cavity. The present invention, therefore, provides for a greater resolution and efficiency in the detection of potentially explosive material and, because this is accomplished in a fast period of time, also provides for an adequate throughput of the luggage or parcels through the detection system.

While the invention herein disclosed has been described by means of specific embodiments and applications thereof, numerous modifications and variations could be made thereto by those skilled in the art without departing from the scope of the invention set forth in the allowed claims. For example, instead of using a TNA-based system to probe or scan the luggage or parcels in order to cause the characteristic gamma rays to be emitted from the materials contained within the luggage or parcels, other equivalent or similar systems could be used. For example, an FNA (fast neutron activation) system could be used. So long as gamma rays or other indicia representative of the composition of the materials within the parcel or luggage are generated, and so long as a suitable detection system or mechanism is used to quantitatively sense the gamma rays or other indicia, an ANS system as described herein may be used to analyze the detected radiation (gamma rays or other indicia) for the purpose of determining whether explosive or other materials are present within the parcel or luggage. Advantageously, the ANS portion of such a detection system may perform its function of discriminating between parcels with and without the materials of interest simply by learning from examples, as opposed to being programmed with complex algorithms based on conventional statistical analysis techniques.

Particular features of the invention are set forth in the claims that follow.

Gozani, et al
Docket 47475

MULTI-SENSOR EXPLOSIVE DETECTION SYSTEM

A P P E N D I X   A

CERTIFICATE OF MAILING BY "EXPRESS MAIL"

Express Mail Mailing Label No. B03803631W
Date of Deposit 1-10-90

I hereby certify that this paper or fee is being deposited with the United States Postal Service "Express Mail Post Office to Addressee Service" under 37 CFR 1.10 on the date indicated above and is addressed to the Hon. Commissioner of Patents and Trademarks, Washington, D.C. 20231

Bryant R. Gold
(Typed or printed name of person mailing)

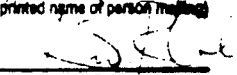
(Signature of person mailing)

SAIC-88/1754

XENIS PHASE II

FINAL REPORT

June 27, 1988

Science Applications International Corporation
2950 Patrick Henry Drive
Santa Clara, CA 95054
(408) 727-0607

The following report is a record subject to the provision of 14 CFR 19.1 et. seq. Release of information contained herein is prohibited without the express written approval of the FAA Director of Civil Aviation Security or his designee.

TABLE OF CONTENTS 1.0 INTRODUCTION . . . . . . . . . . . . . . . . . . . . . . . . . . 1-1
   1.1 General . . . . . . . . . . . . . . . . . . . . . . . . . . 1-1
   1.2 General Philosophy - The Multi-Mode Approach . . . . . . . . 1-3
   1.3 Scope of Report . . . . . . . . . . . . . . . . . . . . . . 1-5
2.0 DESCRIPTION OF MACHINE . . . . . . . . . . . . . . . . . . . . . 2-1
   2.1 Mechanical Description . . . . . . . . . . . . . . . . . . . 2-1
   2.2 Description of Electrical Requirements and Electronic
       Interfaces Between System Components . . . . . . . . . . . . 2-5
   2.3 Software Design . . . . . . . . . . . . . . . . . . . . . . 2-8
3.0 THEORY OF OPERATION . . . . . . . . . . . . . . . . . . . . . . 3-1
   3.1 Background for the Thermal Neutron Activation (TNA)
       Technique . . . . . . . . . . . . . . . . . . . . . . . . . 3-1
   3.2 Correlation with X-Ray Image . . . . . . . . . . . . . . . . 3-2
   3.3 Features from TNA Alone . . . . . . . . . . . . . . . . . . 3-8
   3.4 Primer on Discriminant Analysis . . . . . . . . . . . . . . 3-10

1.0 INTRODUCTION

This document describes the development and testing of the X-ray Enhanced Neutron Interrogation System (XENIS) for explosives detection under FAA contract DTFA03-85-C-00033. This was Phase II of the project; the Phase I report ("Final Report, New Detections Concepts," SAIC Report #87-1055, April 17, 1987) covered experiments and calculations done to test the feasibility of this and other techniques and others. The goal of this phase was to construct an instrument which could be tested at airports in conjunction with the Thermal Neutron Activation (TNA) analysis systems developed under separate contracts. The data base, which was gathered, was to be analyzed to estimate the performance of a combined TNA and X-ray system. It was possible, however, to accelerate the work and actually have a combined system (with an on-line decision algorithm) for the final airport test. After the test, performance of the combined system was reanalyzed and shown to be equal, under certain conditions, to the goals established in Phase I (see Table 1.1), under certain conditions. The data base acquired in these tests is a very valuable one for FAA research and development purposes; it is already being used by at least one other FAA contractor in the development of enhanced security systems.

1.1 General

About two million pieces of luggage are checked or carried onto aircraft each day in the U.S. X-ray scanners, manned by trained operators, are used to check carry on bags, and a variety of automatic explosive detection systems (EDS) for checked baggage are under development by the FAA. Of these EDS's, those using thermal neutron activation (TNA) show the most promise, and are the subject of development by the FAA. However, these TNA systems have (approximately) a 3-9% false alarm rate (depending on baggage distribution), which will result in more than 60,000 suspect pieces per day being stopped to find only a few explosives in a year. In addition, there are some explosives configurations which are difficult to detect with TNA. While it is impossible to get any detection system to the point where it cannot be defeated by a knowledgeable and determined opponent, it can and should be made as difficult as possible. This research program was to Table 1.1

FAA Threat Detection Goals

|  | Checked Baggage and Air Cargo | % Weighting Factor |
|---|---|---|
| Dynamite Granular 40 percent | 4 lbs. | 20 |
| C-4 (Military Spec.) | 2.5 lbs. | 20 |
| Water Gel/Slurry/Emulsions NH4 NO3 (Ammonium Nitrate) | 4 lbs. | 40 |
| Sheet Explosive RDX/PETN (Based) 1/4" or thicker | 2.5 lbs. | 20 |

Processing Rate: 10 units per minute
Detection: 95 percent
False Alarm: 1 percent

CARRY-ON BAGGAGE AND ON PASSENGERS*

A.
| | | |
|---|---|---|
| Dynamite Granular 40 percent | 0.5 lbs. | 20 |
| C-4 (Military Spec.) | 0.5 lbs. | 20 |
| Water Gel/Slurry Emulsions NH4 NO3 (Ammonium Nitrate) | 0.5 lbs. | 20 |
| Sheet Explosive RDX/PETN (Based) 1/4" or thicker | 0.5 lbs. | 20 |
| Smokeless Powder (Double Based) | 0.5 lbs. | 20 |

Processing Rate: 10 units per minute
Detection: 95 percent
False Alarm: 2 percent B.
| | | |
|---|---|---|
| Black Powder | 0.5 lbs. | 20 |
| Smokeless Powder (Single Based) | 0.5 lbs. | 20 |
| Gasoline | 8 fl. oz. | 60 |

Processing Rate: 10 units per minute
Detection: 80 percent
False Alarm: 20 percent

* Under one layer of clothing. XENIS testing did not address carry-on baggage or passengers.

Container: For gasoline 12 oz. plastic bottle 1-2 investigate improvements to the basic EDS's which should greatly decrease their false alarm rate and increase their robustness to (simple) techniques for "hiding" explosives.

1.2 General Philosophy - The Multi-Mode Approach

1.2.1 Introduction

To date, a comprehensive solution that fulfills all the FAA's technical and operational criteria has not been found. Experience and careful analysis of the various technical approaches have, however, provided more insight into the difficulties of the problem. It is apparent that the determination of only one physical parameter characteristic of explosives has been and most likely will continue to be insufficient. To approach unequivocal detection with a minimum of false alarms, a determinant of density, full or partial elemental composition (of which nitrogen is of paramount importance), and general information on size and shape will be required. In particular, the accurate determination of nitrogen density is necessary; this is the function of the TNA. Beyond that, it is desired to have a measurement technique where the errors (misclassifications of safe or dangerous bags) are due to conditions totally unrelated to the sources of error for the primary technique; mathematically, the two techniques should be orthogonal.

The present approach in the development of Enhanced Explosives Detection System is based on this premise, namely, to identify as many features of the explosive material as possible. However, the complexity of the system or subsystem that gives the added information must be gauged against the value of that information. Not considering this would make the final system unreasonably complex, less than reliable and costly, violating important operational requirements. The technique used here is a multi-sensor or multi-mode system. Each sensor in the system does what it does best and is not pushed beyond its natural limits. The information from all sensors and any available *a priori* information are combined in mathematical and logically proper ways to yield the most correct result. Another significant attribute of the information fusion concept of multi-sensor is its great flexibility and versatility. Today's design does not preclude tomorrow's breakthroughs (chemical sniffer, etc.) or changes, e.g., adding more sensors or deleting old ones.

1.2.2 Selection of Modalities

The first and the foremost signature of explosives is the high content of nitrogen. Hence, the basic mode of the enhanced EDS should be to have as high a sensitivity to nitrogen as possible. This entails the highest possible count-rate due to nitrogen with as low a background as possible. Thermal neutron prompt activation of nitrogen certainly is the means to achieve the highest total sensitivity to nitrogen. High nitrogen related gamma count-rate in a properly designed detector array and with a suitable reconstruction algorithm can yield a coarse 2D or 3D image of the nitrogen bearing material. While this information is extremely useful (giving as it does a measure of nitrogen density), it is inherently coarse because of the practical sizes of the gamma detectors and the large statistical fluctuations in counts accumulated in individual detectors. The two TNA based systems constructed at SAIC Santa Clara have an improved design, a high nitrogen gamma count rate, and coarse imaging capabilities, and thus form the first instrument mode in the combined system.

The Phase I study showed that the next most useful mode would be to improve the spatial resolution of the nitrogen image (and thus improve the measurement of nitrogen density) by correlation with a high-resolution density image.[1] The most efficient technique for obtaining a high resolution, two dimensional density image of an object is X-ray radiography. The resolution and precision that such well accepted and tested systems can provide is far beyond what neutron based systems can provide.

---

[1] Another mode which rated quite high in that study (although technically riskier) was the use of Fast Neutron Activation Analysis to measure the oxygen density distribution in luggage. Development of this technique is being done under a separate FAA contract.

The coarse (but very nitrogen specific) image, the best that can be obtained with the XENIS using the appropriate reconstruction algorithm (see Appendix A) is then correlated with the high resolution (but non-nitrogen specific) image delivered by the X-Radiography system. Thus the most prominent attributes of the two modalities, namely, high specificity to nitrogen in the TNA-EDS and high spatial resolution in X-ray, are merged together in an objective way to generate a much more meaningful image of nitrogen bearing materials.

The combination of gamma and X-ray imaging make possible some things that neither alone can give. As an example, if an explosive is detected in on-line operation, the combined image can be presented to the personnel responsible for removing it. The use of the gamma ray 'coloring' to pick the explosive out of the X-ray image should greatly improve the ability of an expert to analyze its construction. The form of the explosive will also be determinable, as it is currently legal to ship explosives in the form of ammunition (if declared) in amounts greater than the threshold; the X-radiography system allows checking of the bag to confirm that that is the way the explosives are being shipped. Automating the pattern recognition process is the subject of current research at a number of institutions; however, using the gamma ray 'coloring' to focus this software on the patterns of importance could simplify this software considerably.

1.3  Scope of Report

This report covers the engineering development of the XENIS system, specifically, the X-ray system and associated image processing equipment. This system was an add-on to the TNA unit developed under a separate program. Results in this report are given relative to the TNA system, so a XENIS Probability of False Alarm of 50% means that only 40% of the TNA false alarms are cleared by the additional information from the X-ray. The design of the system is described in Section 2, with the theory of operation summarized in Section 3. The field tests are described in Section 4. The post-test analysis is reported in Section 5. There is a glossary after 1-5

Section 6, the Summary, for easy reference to some of the terms in the report. The detailed hardware and software documentation are contained in separate documents.

2.0 DESCRIPTION OF MACHINE

The XENIS system as a whole is comprised of equal parts hardware and software. By using off-the-shelf components, most of the effort during the project was able to be directed at software and decision development. The hardware included has been widely used and is commercially available, a critical factor given the XENIS program schedule. The code which runs XENIS, however, is a custom piece of software and, in conjunction with the TNA, makes this system unique.

2.1 Mechanical Description

The XENIS system is built around three main components: a dual-view X-ray scanner, a microcomputer system, and a relay controller. The X-ray scanner, shown in Figure 2.1 is an Astrophysics Linescan System Five, and provides two orthogonal images of each item scanned. The X-ray system uses two 160 KeV X-ray generators and their power supplies, two linear detector arrays having 12 photo-diodes per inch, two display monitors, and a conveyor system. One set of these electronics provides an image taken vertically through the article being scanned (top view), while the other set provides an image taken horizontally through the same item (side view). The two X-ray generators and detector arrays are offset from each other by 3.5 inches along the axis of motion of the conveyor belt to prevent cross-talk. Each of the 512 x 480 pixel X-ray projections are simultaneously displayed side by side as each article is scanned.

The conveyor system consists of the conveyor belt, which is a standard part of the Astrophysics System Five, and a pneumatically actuated bag pusher that was designed and built for the XENIS system. The pusher ensures the proper timing and spatial registration of bags received from the TNA system. The bag pusher is a table that is attached to the entrance-end of the Astrophysics' conveyor assembly. Limit switches, pneumatic actuators and valves, and air-filtering components are mounted underneath the pusher table. Figure 2.2 is a schematic of the workings of the pusher table (PT). A small air compressor maintains pneumatic pressure. When the XENIS system

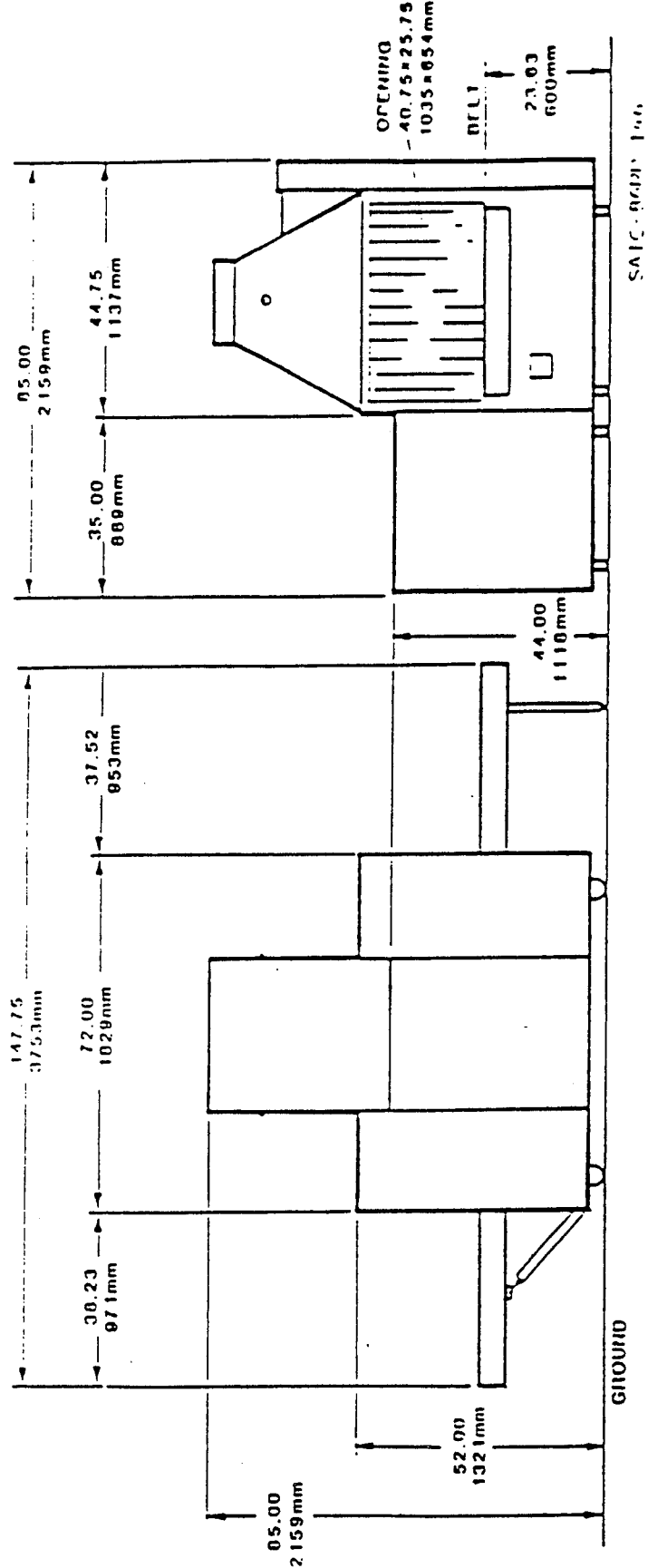
Figure 2.1 Modified Astrophysics Research System 5 Scanner

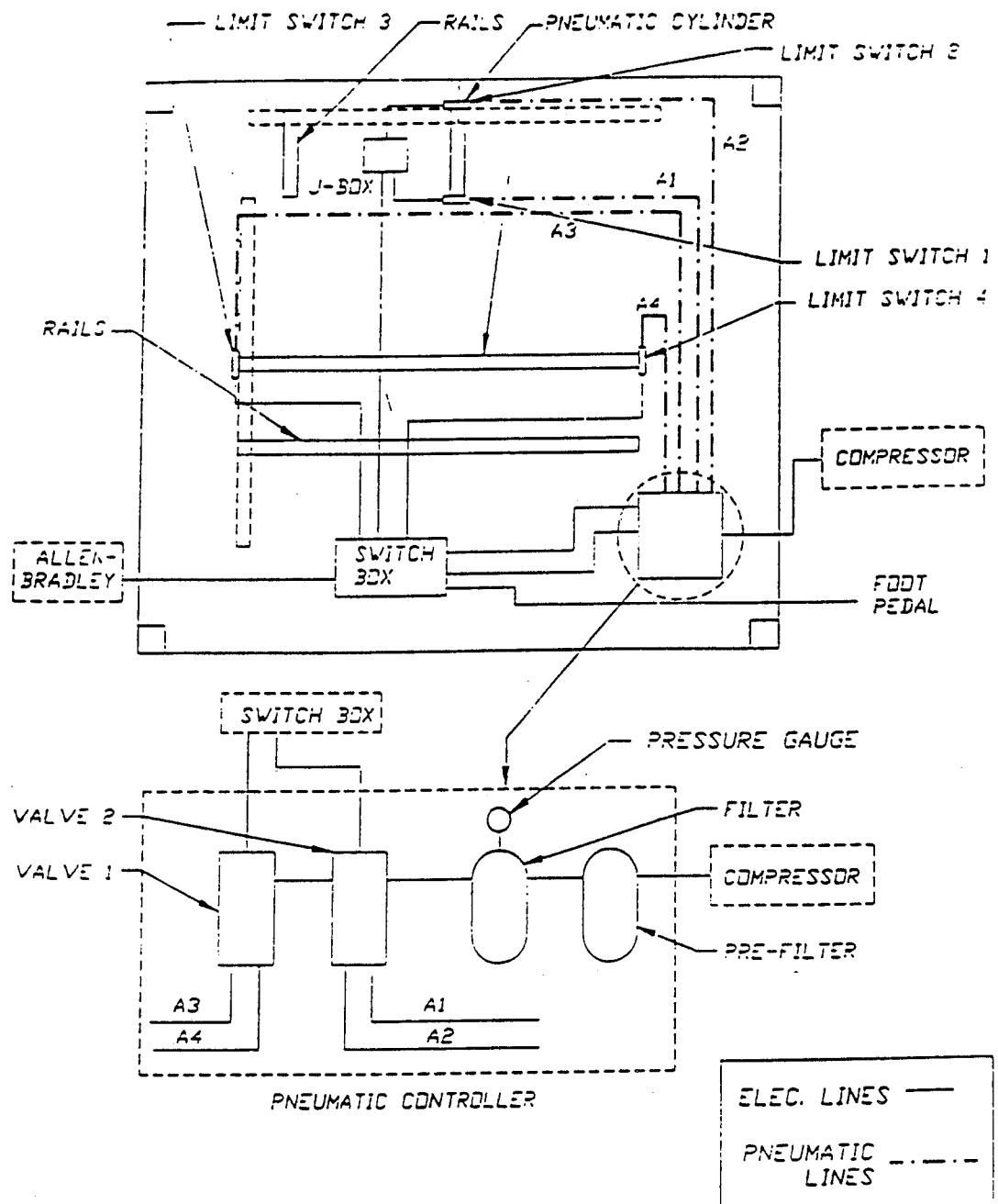
Figure 2.2 Pusher-Table Schematic is ready to process a new bag, the pneumatic cylinders are cycled in sequence. One cylinder actuates a sliding panel from the back side of the machine. This orients the bag correctly. The second cylinder moves the other sliding panel, the end-pusher, which pushes the bag onto the conveyor.

The computer system being used is enclosed in an enclosure separate from the X-ray system, and is built around three primary components: a Digital Equipment Corporation (DEC) MicroVax II, a Recognition Concepts Incorporated (RCI) image processor, and an Optical Storage International (OSI) optical disk. The MicroVax is used for data acquisition, process control, and both on and off-line analysis of data. During on-line operation, information is transferred between the TNA system's MicroVax and the XENIS MicroVax via DECnet, which is a serial link between the two computers. The XENIS MicroVax has two 70 megabyte (MB) hard discs for data and program storage as well as 10 MB of memory. The MicroVax takes the place of the PDP 11/73 that was initially used in the XENIS system, but which threatened to stall development of the advanced imaging and decision software due to the constraint of having to work within its 64 K bytes of memory.

The OSI optical disc drive adds an additional 2 gigabytes of memory per optical disc. Optical discs are used primarily for storage of X-ray images, which require 1/2 MB each, but they are also used for archiving of TNA data. In addition to having the capacity to store up to four thousand two view X-ray images per optical disc, the optical disc has the advantage of allowing rapid and reliable random access to all of the data that has been collected.

A Recognition Concepts Incorporated (RCI) image processor is used to obtain the correlated image from the nitrogen-distribution and X-ray projections. The RCI provides eight 8-bit 512 x 512 image buffers for image processing. Pairs of image buffers can be combined to allow 16-bit frame operations. Accompanying the RCI is a Theoretical Applications Unlimited (TAU) Corporation Real-Time Image Processing Software (RTIPS) library. This library contains the basic software tools necessary to meet the image-processing requirements of the XENIS system. Included in the RTIPS library is a generalized arithmetic logic utility, pipeline utilities, edge-identification operators, and I/O utilities. These software utilities are implemented both interactively and non-interactively via programs which are written and executed on the MicroVax. X-ray images are acquired by the RCI via direct coaxial cable connections to the display monitors of the Astrophysics System Five. A 1024 x 1024 pixel Sony television monitor is used to display the contents of the various image buffers of the RCI, and to examine the results of the operations that are performed on the images.

Upper-level control of the sequencing and timing of the mechanisms used in the acquisition of X-ray images is provided by an Allen-Bradley PLC-2 relay controller. The Allen-Bradley (AB) controller uses relay logic to schedule the activation of the pusher-table, the X-ray scanner, the analysis software, and a video switcher, which is a relay mechanism that switches the input to the RCI between the two X-ray display monitors. The Allen-Bradley controller is housed in a dust-free enclosure that has been mounted on the Astrophysics X-ray scanner. It is programmed through a portable terminal which may also be used to monitor program execution. Once programmed, the battery-powered memory can store the program for several years before the lithium batteries need to be replaced. The operation of the Allen-Bradley is discussed in greater detail under Section 2.2, Description of Electrical Requirements and Electronic Interfaces Between System Components and in Appendix D.

2.2  Description of Electrical Requirements and Electronic Interfaces Between System Components The XENIS system requires two 120 VAC, 60 Hz, 20 A power circuits. Two circuits are necessary in order to provide isolation between the computer system and the compressor. This isolation is necessary because the compressor may cause power transients that could crash the computer and interfere with the images produced by the X-ray scanner. The only other power requirement for XENIS is that the X-ray scanner and the RCI image processor must be on the same circuit. This is necessary to maintain synchronization between the two machines, which allows the X-ray images to 2-5 be properly transferred to the image processor. In addition to these power requirements, a power conditioner has been installed in the electronics enclosure to provide additional protection to the computer, image processor, and display monitor against transients and overloads.

The upper-level electronic interface of XENIS' components with each other is handled through connections to the Allen-Bradley relay controller. These interconnections are shown schematically in Figure 2.3 below, where dashed lines indicate connections with the Allen-Bradley, and the solid lines represent other signal connections.

The link between the TNA system's MicroVax and the XENIS MicroVax is a DECnet serial connection through a standard RS-232 line. When a data set has been sent to the XENIS MicroVax from the TNA system, a relay in the Allen-Bradley controller is set, indicating that the system is ready to acquire an X-ray image.

The Allen-Bradley asserts control over the operation of the X-ray scanner through connections to the system control card on the Astrophysics unit. When the bag comes out of the TNA system, it is placed on the pusher table and the baggage-handler presses a foot switch to signal that the bag is present. If the controller has received the signal indicating that the image processor is ready to acquire a new X-ray image and that the conveyor is running, then the controller signals the pusher table to push the new bag onto the conveyor. Once on the conveyor, the bag moves through the X-ray cavity, and the X-ray projections are generated and displayed on the System Five monitors.

After the X-ray projections have been generated, the Allen-Bradley signals the MicroVax to load the vertical X-ray projection into the image processor. This image is transferred directly to the RCI from the Astrophysics display monitor via a coaxial cable. When acquisition of the vertical X-ray projection has been completed, the Allen-Bradley switches the image-processor input from the vertical-projection display monitor to the horizontal-projection display monitor. This is done through the video switcher.

2-6

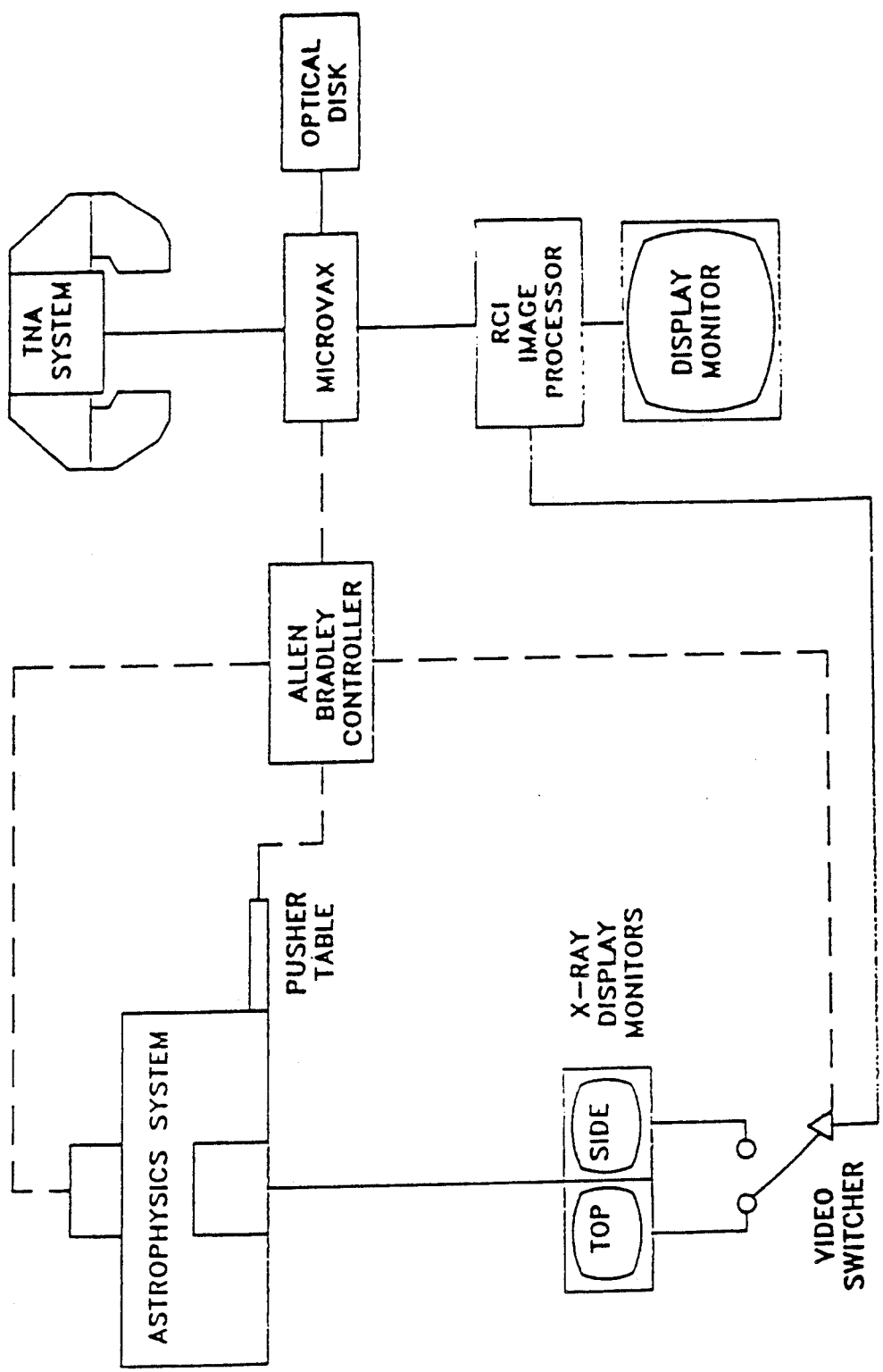
Figure 2.3 XENIS System

The video switcher is a simple relay switch which allows the connection to the image processor's input cable to be quickly switched from the vertical X-ray projection to the horizontal X-ray projection and back.

Once both images have been acquired by the image processor, the controller is signaled that the system is ready to acquire a new X-ray image and that the MicroVax and RCI image processor can begin with the correlation and analysis procedures. Figure 2.4 is a flow-control diagram for the operation of XENIS. A ladder diagram of the relay logic for the Allen-Bradley controller is provided in the Appendices.

2.3 Software Design

The software for the X-ray Enhanced Neutron Interrogation System (XENIS) consists of three tasks:

- Data Acquisition
- Data Analysis
- Decision Analysis

2.3.1 Data Acquisition

The main purpose of the data acquisition module is to acquire raw data from the X-ray scanner and TNA information from the TNA system. The data acquisition module is subdivided into two smaller tasks:

i. X-ray Image Acquisition
ii. TNA Image Acquisition

The X-ray image acquisition system uses a modified Astrophysics Linescan System Five's electronics and display package. The data are recorded and corrected line by line. The correction includes both gain and zero level, and is updated automatically between bags (for more information, refer to Astrophysics System 5 documentation). The corrected data is scrolled into two video memories where they can be observed by the operator. At the end

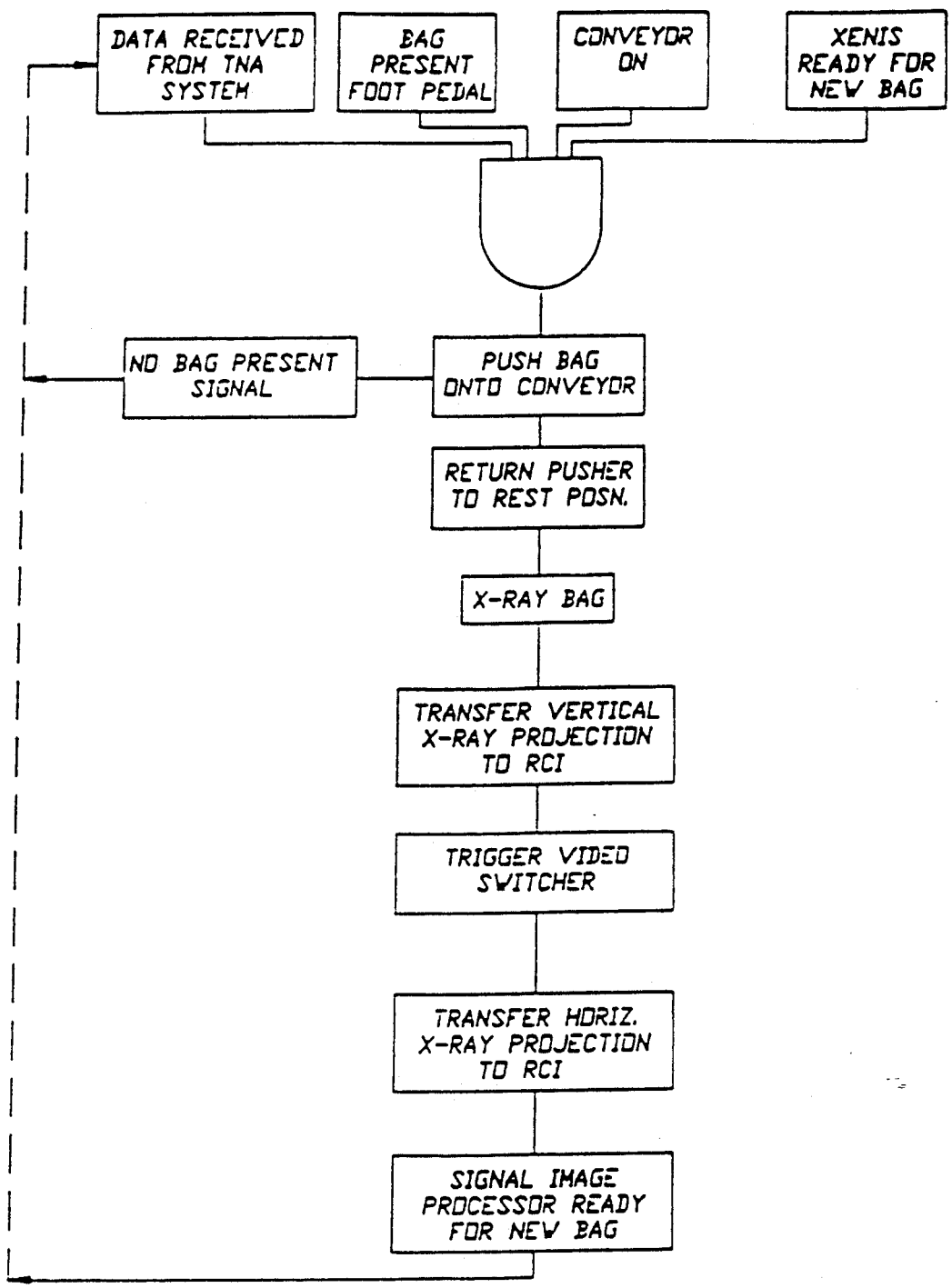
Figure 2.4 XENIS Flow Control of each complete image, the data is read rapidly into two image processor (RCI) buffer memories which is attached to Digital Equipment Company MicroVax II computer (for more information, refer to section 2.2).

TNA image acquisition is done via a dedicated RS-232 serial line communication between the TNA's MicroVax II and XENIS's MicroVax II. The TNA system produces a set of data for each bag. This data set consists of the bag identifier, size array (a set of light curtain measurements taken at various positions, which gives the size and orientation of the bag with 0.75 inch resolution), bag length, weight, and the reduced or above-background nitrogen image as a function of bag position. Transmission and reception of the information packet are handled by processes separate from the main code (QUEFIL).

The main purpose of the QUEFIL program is to accept TNA image data from the TNA's MicroVax II and process it according to the control code sent with the data. This control code represents the place in the queue where the image resides. Normally the data is placed into a FIFO (First In First Out) queue. The analysis module can then retrieve data from this queue as needed.

2.2.2 Data Analysis

The data analysis module is a section of the code that processes both X-ray and TNA images to produce discriminant values for the decision analysis module. The data analysis module can be further subdivided into four smaller tasks:

i. Projection
ii. Correlation
iii. Edge enhancement
iv. Agglomerization

The purpose of the projection module is to obtain projections of the nitrogen distribution in the TNA cavity taken from viewing aspects similar to those that produced the X-ray projections. Two projection algorithms have been developed, both of which produce projections of the nitrogen distribution into orthogonal planes corresponding to the X-ray projection planes. One projection algorithm, known as the straight-projection algorithm (STRAT_PROJ), produces a projection along parallel rays that are perpendicular to the plane of projection. The other algorithm, known as warped-projection algorithm (using the routines PROSUM and PROMAX) produces an image that corresponds more closely to the fan-beam projection that is actually produced by the X-ray system. Both modules allow a vector of weighting factors to be applied to each voxel intercepted by each ray of the projection. The PROMAX routine assigns the weight 1 to the maximum intensity intercepted voxel and 0 to all other intercepted voxels. PROSUM applies equal weighting to each intercepted voxel.

Another projection module, SETPRJ, was developed at the beginning of the XENIS project, and was written entirely in FORTRAN to produce a mathematically rigorous projection. In addition, it was designed to compensate for any difference in orientation of a bag between the TNA cavity and the XENIS cavity. The straight- and warped-projection algorithms are less mathematically rigorous and do not compensate for bag misorientation, but this has no substantial affect on the system's performance because of the low resolution of the TNA system, and because the pusher table ensures that bags are properly aligned in the XENIS cavity. The straight- and warped-projection modules have the advantage of allowing variable weighting on the maximum projected voxel intensity, while the straight-projection module has the advantage of greater speed and simplicity.

The straight-projection module was developed as an easily implemented algorithm that could be used while developing the more complicated fan-beam projection code. The straight-projection algorithm is written entirely in FORTRAN, and includes no geometrical consideration of the actual fan-beam projection geometry of the X-ray system. STRAT_PROJ projects the nitrogen distribution by simply summing the voxel intensities along rays perpendicular to the plane of projection, as shown in Figure 2.5.

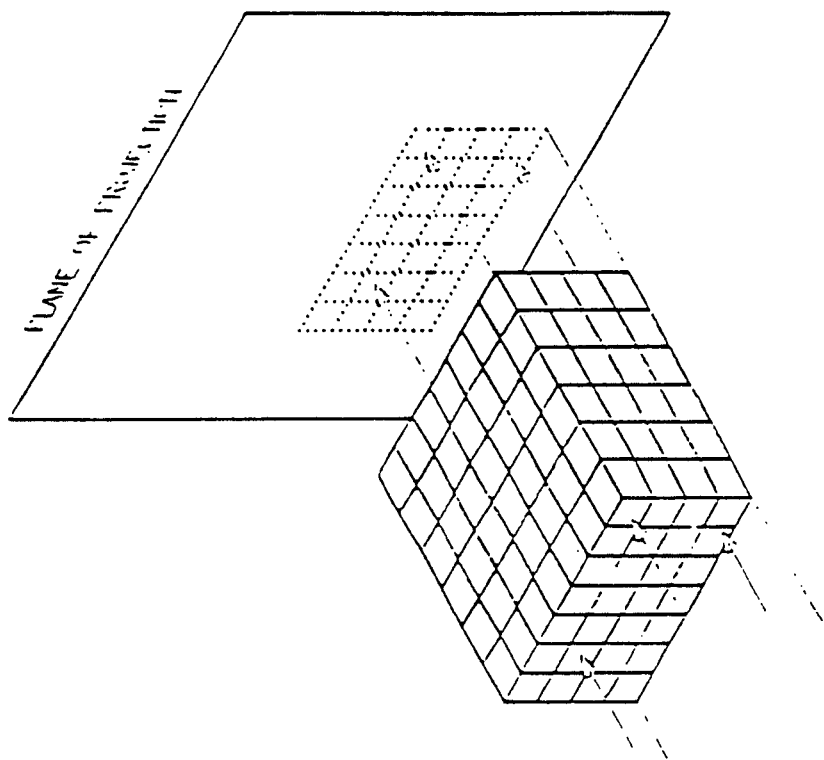
Figure 2.5 Straight Projection Geometry

The warped-projection algorithm is based on two routines, one of which projects the maximum voxel intensity encountered along a ray path (PROMAX), and another which projects the sum of the voxel intensities along each ray (PROSUM). In PROSUM, the final warped and weighted image is obtained by multiplying the maximum voxel intensity by the desired weighting factor, adding the result to the average voxel intensity projection, and normalizing to the correct intensity range. Thus, the procedure results in a weighted average between the maximum penetrated voxel intensity and the average penetrated voxel intensity.

PROMAX and PROSUM are identical, with the exception that PROMAX retains only the maximum intensity along the projection path, while PROSUM maintains a running total of the voxel intensities along each ray. Both routines use an assembly-language core routine that operates in the image processor and which is called by a FORTRAN driver. The warping algorithm used by each routine is shown schematically in Figure 2.6. The algorithm collapses each layer of voxels into a plane. The magnification at each layer is determined from the dimensions of the X-ray cavity, and by using simple geometric relationships. Each layer is stretched, or warped, by the appropriate magnification factor in the dimension transverse to the direction of motion. The desired result is obtained by projecting along parallel rays through the warped layers.

The warped-projection algorithm was developed to determine whether a projection routine that accounted approximately for the magnification effects in the X-ray system would significantly improve the performance of the XENIS system. Upon implementing the warped projection, no significant objective improvement was observed. This may be due to the coarse TNA grid, the low magnifications encountered with typical bag dimensions, and the uncertainties involved in the TNA reconstruction. In addition, the final algorithm, which included warping and linear weighting on the maximum voxel intensity, required approximately 1.6 seconds per projection, whereas the straight-projection algorithm required much less than a second. Because it was felt that this overhead of time was unacceptable in view of the limited 2-13

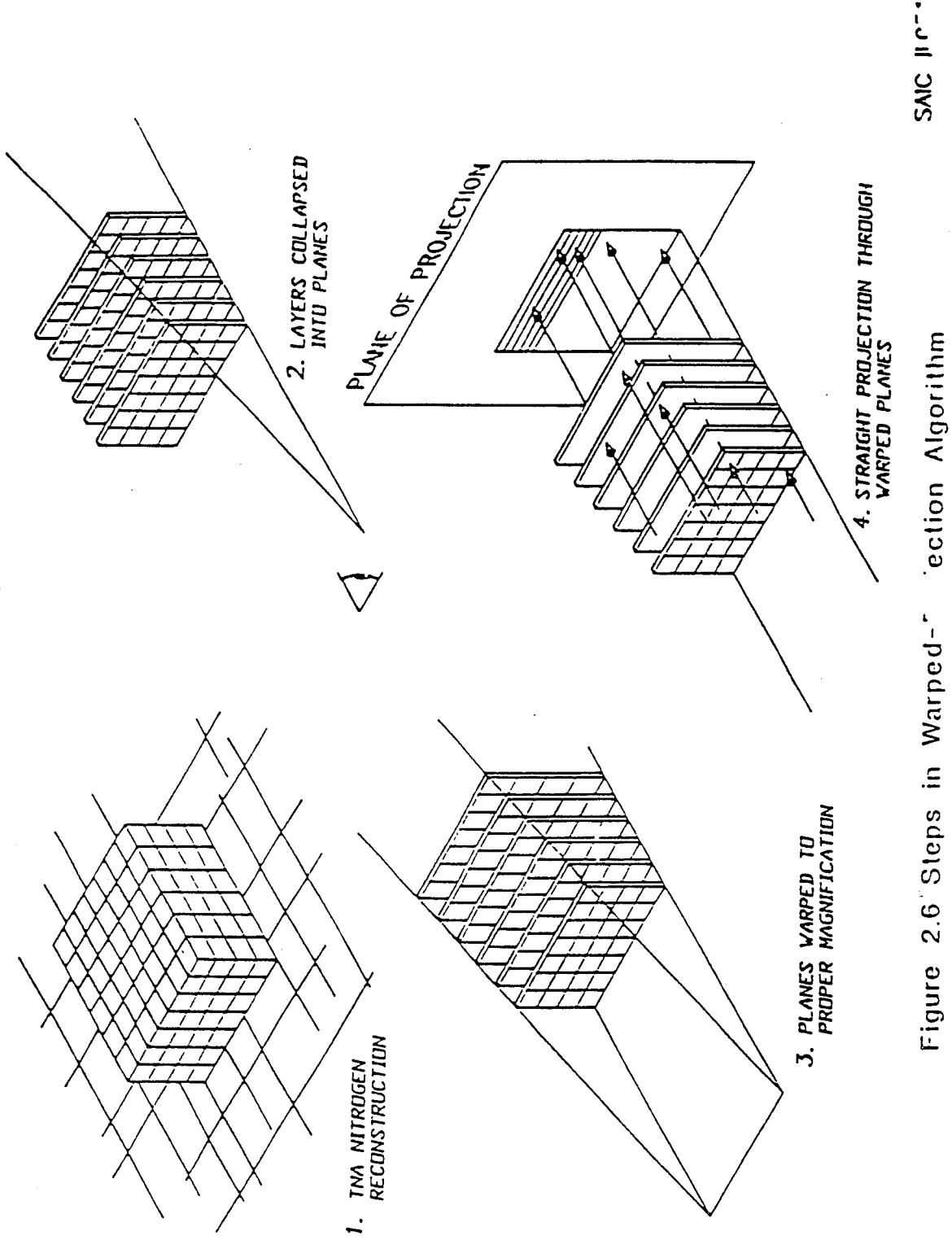
Figure 2.6 Steps in Warped-Projection Algorithm advantages of the warped projection, the straight projection algorithm has been used exclusively in the analyses that have been performed.

The edge enhancement routine was developed to eliminate narrow, high density regions which arose from the correlation and agglomeration. These narrow high density regions caused connections between threat blobs and non-threat blobs in the rest of the suitcase. This edge enhancement or skeletonization algorithm is as follows:

- Identify the edges of objects in the correlated image in a image
- Enhance these edges to make them more prominent
- Create an edge image comprised solely of the enhanced edges.
- Subtract the 'edge' image from the original image yielding an 'edge subtracted' image.

The edges are found by applying the Sobel edge operator to an image (for more information, refer to TAU software documentation).

Agglomeration, or "blobizing" is the process of identifying highly correlated objects within the correlated image, and is performed by the assembly-code program FVC. After the correlation convolution has been performed, a binary image is formed from the correlated image. Pixels having intensity greater than the threshold that had been chosen are mapped to an intensity of 255 (white), while pixels below the threshold are mapped to 0 (black). The program FVC identifies contiguous regions of pixels having an intensity of 255. Working from the bottom-left corner of a region of interest, FVC looks for pixels having an intensity of 255. Upon finding a white pixel, FVC performs tests to determine whether any adjacent pixels are also white. This contiguity test is repeated for each adjacent white pixel until no new pixels are found. Objects are identified in a labelled image by mapping each set of contiguous pixels to a different intensity level. In other words, the first object to be identified will be closest to the lower left corner of the region of interest, and will be assigned an intensity of 1 in the labelled image. The next object identified will be assigned an intensity level of 2, and so on. Because the labelled image is eight bits deep, this labelling scheme is capable of identifying up to 255 objects.

Once all of the highly correlated objects have been identified, FVC makes one more pass over the binary image, this time to identify the boundaries of the objects that have been found. To do this, FVC identifies white pixels that have neighboring black pixels. Each white pixel that is found to have a neighboring black pixel is mapped to an overlay buffer, where the outlines of all of the objects are displayed in green.

2.3.3 Decision Analysis

The decision analysis module is responsible for determining whether or not a suitcase contains an explosive. The current decision algorithm is based on the discriminant analysis as described in Section 3.4. The decision analysis can be divided into two algorithms for bulk and sheet explosives.

The bulk algorithm is based on agglomeration techniques which take the correlated image and locates objects in the suitcase or "blobs" that are above a set threshold. The blobs are then analyzed to produce discriminant features for the final decision. Currently this algorithm is used only on the "top view" of the suitcase. Although it is possible to apply this algorithm to the sideview; however, in the test, the simulant was always placed outside of the suitcase and thus shows up too clear in the side view.

The sheet algorithm is activated when the TNA system signals a possible presence of a sheet explosive. The sheet algorithm makes use of both side and top views of the X-ray image. The top view is pertinent for detecting sheet explosive on the side and side view pertinent for sheet explosive on top or bottom. The discriminant features for the sheet algorithm is produced by evaluating how attenuated the X-ray beam is along the edges, and evaluating the correlated image. Then final decision is made based on these discriminant features.

3.0 THEORY OF OPERATION

The theory behind the XENIS system is to combine two distinct pieces of information such that the resulting product is better than if both were used individually. Combining nuclear physics and basic X-ray technology has produced a system that detects explosives with a high degree of precision. The method used and the origin of each of these pieces of information is discussed below.

3.1 Background for the Thermal Neutron Activation (TNA) Technique

There are two sources for the information that comprise the input to the XENIS system. One of these is the data from the Cf EDS system. The other is the X-ray images supplied by the Astrophysics System Five. The XENIS system combines these two pieces of information into a "nitrogen - physical density" image. Since explosive material is generally high in both nitrogen density and in physical density, this combined image is a better predictor of the presence of an explosive than either image alone. In addition, if an explosive is present, the correlation process will improve the spatial resolution of the nitrogen image. Thus a suitcase that may appear to have sufficient nitrogen density to be a threat to the TNA system can be more accurately examined with the XENIS system; if there is insufficient mass present to constitute a threat, then the TNA alarm was false.

The data from the TNA system is comprised of information on how much nitrogen the bag has and a rough approximation of its location. This nitrogen content information of the suitcase is derived from the basic principles behind the TNA system. The term TNA refers to Thermal Neutron Activation. When a thermal neutron encounters a nucleus of an atom of a given element, one of two things can happen. The neutron can either be absorbed by the nucleus or it may "bounce off." It is the former event which gives rise to the signals in the TNA system. A thermal neutron is one which is at thermal equilibrium with the material (its minimum energy) and consequently has the highest probability of being absorbed by the nucleus of an atom.

3-1

When a nucleus absorbs a neutron, it becomes "activated" and there is a probability that a gamma ray of an energy particular to the absorbing element will be given off. Thus the term "activation " refers to that occasion where the nucleus captures a neutron and emits a gamma ray. For nitrogen the gamma ray of interest has an energy of 10.8 MeV. These gamma rays are detected in an array of detectors; see the Cf Final Report for a description of that system. It is this signal which is used to reconstruct the TNA image.

The three dimensional TNA image is transmitted via an RS232 serial link between the two Microvax's in the form of a 2D matrix in a data file. Figure 3.1 represents a typical TNA image file. The twenty decision parameters listed at the beginning of the file represent twenty values from the TNA decision algorithm that are sent to XENIS and are of potential use to the XENIS decision algorithm. For example, parameter five represents the grams of nitrogen present in the bag, parameters three and four are the TNA system's U12 and U13 respectively. The numbers arranged in the two dimensional array represent normalized nitrogen values on a scale of zero to 255. These numbers when read into the RCI become pixel intensities. The coordinate system is laid out in Figure 3.1 with positive z being the direction of travel for the bag thru the systems. The four x values for each y,z coordinate represent the third dimension of the bag coming out of the page. The value x1 is at the bottom with x2 on top of x1 etc. At the bottom of the file are various physical parameters describing the bag including whether or not it contained a simulant.

3.2 Correlation With X-ray Image

The technique used to create the nitrogen image from the acquired data is the Algebraic Reconstruction Technique (ART) with regularization. The signal from the suitcase can be represented by a vector, S, which is the observed count rate observed in each detector for each time interval as its elements. If there were N detectors and T times of observation, then the first N elements of S are the counts in the detectors for the first time 3-2

```
TAG  :    270
KPOS:      9
NY   :      6
NX   :      4
NZ   :      7

DECISION PARAMETER  1 :      4.0000
DECISION PARAMETER  2 :      2.0000
DECISION PARAMETER  3 :    -18.8961
DECISION PARAMETER  4 :     -3.5786
DECISION PARAMETER  5 :    599.3819
DECISION PARAMETER  6 :   5047.9199
DECISION PARAMETER  7 :      0.0000
DECISION PARAMETER  8 :     60.0000
DECISION PARAMETER  9 :     90.0000
DECISION PARAMETER 10 :    100.0000
DECISION PARAMETER 11 :      0.0000
DECISION PARAMETER 12 :      0.0000
DECISION PARAMETER 13 :      0.0000
DECISION PARAMETER 14 :      0.0000
DECISION PARAMETER 15 :      0.0000
DECISION PARAMETER 16 :      0.0000
DECISION PARAMETER 17 :      0.0000
DECISION PARAMETER 18 :      0.0000
DECISION PARAMETER 19 :      0.0000
DECISION PARAMETER 20 :      0.0000
DISC_VALUE :   0.0000 DECISION :    1

TNA IMAGE
```

|     |     |     |     |     |     |
| --- | --- | --- | --- | --- | --- |
| 131 x 4 | 118 | 33  | 30  | 41  | 40  |
| 43 x 3  | 56  | 37  | 47  | 57  | 46  |
| 45 x 2  | 41  | 45  | 68  | 68  | 18  |
| 72 x 1  | 34  | 40  | 89  | 104 | 51  |
|         |     |     |     |     |     |
| 173     | 64  | 14  | 36  | 57  | 80  |
| 49      | 50  | 45  | 53  | 54  | 60  |
| 32      | 50  | 60  | 59  | 55  | 29  |
| 79      | 80  | 84  | 53  | 67  | 65  |
|         |     |     |     |     |     |
| 143     | 72  | 88  | 139 | 65  | 49  |
| 54      | 46  | 60  | 80  | 61  | 57  |
| 30      | 37  | 51  | 61  | 58  | 58  |
| 34      | 32  | 43  | 47  | 59  | 81  |
|         |     |     |     |     |     |
| 91      | 50  | 74  | 109 | 6   | 28  |
| 60      | 57  | 81  | 99  | 66  | 87  |
| 54      | 53  | 76  | 93  | 75  | 86  |
| 74      | 51  | 72  | 99  | 47  | 57  |

Figure 3.1 Sample TNA Image File

| 79 | | | 80 | | |
|---|---|---|---|---|---|
| 109 | 22 | 63 | 109 | 6 | 43 |
| 43 | 24 | 47 | 70 | 44 | 81 |
| 26 | 30 | 46 | 68 | 53 | 73 |
| 67 | 50 | 63 | 94 | 39 | 42 |
| 111 | 17 | 73 | 113 | 23 | 37 |
| 46 | 33 | 62 | 84 | 52 | 48 |
| 17 | 28 | 43 | 73 | 58 | 48 |
| 99 | 45 | 25 | 85 | 55 | 36 |
| 95 | 26 | 77 | 69 | 8 | 36 |
| 42 | 27 | 59 | 73 | 45 | 42 |
| 0 | 18 | 34 | 72 | 60 | 22 |
| 49 | 44 | 0 | 87 | 63 | 11 |

```
BAG_WIDTH   :    20.25
BAG_HEIGHT  :     9.50
BAG_LENGTH  :    26.24
BAG_WEIGHT  :    28.62
BAG_ANGLE   :  5047.49
BAG_OFFSET  :     0.00
BAG_CLASS   :        4
X-RAY EXT   :     824E
TIME        : 24-AUG-87 14:00
SIM_CODE    :
```

Figure 3.1 (continued)

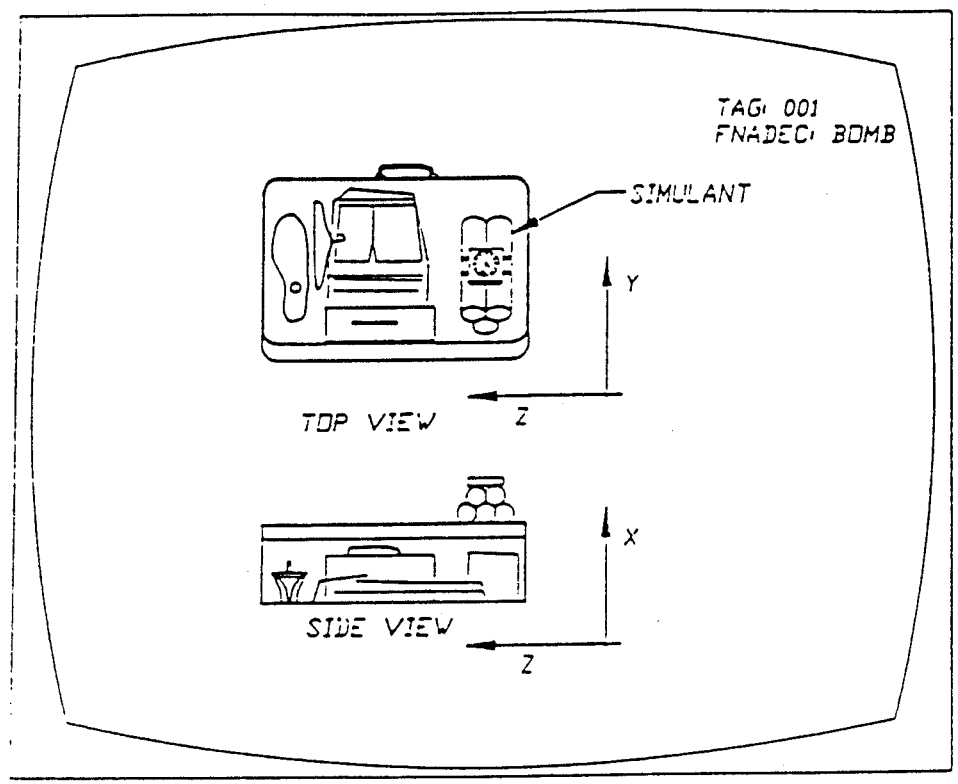
Figure 3.2 Xenis Xray Views and Coordinate System period, the next N are for the second time period, and so on up to the N * T element. Similarly, there is a vector p of nitrogen densities in the cavity. The cavity is divided up into a number of volume elements (voxels) each roughly the size of the detectors, a cube 4 inches on a side. The nitrogen content of each voxel describes the distribution of nitrogen densities to the degree of precision possible with the relatively large detectors used in the system. The voxels are simply numbered sequentially with x varying most rapidly left-to-right, then y varying top-to-bottom and finally z varying least rapidly from the entrance-to-exit of the cavity along the belt. The signal and nitrogen density are related by a transfer matrix W :

$$S = W p \qquad (1)$$

The elements of W can be calculated by the use of the simulation code used in Phase I, or they can be measured by experiments with small amounts of nitrogen in nearly empty containers. In practice, estimation of the forward response matrix was done by use of the simulation code.

The problem in on-line operations is to calculate the value of the vector p from the given measurement of S. Since there are more measurements (elements in S) than there are values to be determined (elements in p), the Algebraic Reconstruction Technique gives the usual least-squares solution:

$$\hat{p} = (W^T W)^{-1} W^T S \qquad (2)$$

Unfortunately, because of the noise present in the system, and the high degree of correlation between the elements of W, the $W^T W$ matrix is ill-conditioned, and its inverse will have both large and small elements in it. As a result, artifacts will appear in the reconstructed image represented by large variations, or alternative high and low nitrogen content in adjacent voxels. To reduce these effects, and increase the stability of the result, a smoothness constraint is added. This technique is known as regularization.[1] In this case, the smoothness constraint added is one that "penalizes" large first derivatives of the nitrogen density, i.e., it tries for a zero first derivative over the entire image. The effect is a uniform background and a smooth transition in the area of high nitrogen content. If the constraint is forced to the extreme, i.e. has a large Lagrangian multiplier, the result will be a uniform image. If K is the matrix operator for the first derivative of the p vector, then equation (2) becomes (by the application of the usual Lagrangian constraints):

$$\hat{p} = [(W^T W + g K^T K)^{-1} W^T] S \qquad (3)$$

In equation (3), g is the "smoothing coefficient;" the larger it is, the smoother the resulting estimate of p will be. This parameter requires adjustment to produce a good reconstruction.

All of the terms in the square bracket in equation (3) are known from the construction of the system; thus, they can be computed in advance of on-line operation and stored as a single matrix. During the on-line operation, it is only necessary to do a single matrix multiplication. This is a substantial number of computations (the matrix in square brackets, the inverse transfer matrix, is 140 by 270 in this application), but feasible in the time available. This reconstruction produces a three dimensional image, where the number in each voxel is linearly related to the amount of nitrogen present in that voxel. A more detailed explanation of the reconstruction algorithm can be found in Appendix A.

To use this nitrogen image it must be "correlated" with the X-ray image. The first step in the correlation process reduces the size of the X-ray images by downsampling of pixels to one compatible with the TNA projections (every other odd pixel is removed three times, for a total reduction of a factor of 8). This image is stored as $S_1$, the high-resolution X-ray data. The next step reduces the resolution of the X-ray images to that of the TNA

---

[1] See, for example, S. Twomey, *Introduction to the mathematics of inversion in remote sensing and indirect measurements*, Elsevier Scientific Publishing Co., 1977.

image using a convolution of the image with a sparse Gaussian kernel. (A sparse kernel is one in which most of the elements are zero. A sparse kernel can give a large area smearing with a limited amount of computer time.) The result of the convolution yields the image $\overline{S_1}$, the X-ray images that would have been obtained if the X-ray system had spatial resolution comparable to the TNA system. The result of the convolution is used to form the images $S_0\overline{S_1}$ and $\overline{S_1}^2$, where $S_0$ is the TNA projection image. Having performed the above on both the top and side view, the results of these image multiplications are shifted and added to form a single image from four sub-images: the top view $S_0\overline{S_1}$ and $\overline{S_1}^2$ and the side view $S_0\overline{S_1}$ and $\overline{S_1}^2$. The next step in the correlation is to form "expectation" values of the product images. This is done by local average convolution. The result of this operation is an 8-bit image, part of which represents $<S_0\overline{S_1}>/<\overline{S_1}^2>$, where < > denotes local area spatial averaging. The final step is to threshold the correlated image to producing a binary image of high nitrogen density and high material density in the object. The binary image can then be analyzed by an agglomerization routine to determine acceptance/rejection criteria. Figure 3.3 shows the flow diagram for the TNA/X-ray correlation analysis.

3.3 Features From TNA Alone

Some of the features used in the XENIS decision algorithm are generated by the TNA EDS. Parameters such as the U12 and U13 generated by the Cf system are used to a small extent by XENIS. With the U12 and U13 values from the TNA it is possible to determine how strongly the Cf system is convinced that a piece of luggage contains a threat. It also indicates what type of explosive (bulk or sheet) is thought to be present. This helps XENIS in that if the Cf system is virtually positive that a bag contains a threat, XENIS will pass on the TNA decision as final. Table 3.1 is a list of the features generated by the TNA system and are used in the XENIS decision algorithm.

3-8

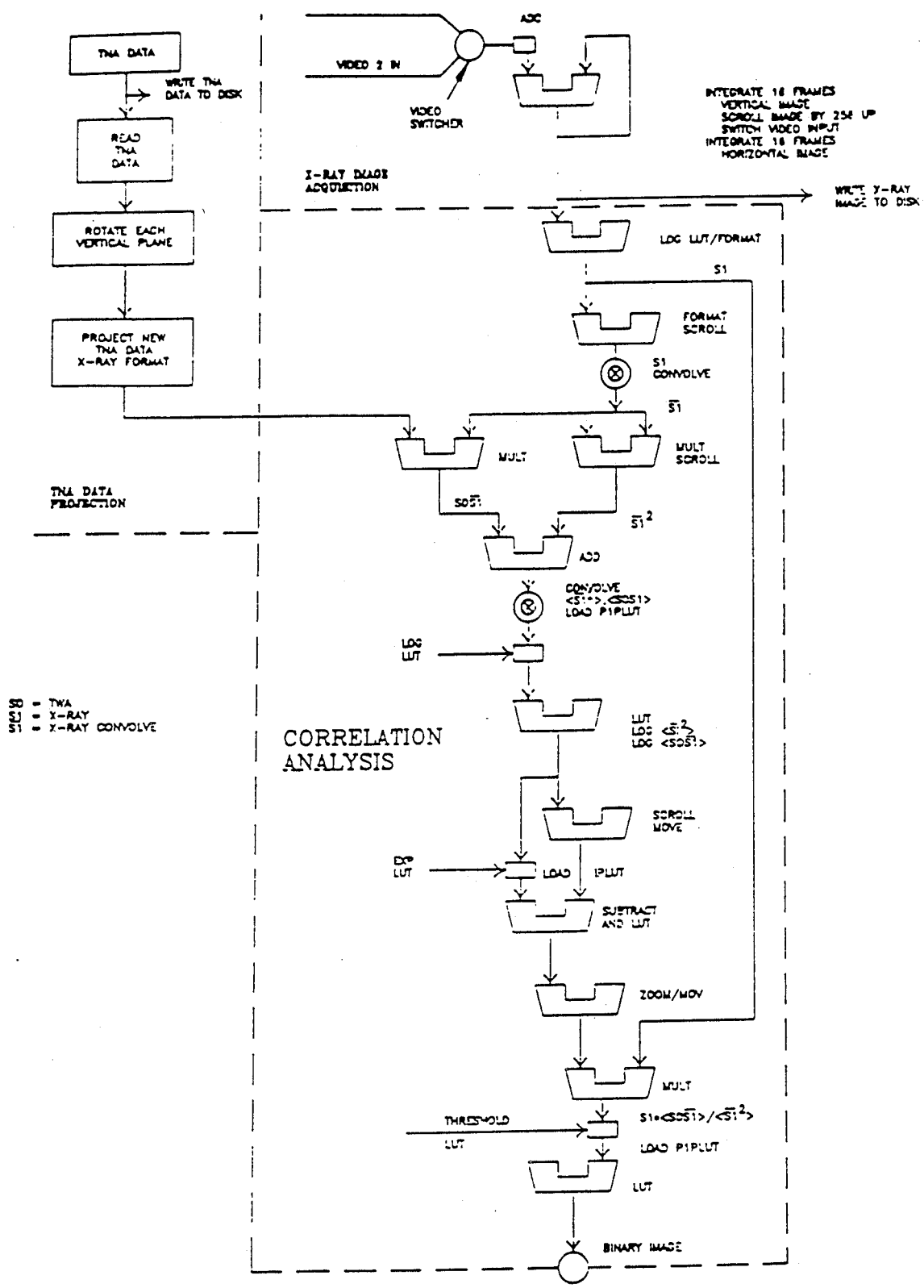
FIGURE 3.3 FLOW DIAGRAM FOR TNA/X-RAY COORELATION ANALYSIS

Table 3.1

TNA Features Used in XENIS Decision

| Feature | Definition |
| --- | --- |
| U12 | Distance of the suitcase measurement from the hyperplane dividing bulk explosives and clean bags as measured in feature space. |
| U13 | Distance of the suitcase measurement from the hyperplane dividing sheet explosives and clean bags as measured in feature space. |
| GNIT | Grams of nitrogen in the suitcase. |
| Volume | Volume of the suitcase in grams/cm3. |

3.4  Primer on Discriminant Analysis

A discriminant function h(x) is some function of the measurement vector x such that h(x) > k (a constant) implies that x is a member of subspace 1 ("bag with threat") and h(x) < k implies that it is a member of subspace 2 ("bag without threat"). In general, a linear function h is used for simplicity; but it is easy to generalize this to a function that is linear in simply-computed subfunctions $f(x) = (f_1(x),......,f_n(x))$. The $f_i(x)$ are variously called discriminating variables or features, and represent such terms as total counts, second moments from the imaging analysis, etc. Generally, these feature variables should be standardized for within-group variance, i.e., normalized.

The most important features that XENIS uses in the threat/no-threat decision come from the correlated image. The above parameters are used merely as an indication of how sure the TNA was about the decision it made, to be compared with the U12 and U13 generated by the XENIS decision. It represents yet another method used to combine the two seperate and distinct pieces of information from each system.

The idea behind the discriminant analysis is that the underlying population of measurements is distributed into two distinct classes (with and without threats). The discriminating variables form a coordinate system in which a hyperplane can be defined which separates the two classes. Two different criteria are commonly used to establish these discriminants. First, the perceptron criteria, which weights the number of points which are misclassified by their "amount" of misclassification. Second, Fischer's criterion detemines the normal to the optimal separating hyperplane for the two subsets.[2] This latter (or a variant of it) is the kind used for this project.

A simple version of this is to collect a series of feature sets $f(x)$ for many bags, assign $y=1$ for cases with bombs, and $y=0$ for cases without, and do a linear regression to get $h(f(x))$. If the variables are properly scaled, then the coefficients reflect how important each feature is in determining the presence of a bomb.

The analysis used in the on-line code is complicated by the fact that it is necessary to detect both sheet and bulk explosives. This is an extension of the usual discriminant analysis to the case where a sample may be drawn from one of three separate populations. From the data set, the mean vectors of each population, $x_0$, $x_1$, and $x_2$, are calculated; the pooled covariance matrix (which is an estimate of the assumed common within-group covariance matrix) $S$ is also calculated. There are six discriminant functions which can be computed:

$$u_{ij}(x) = [x - 0.5(x_i + x_j)]^T S^{-1} (x_i - x_j) \quad i \neq j$$

where $x_i$ is the mean of the ith population, and $u_{ij} = -u_{ji}$. Once these six values (which represent the distance above or below the hyperplane dividing each of the two groups in turn) are computed, an observation is assigned to group i if $u_{ij}$ and $u_{ik}$ (with i, j, and k not equal) are both greater than or

---

[2] See, for example, C. Rao, *Linear Statistical Inference and Its Applications*, 2nd ed., Wiley and Sons, 1973.

equal to zero.[3] For signalling the presence of an explosive, classification of the measurement into either the bulk or sheet explosive group is sufficient; the extra classification has been added because different features are important in detecting sheet explosive.

The above technique is the "three-way" discriminant analysis used in the SFIA-TWA test. Since the distinction between bulk and sheet explosive is relatively unimportant (except in that different sets of features are required in each computation to achieve best performance), it is possible to separate the functions into 2 2-way classifications. One function is used to discriminate between bulk explosive and clean; one is used to discriminate between sheet explosive and clean. Only if both functions say "clean" is the bag considered safe. Some bags will alarm one discriminant or the other; many alarm both.

It is important to watch for falsely good discriminants which may result from unintended patterns in the data. For example, if the explosive simulant is always placed in the center of the suitcase, then the variables which describe the position of the nitrogen counts may seem to be good at detecting bombs. This is why a large number of random bags of data is necessary and why some possibly useful features (such as nitrogen centroid) cannot be used (on-line tests were done by placing the simulated explosive outside the suitcase, as passenger luggage could not be opened).

---

[3] This formula assumes equal weighting for misses on both sides of the plane, which is not strictly true in this case, but has been used for convenience.

Gozani, et al
Docket 47475

MULTI-SENSOR EXPLOSIVE DETECTION SYSTEM

A P P E N D I X   B

CERTIFICATE OF MAILING BY "EXPRESS MAIL"

Express Mail Mailing Label No. B03803631W

Date of Deposit 1-10-90

I hereby certify that this paper or fee is being deposited with the United States Postal Service "Express Mail Post Office to Addressee" Service under 37 CFR 1.10 on the date indicated above and is addressed to the Hon. Commissioner of Patents and Trademarks, Washington, D.C. 20231

Bryant R. Gold
(Typed or printed name of person mailing)

(Signature of person mailing)

TABLE OF CONTENTS 1.0 EXECUTIVE SUMMARY ............................................. 1-1
   1.1 *Performance Summary* .................................... 1-1
   1.2 *Scope of Work* .......................................... 1-4

2.0 DESCRIPTION OF SYSTEM ......................................... 2-1
   2.1 *Modifications to Phase 1 Design* ........................ 2-1
      2.1.1 Mechanical ....................................... 2-1
      2.1.2 Electrical ....................................... 2-4

3.0 LABORATORY DEVELOPMENT ........................................ 3-1
   3.1 *Simulants Development* .................................. 3-1
      3.1.1 Introduction ..................................... 3-1
      3.1.2 Measurements of Simulants ........................ 3-4
      3.1.3 Results and Conclusions .......................... 3-8
      3.1.4 Additions to Compensate for Simulant Location
           Outside Versus Inside Suitcase .................. 3-13
   3.2 *SAIC Reference Bag Distribution* ....................... 3-15
   3.3 *Basics of Discriminant Analysis* ....................... 3-16
      3.3.1 Details of features .............................. 3-21
          3.3.1.1 Image reconstruction .................... 3-21
          3.3.1.2 Flux correction ......................... 3-24
      3.3.2 Details of the Decision Calibration Procedure ... 3-26
   3.4 *Flux Map and Image Reconstruction* ..................... 3-28
   3.5 *In-house Acceptance Test* .............................. 3-30

4.0 SFIA-TWA INSTALLATION AND TESTS ............................... 4-1
   4.1 *Installation* ........................................... 4-1
   4.2 *Observed Bag Distribution* .............................. 4-3
   4.3 *Background Correction Model Calibration* ................ 4-6
   4.4 *Operation at SFIA* ..................................... 4-16
   4.5 *Radiation Safety* ...................................... 4-21
      4.5.1 Area and Personnel Dosimetry .................... 4-21
      4.5.2 Activation Monitoring ........................... 4-23
      4.5.3 Baggage Gamma Spectra ........................... 4-24

TABLE OF CONTENTS (Continued)

- 6.4 Analysis Efforts and Results....................6-11
  - 6.4.1 New Group Classification..................6-11
  - 6.4.2 Development of New Features................6-14
    - 6.4.2.1 PSND Related Features.............6-15
    - 6.4.2.2 Normalized Nitrogen Counts........6-15
    - 6.4.2.3 Side Detector Correlation Features....6-15
    - 6.4.2.4 Clustering Features...............6-16
    - 6.4.2.5 Other Features...................6-17
    - 6.4.2.6 Effect of New Features............6-18
  - 6.4.3 Improvement in Imaging....................6-18
    - 6.4.3.1 Optimizing the Smoothing Coefficients....6-18
    - 6.4.3.2 A New Flux Function...............6-19
  - 6.4.4 Domestic Vs. International Calibrations....6-19
  - 6.4.5 Effect of Changing Prior Probability in Discriminant Model....6-20
- 6.5 Lab Installation After Refurbishment..............6-21

7.0 SFIA-PAN AM....................................7-1

- 7.1 Installation...................................7-1
- 7.2 Observed Bag Distribution......................7-1
- 7.3 Background Correction Calibration..............7-11
- 7.4 Difficulties Encountered During Tests..........7-15
- 7.5 Decision Analysis..............................7-19

8.0 POST-TEST ANALYSIS EFFORT......................8-1

- 8.1 "Best Algorithm" Applied to All Data............8-1
- 8.2 Best Possible Performance of the System.........8-2
- 8.3 Possibilities of Reduced Number of Detectors or Reductions in Detector Array....8-5
- 8.4 Post Analysis on SCM Model......................8-7
- 8.5 Cf EDS Operational Experience..................8-21
  - 8.5.1 NaI Detector Performance.................8-23
  - 8.5.2 Detector Resolution......................8-23
  - 8.5.3 Detector Voltage.........................8-24 iv point in that plot is gotten by calculating the value of the two different features from the data set acquired for that bag. Note that the points for suitcases with explosives clump apart from suitcases alone. The discriminant function is a linear combination of the features which best separates the two groups of points. Points from the "with explosive" clump which fall on the right side of the line represent missed detections; similarly, points from the suitcase only group, which fall on the left side of the line are false alarms. The perpendicular distance between any point and the line, U12, represents a "sureness" for the decision. A threshold on this figure would appear as just a vertical or horizontal line; note that the ability to angle the line improves performance. Obviously, by drawing parallel lines to the discriminant, the number of false alarms and missed detections can be changed; this is the origin of the PD/PFA tradeoff curve, such as is shown in Figure 3.6. In practice, this analysis is generalized to several dimensions, and the separating surface becomes a hyperplane. Also, separate discriminant analyses are done for the sheet and bulk explosives separately, as different features must be used to detect these very different configurations of explosive. A brief mathematical description of the technique is given in Appendix B.

3.3.1 Details of features

A sample bag dataset is shown in Appendix A. As explained in that appendix, this is the basic data acquired by the system for each suitcase measured. It is a record of the net nitrogen gammas and neutron counts over the time of measurement of the suitcase, and also contains the peripheral data such as dimensions, destination, and weight of the bag. From this basic data, the features are computed. Most of the features are straightforward--such as the total nitrogen counts for the bag--but a few require more detailed explanation.

3.3.1.1 Image reconstruction

The most complicated features to compute are based on reconstruction of the nitrogen image. This image is a three-dimensional representation of the density of nitrogen in the cavity. The technique used to create the image

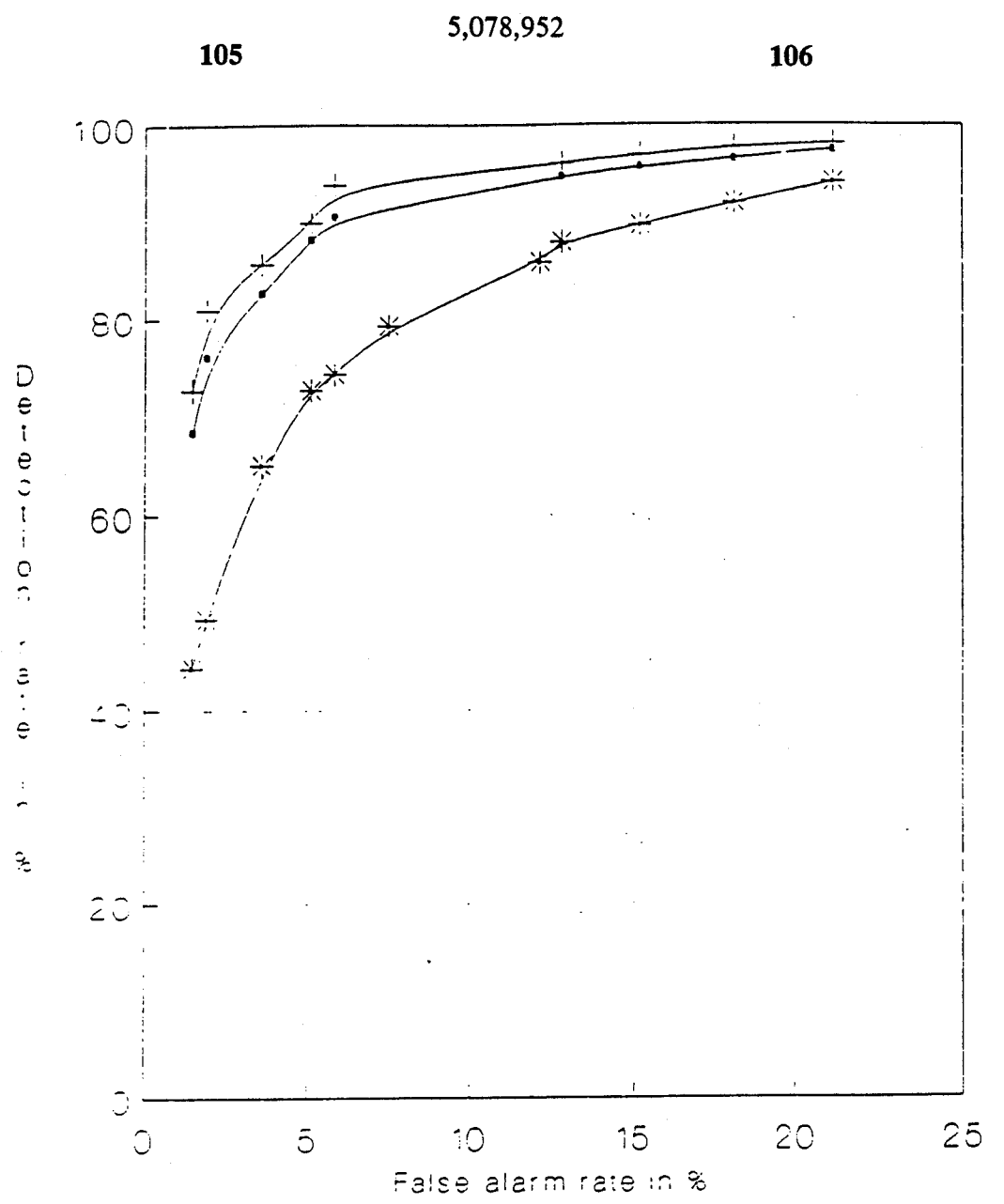
Figure 3.6 PD-PFA Trade Off
CFINT from the acquired data is the Algebraic Reconstruction Technique (ART) with regularization. The signal from the suitcase can be represented by a vector, S, which has the observed count rate observed in each detector at each time as its rows. If there were N detectors and T times of observation, then the first N rows of S are the counts in the detectors for the first time period, the next N are for the second time period, and so on up to the N * T row. Similarly, there is a vector p of nitrogen densities in the cavity. The cavity is divided up into a number of volume elements (voxels) each roughly the size of the detectors, a cube 4 inches on each side. The nitrogen content of each voxel describes the distribution of nitrogen densities to the degree of precision possible with the relatively large detectors used in the system. The voxels are simply numbered from front to back and left to right and put in the vector p. The signal and nitrogen density are related by a transfer matrix W:

$$S = W p \qquad (1)$$

The elements of W can be calculated by the use of the simulation code used in Phase I, or they can be measured by experiments with small amounts of nitrogen in nearly empty containers. In practice, estimation of the forward response matrix was done by use of the simulation code. The image reconstruction process was tested on experiments with "point" sources of nitrogen.

The objective in on-line operation is to calculate the value of the vector p from the measurement of S. Since there are more measurements (rows in S) than there are values to be determined (rows in p), the Algebraic Reconstruction Technique gives the usual least-squares solution:

$$\hat{p} = (W^T W)^{-1} W^T S \qquad (2)$$

Unfortunately, because of the noise present in the system and the high degree of correlation between the elements of W, the $W^T W$ matrix is ill-conditioned, and its inverse will have both large and small elements in it. In the reconstructed image, this will appear as artifacts and large variations in apparent nitrogen content. To reduce these effects and 3-23 increase the stability of the result, a smoothness constraint is added. This technique is known as regularization.[4] In this case, the smoothness constraint added is one that "penalizes" large first derivatives of the nitrogen density, i.e., it tries for a zero first derivative over the entire image. This has the effect of making the data smooth (if the constraint is forced to be followed, the image must be uniform) except where the data forces it to have a bulge of nitrogen. If K is the matrix operator for the first derivative of the p vector, then equation (2) becomes (by the application of the usual Lagrangian constraints):

$$\hat{p} = [(W^T W + g K^T K)^{-1} W^T] S \qquad (3)$$

In equation (3), g is the "smoothing coefficient;" the larger it is, the smoother the resulting estimate of p will be. This parameter requires adjustment to produce a good reconstructed image.

All of the terms in the square bracket in equation (3) are known from the construction of the system; thus, they can be computed in advance of on-line operation and stored as a single matrix. During the on-line computation of features, it is only necessary to do the single matrix multiplication, not the transposes and inversions. This is a substantial number of computations (the matrix in square brackets, the inverse transfer matrix, is 140 by 270 in this application), but feasible in the time available. This reconstruction produces a three dimensional image, where the number in each voxel is linearly related to the amount of nitrogen present in that voxel.

3.3.1.2 Flux correction

The next most complicated set of features are based on the correction to the gamma ray response due to changes in the neutron flux. In the Californium-based system, the source of neutrons is an isotope which decays with a fixed and known rate, and is thus quite easy to correct for (if the

---

[4] See, for example, S. Twomey, *Introduction to the mathematics of inversion in remote sensing and indirect measurements*, Elsevier Scientific Publishing Co., 1977

Note the peculiar result that the open C-ring 1 and 2 performance is only 0.8 (one half) percent worse on bulk false alarm rate, but is 0.3 (one half) percent better on sheet false alarm rate than the system with all 60 detectors (parenthetical values are after adjusting PDs to match via the above tradeoffs). The trend towards worse performance is much clearer with the drop to 15 detectors, where the bulk PFA is 3% worse and the sheet PFA is 2.5% worse. Figure 8.1 shows the performance of the bulk calibration, after all false alarm rates are adjusted to 3.7%, which shows the general effect from each step change in the system configuration. As mentioned, more work is required to obtain definitive results.

8.4 Post Analysis on SCM Model

More extensive analysis was done on the background model to see if the model could be simplified and to determine the possible counting rate dependency of the model. To study these topics, a complete background data base acquired during the SFIA-TWA through SFIA International tests was retrieved and merged to form one complete background data set. In an effort to simplify the SCM process, a search for the best overall model was done. Based on $R^2$ and Root Mean Square Error (RMSE) criteria, four two variable models were identified as best. They were two models each consisting of CC*C8 and H*C8 terms. Figure 8.2 shows the RMSE comparison of the four best overall models for the selected detectors. Detectors were chosen to best represent all positions and counting rates. For the cases with source on the bottom, represented by detectors D31 through D54, one model (CC*C8 + HY) out-performed the others. However, this model was eliminated since there was large errors in estimating intercept (the constant term). The two models including H*C8 term were very similar since CC and CL regions are right next to one another and are highly correlated. Thus, the square of CC term is almost equivalent to the product term of CC and CL. This reduced the number of models down to two, one each containing CC*C8 and H*C8. The selection of the two models is not surprising since these were also the best models when each section of the data base belonging to different airport testing was treated separately. The best model would be CC*C8 + HY*CC, based on the better fit for the high counting rate transmission detectors.

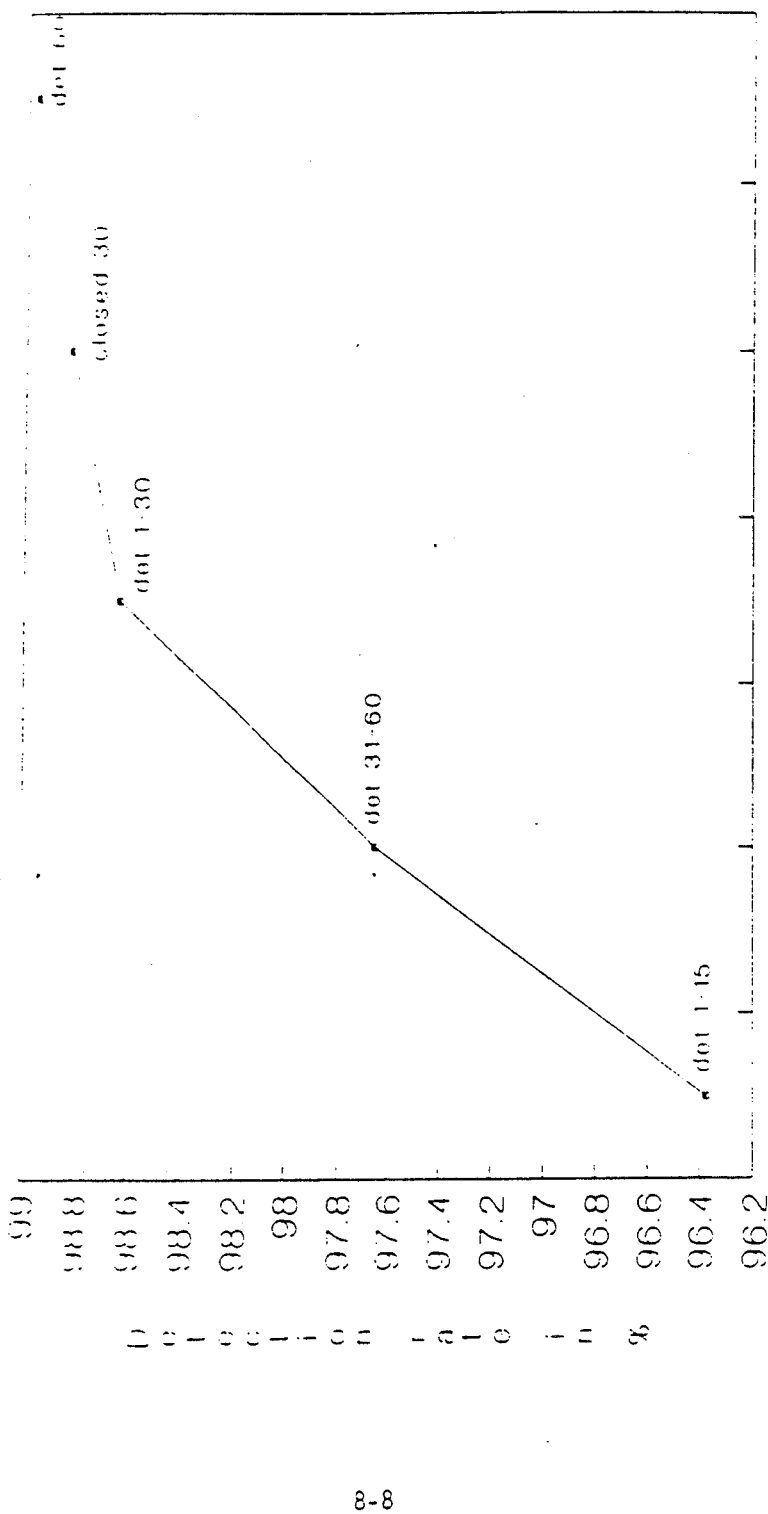
Figure 8.1 PD - Detector Trade Off
Cflax - Calibration Bulk

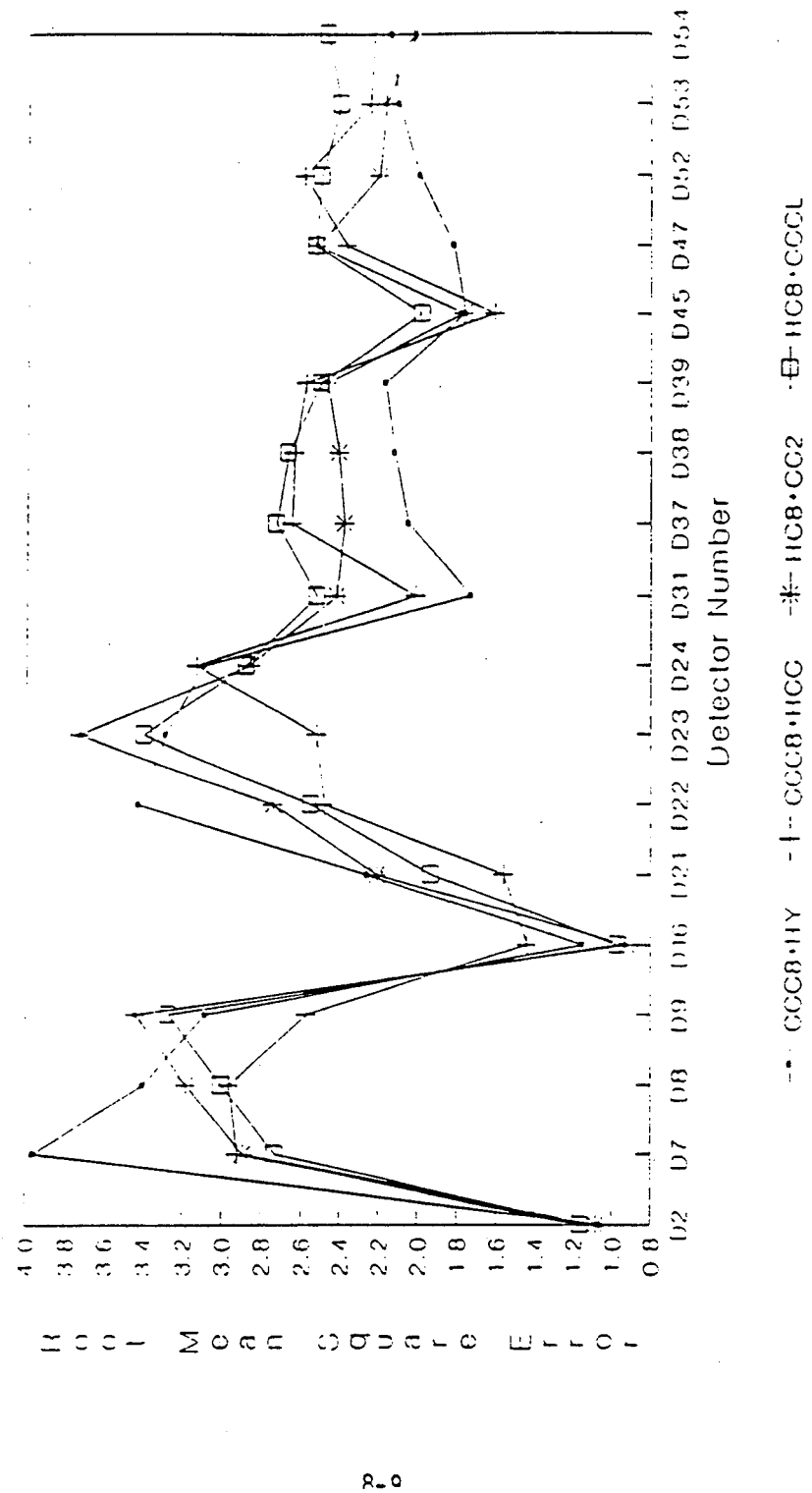
Figure 8.2 RMSE Comparison
(Among 4 Best Models)

To make certain that the data base did not include any outliers or some type of systematic errors hindering the model performance, residuals were plotted for various observations. No systematic trend was found, but the general trend was that the large residuals belonged to the cases with large amount of stainless steel and pvc. This was expected since these interference materials test the extreme limits of the model.

Mean empty cavity hydrogen and nitrogen counting rates were plotted for all detectors (see Figures 8.3 through 8.6). The mean empty cavity counting rates were derived from averaging numerous empty cavity runs. Four sets of data are plotted on each graph, each representing separate installations. The data set "LAB" represent the empty cavity runs taken after refurbishment while the system was installed in lab facility. The data sets "SFO2A" and "SFO2B" represent the runs taken at SFIA International with sources fully in and sources partially retracted respectively. Figures 8.3 and 8.5 are somewhat misleading since source decay correction had been calculated continuously since April 1987, meaning all region counting rate was multiplied by the source decay correction factor, which is defined as:

$$\text{Source decay factor} = e^{lt}$$

where $l = \ln 2 / T_{1/2}$ ($T_{1/2}$ is the half life of Cf source) and $t$ is the elapsed time. In Figures 8.4 and 8.6 the recorded counting rates were divided by the source decay factor to give the actual counting rates of the system. Empty cavity hydrogen yield is indicative of overall gamma counting rates or actual intensity of sources, assuming no other geometric changes are made; while empty cavity nitrogen yield is more indicative of the variation in pileup contribution as the overall counting rates are changed.

To determine whether the background models were counting rate dependent, an identical model was applied to each section of the background data base and the variations in coefficients and intercepts were studied. The particular model chosen for this purpose was the best one variable model, namely, the product of CC and C8 plus a constant or an intercept. The coefficient of 8-10

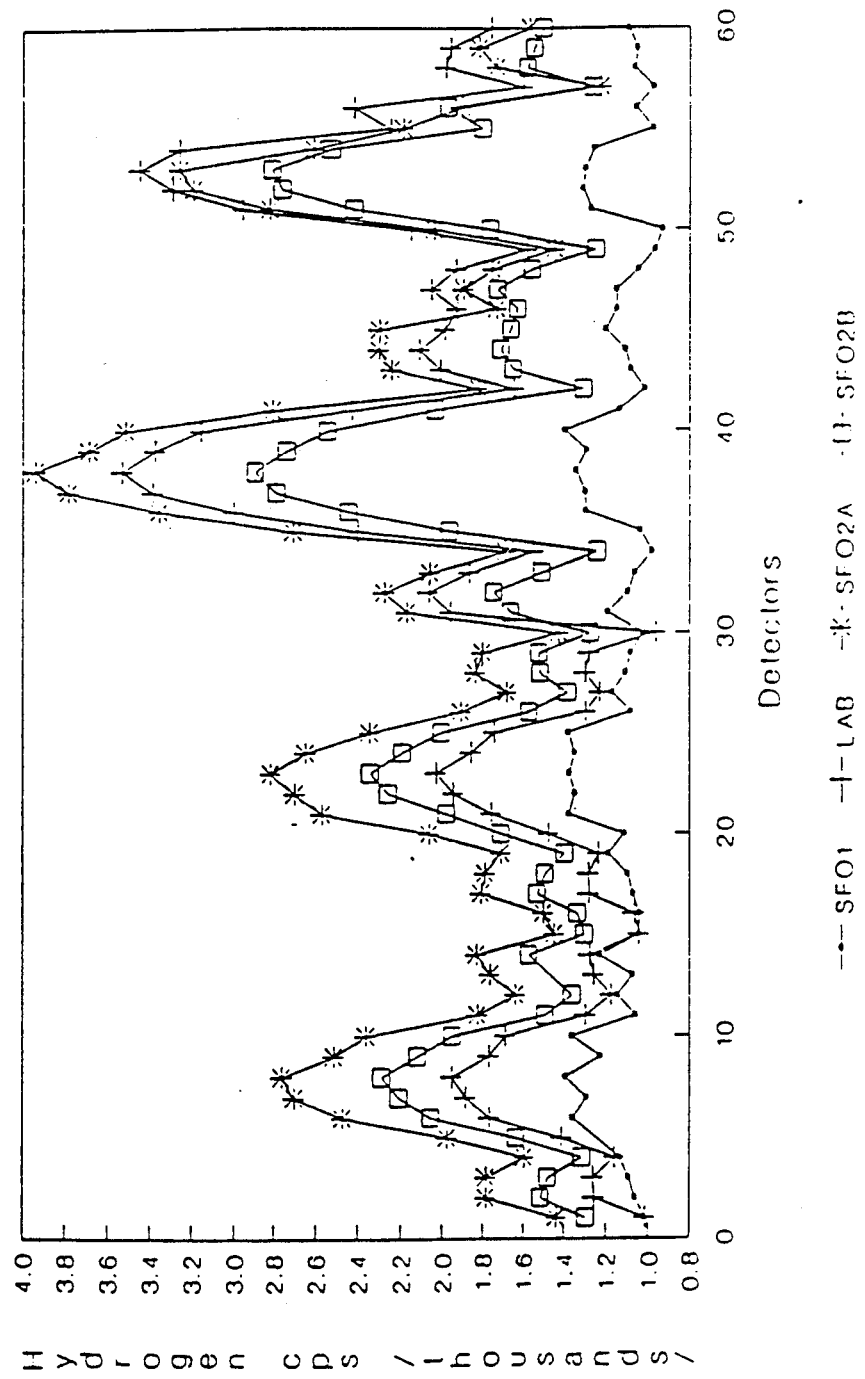
Figure 8.3 Mean Empty Cavity Counting Rates (Hydrogen Region)

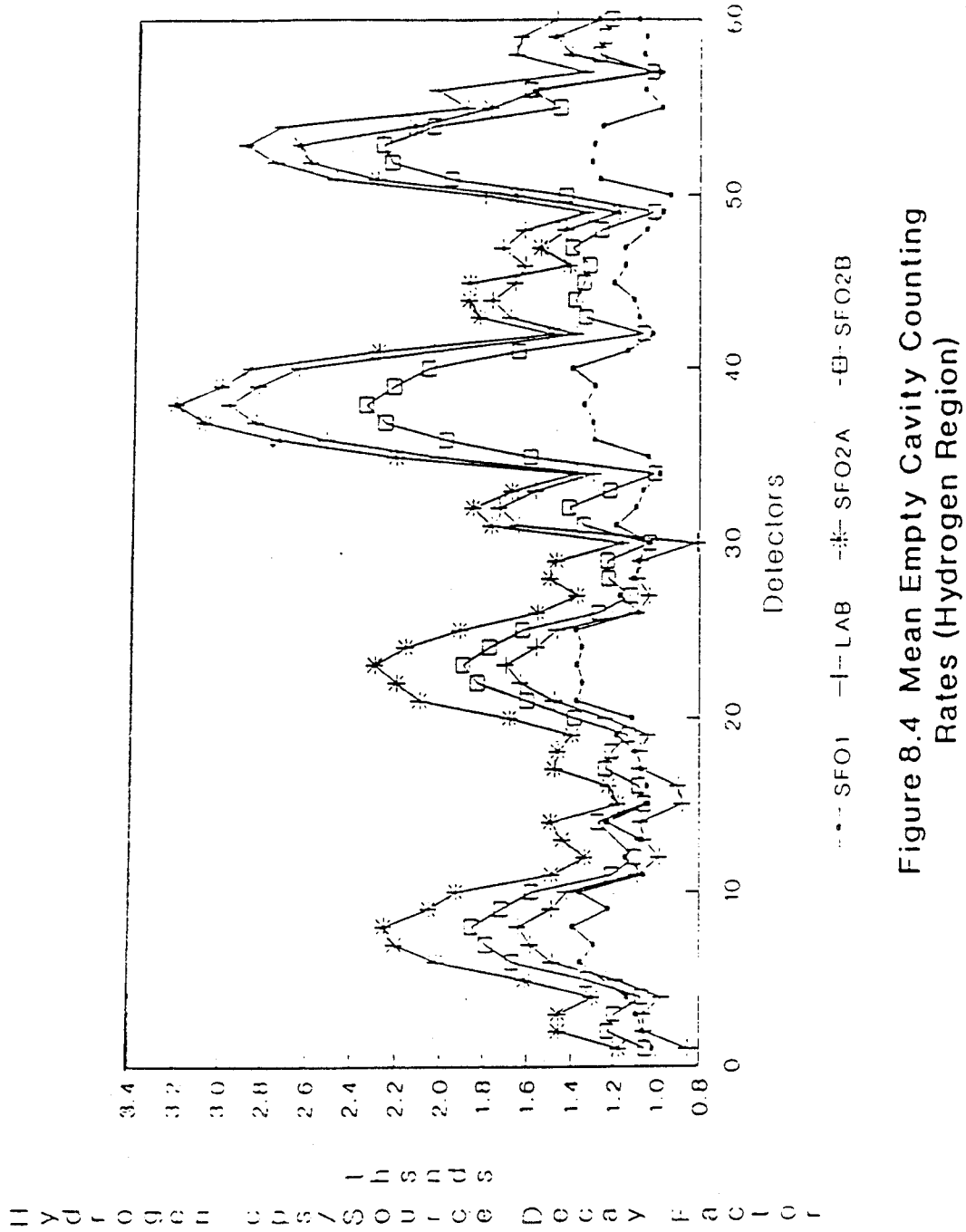
Figure 8.4 Mean Empty Cavity Counting Rates (Hydrogen Region)

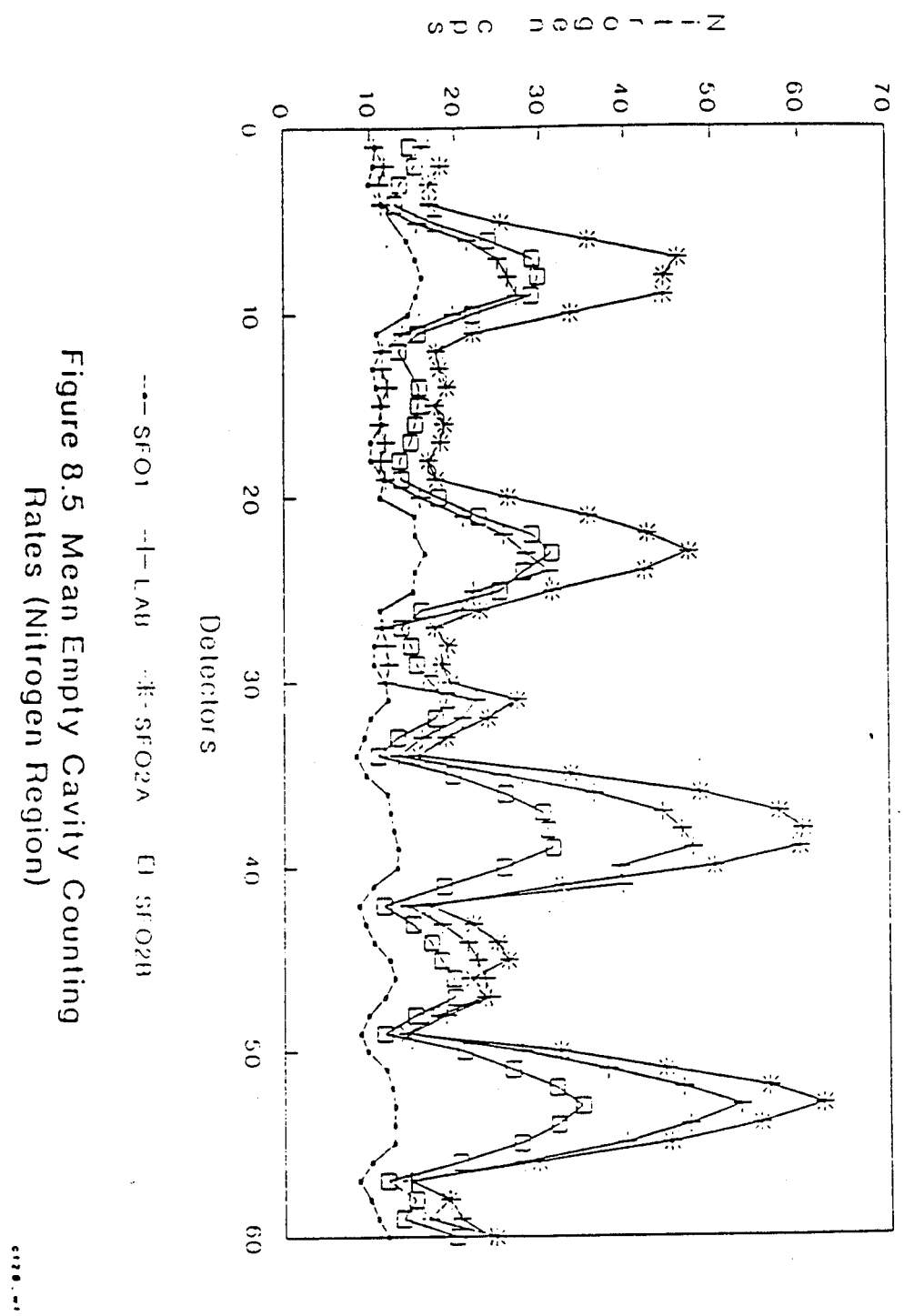
Figure 8.5 Mean Empty Cavity Counting Rates (Nitrogen Region)

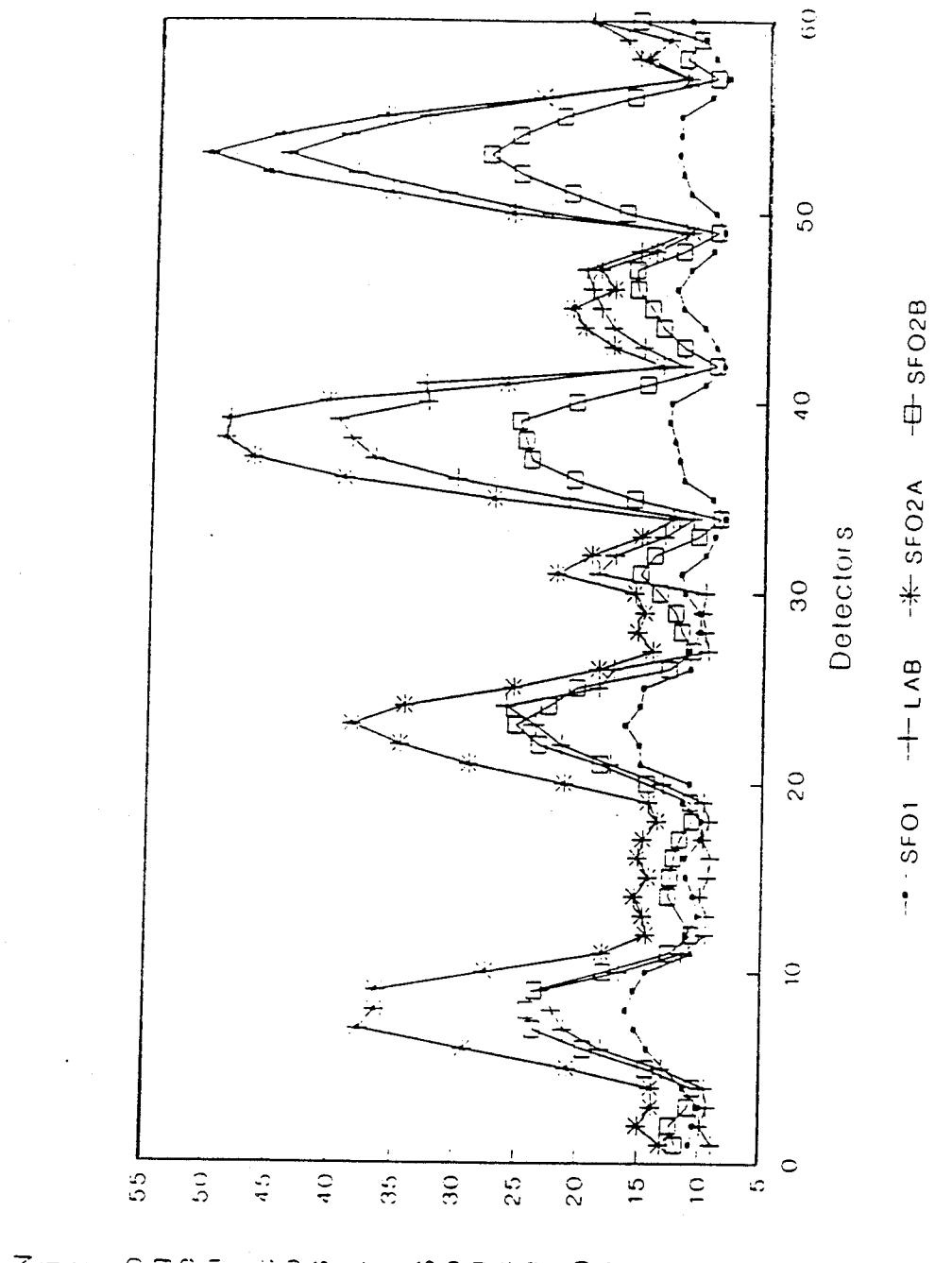
Figure 8.6 Mean Empty Cavity Counting Rates (Nitrogen Region)

the product term is plotted for all detectors in Figure 8.7. Except for SFIA-TWA the coefficients are all in the range from 0.00045 to 0.0005. This variation is very small, and since some of the variation could be explained by the uncertainty in estimating the coefficients, the magnitude of variation contributes to less than 0.9 cps in the nitrogen background counting rate. The similar behavior of the coefficients between different installations is more evident in Figure 8.8 which displays the coefficients normalized to the coefficients of SFIA-TWA. The irregular behavior of the SFIA-TWA coefficients can be explained by numerous changes made to the system since SFIA-TWA and during the refurbishment effort. For example, each ASP was fine tuned to optimize the pileup rejecter; a number of detectors were moved closer to the cavity by removing a portion of $B_4C$ in front of them, increasing their sensitivity, etc. Another exception to the consistent behavior of the coefficients is the unusually large coefficients of detector 47. A possible explanation for this is the misadjustment of the ASP. It is speculated that the pileup rejector of that particular ASP was not optimized, allowing more pileup events to pass through. This was supported by the higher background nitrogen counting rate for detector 47 than that for adjacent detectors. The discrepancy was more evident for the cases with interference materials.

Unlike the coefficients, the intercepts seems to behave proportionally with counting rates (see Figure 8.9). To verify the proportionality, the intercept values were plotted as a function of empty cavity hydrogen and nitrogen counting rates for selected detectors (see Figures 8.10 and 8.11). Detectors 3,8,33 and 38 were chosen to represent both source positions and different counting rates. It is seen from the figures that the relationship between the intercept and the hydrogen yield is linear. This linear relationship confirmed that the intercept is counting rate dependent. Consequently, there is a strong indication that the background model can be simplified by calibrating the intercept values by the change in counting rates if the terms in the model are unchanged. If this is possible, new background data measurements and model searches do not have to be repeated each time a change is made to the system. Based on the linear behavior of the intercept and the constant behavior of the coefficients, the simplified

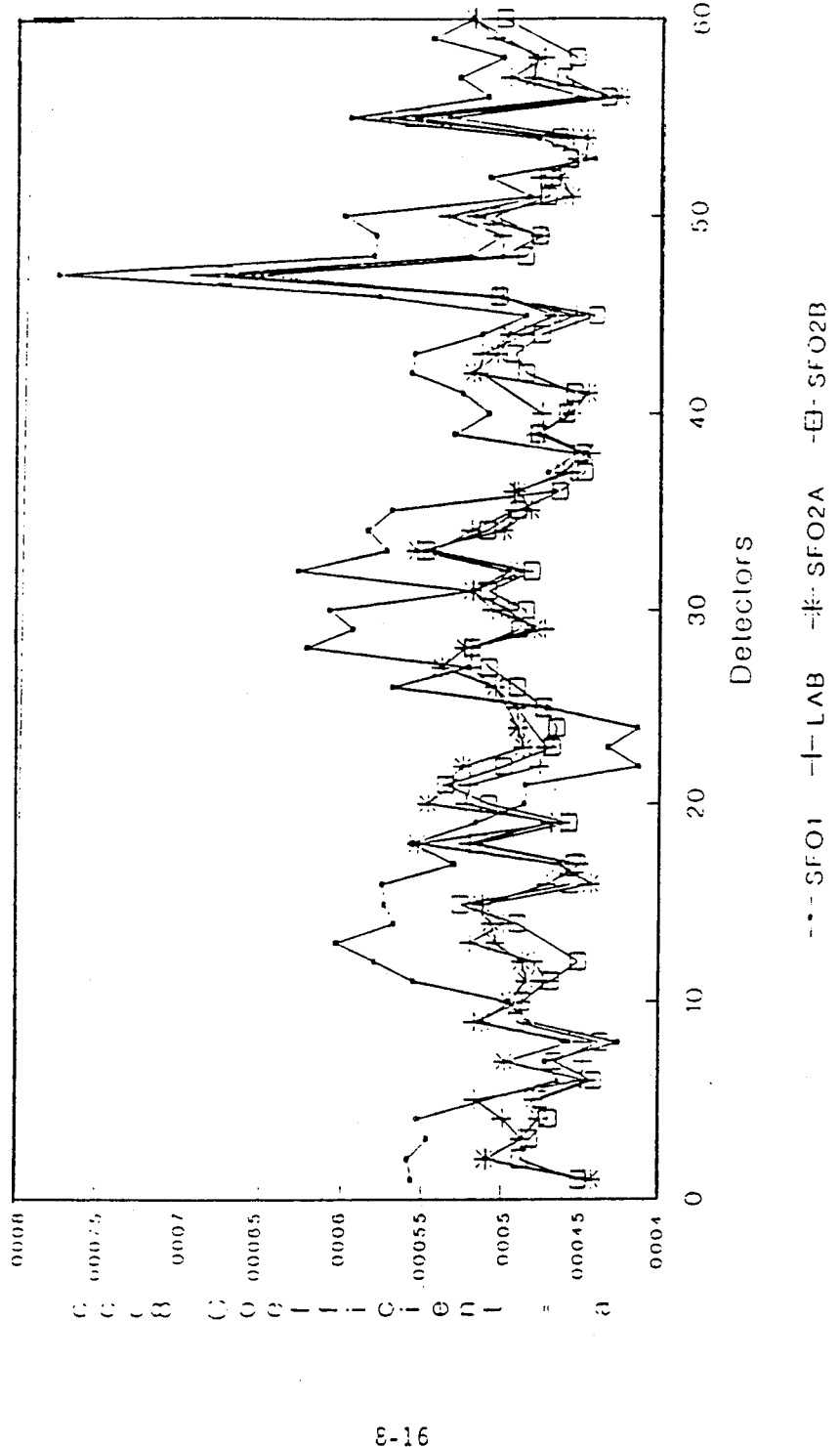
Figure 8.7 Comparison of SCM Coefficients (Model: NW=a·CC·C8+intercept)

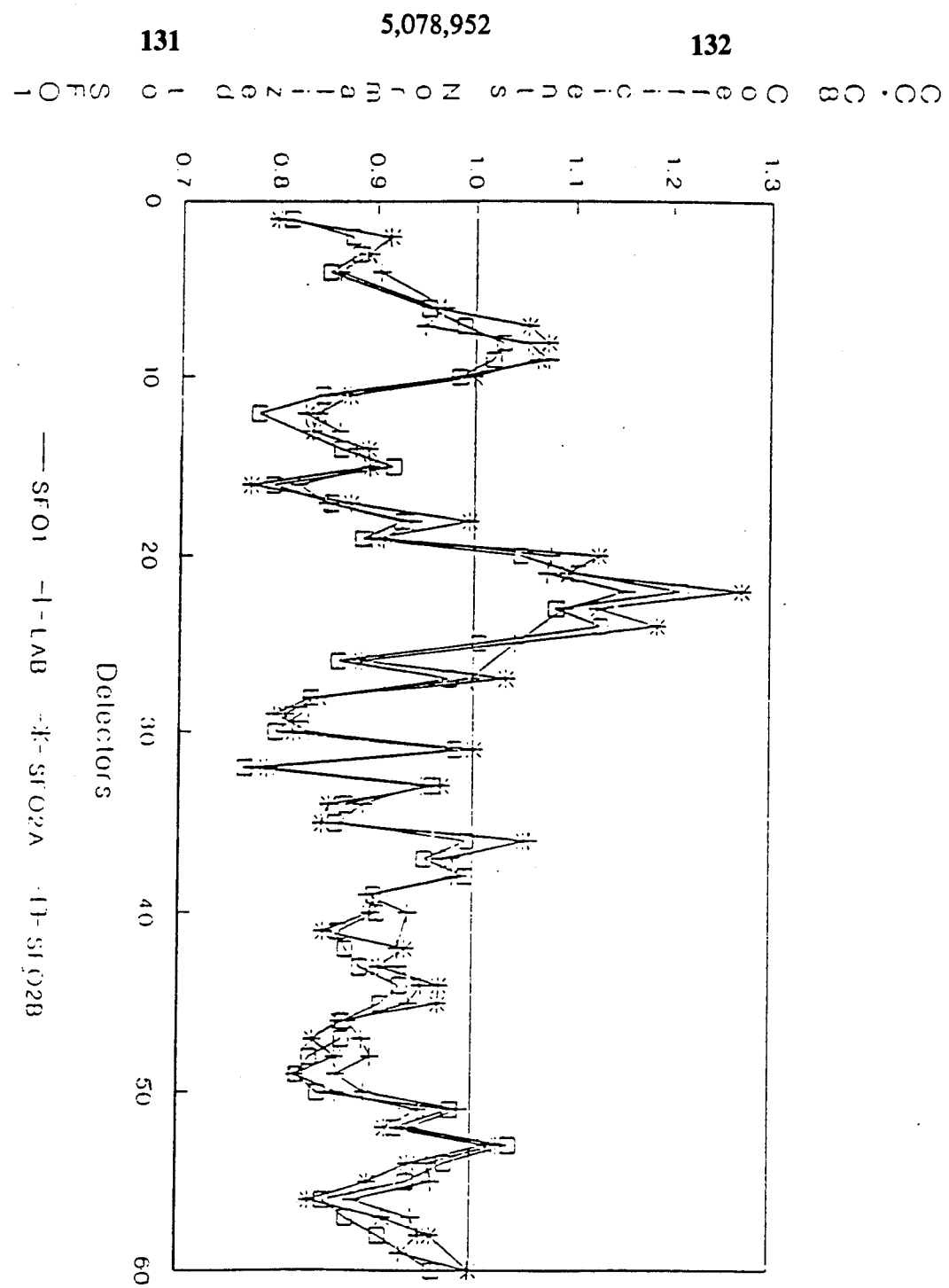
Figure 8.8 Comparison of SCM Coefficients (Model: NW=a·CC·C8·intercept)

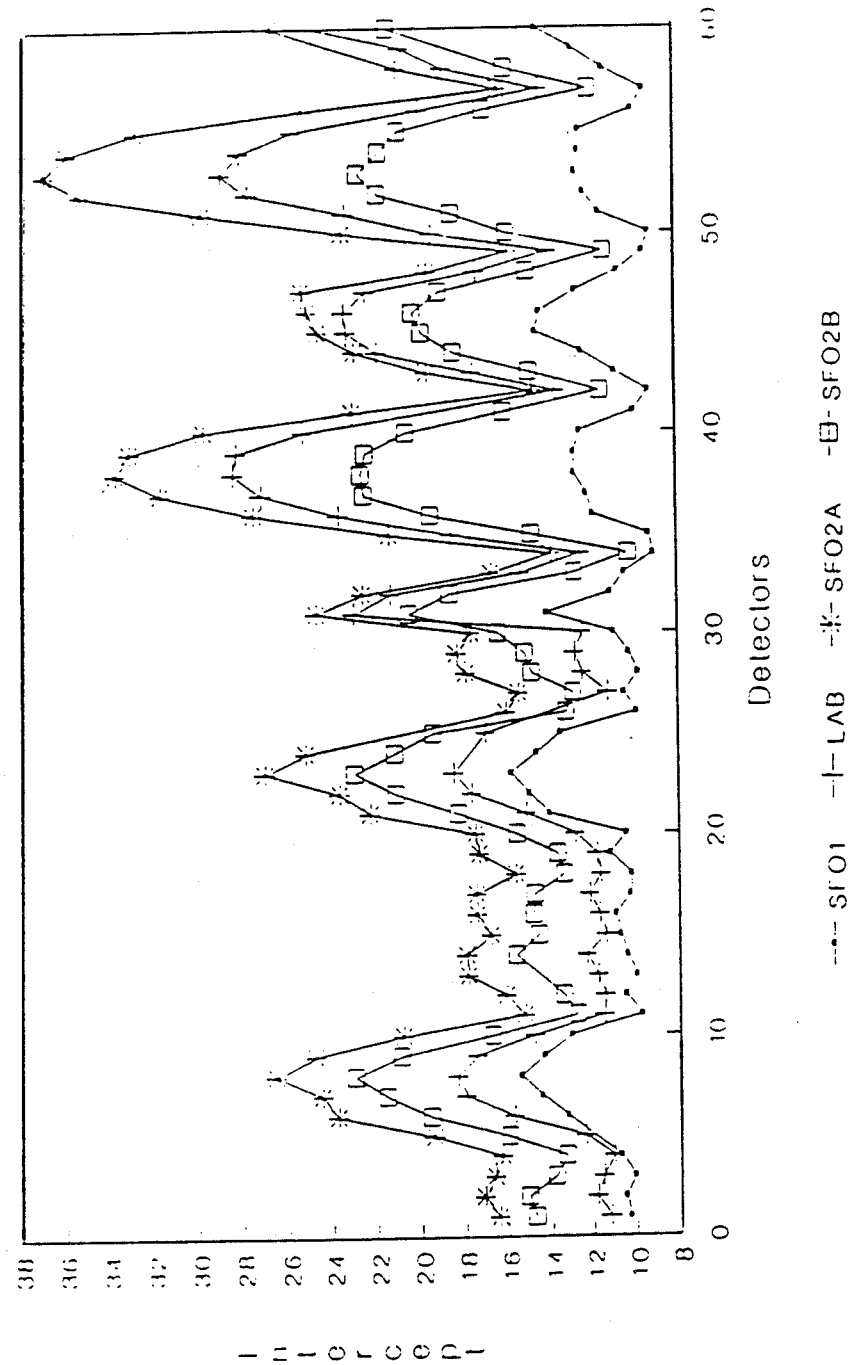
Figure 8.9 Comparison SCM Intercept Values (Model: NW=a·CC·C8+intercept)

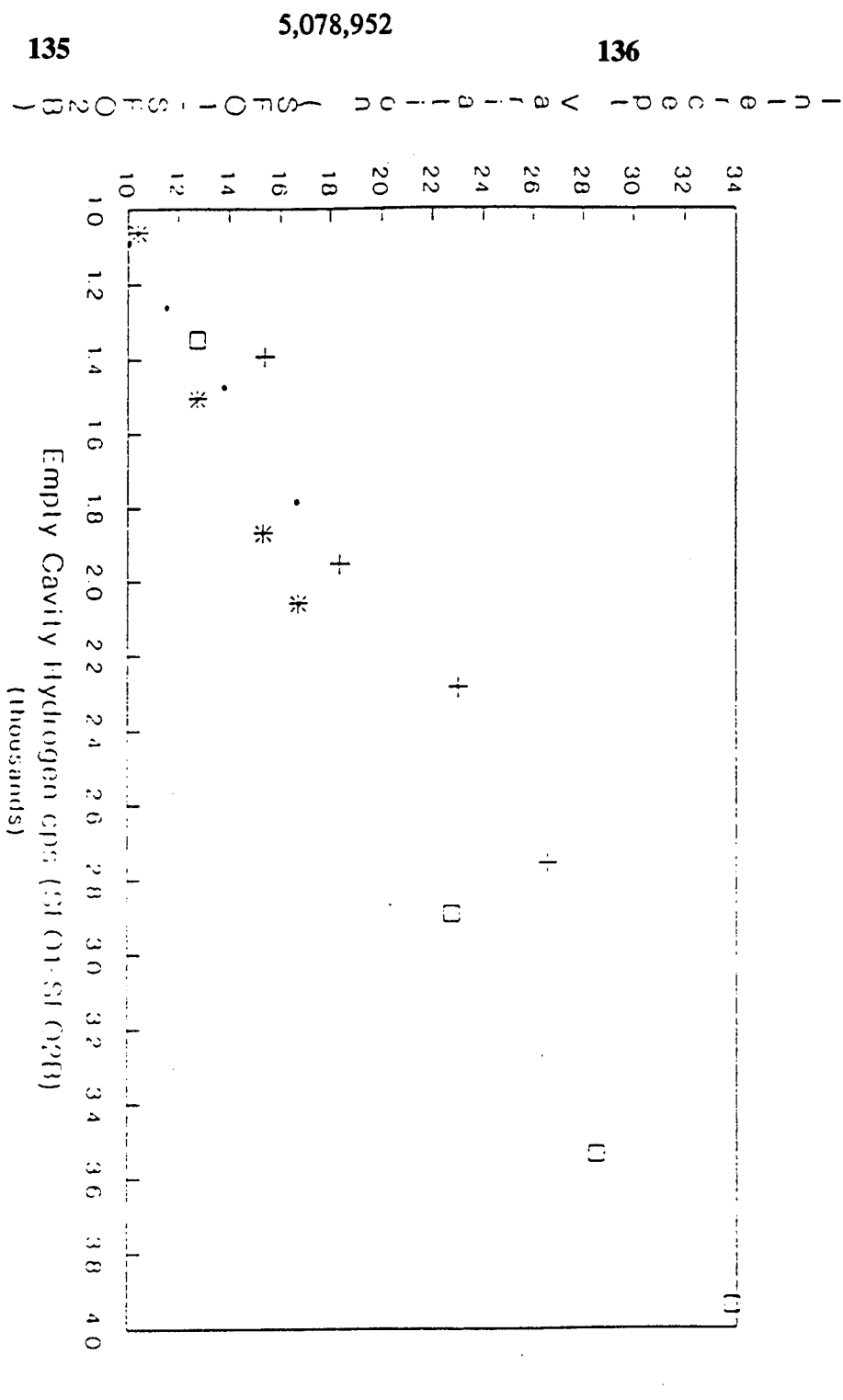
Figure 8.10 Counting Rate Dependency of Intercept (Model: NW=a·CC·C8+intercept)

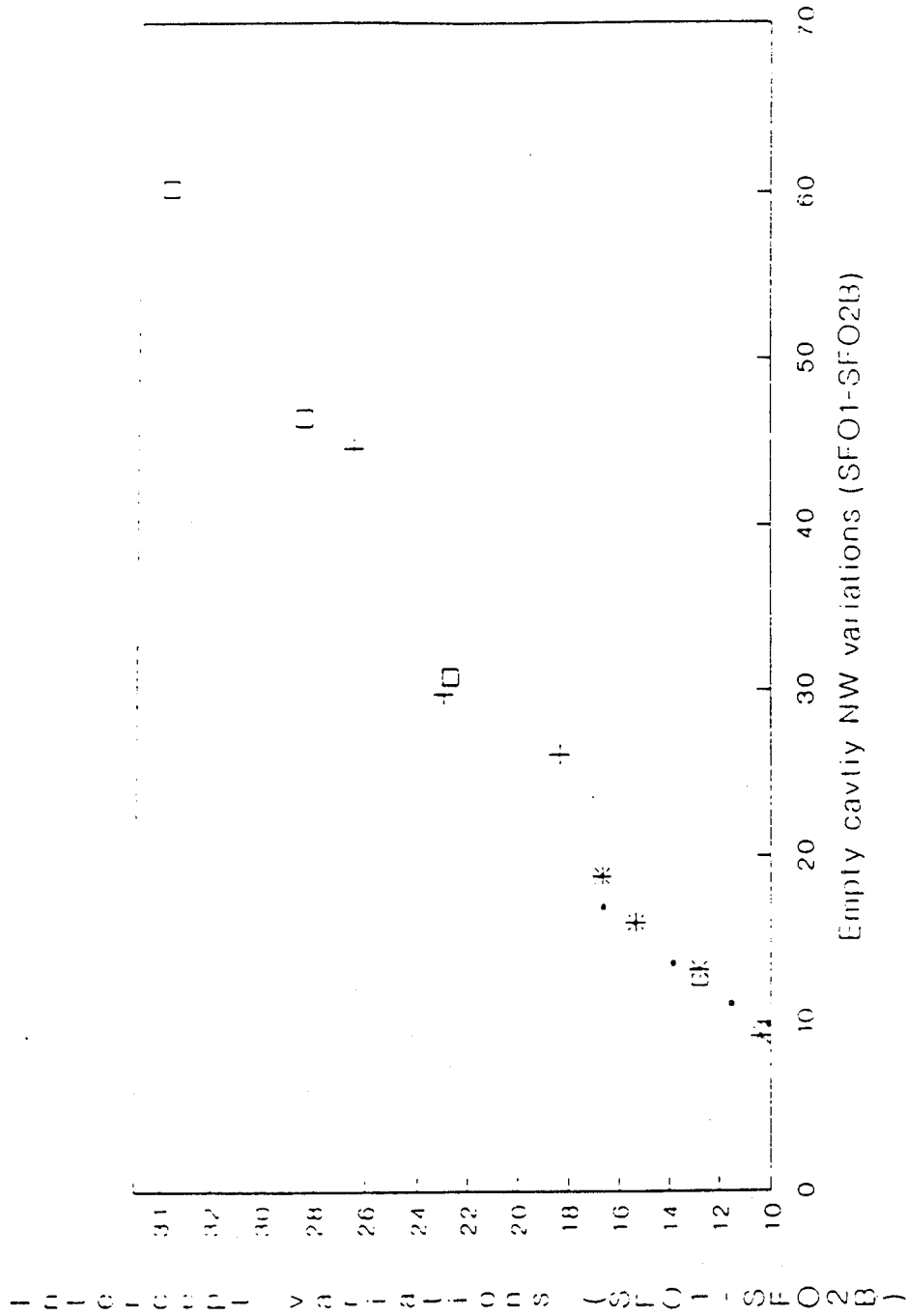
Figure 8.11 Nitrogen CR Dependency of Intercept (Model: NW=a•CC•C8+intercept)

model could be as follows: The intercept term estimates the changes in the cavity structure (i.e. the changes in source strength, the detector positions, etc.) while the model variables explain the background contributions from the various contents of suitcases. This technique worked very well for all suitcases scanned in tests. No false alarm or misdetection was attributed to a failure in the background subtraction.

8.5 Cf EDS Operational Experience

The daily test logs for the field tests were reviewed to estimate the system availability and identify the principal cause of downtime and operational difficulties.

In general the system availability was very high. Once the system was assembled and commissioned for each test site, availability was 90-95%. This was due to an average rate per testing day of 0.34 lost time problems, requiring about one to two hours each to restore normal operation. In addition, there were more numerous small problems not involving significant lost time but requiring a bag or two to be run through the system again at a loss of a few minutes per day.

System start-up procedures each day involved various checks but primarily involved detector stabilization checks and adjustments as needed to bring them within range of the automatic stabilization software. Generally a few, typically three, detectors failed to stabilize properly and were disabled by operator instruction to the computer. The computer was able to compensate for the absence of some detectors. Start-up including running several SAIC standard bags typically took 40 minutes unless unusual problems were encountered. Start-up time was not considered lost time for availability purposes. Following system start-up, various benchmark cases were run each day (the reference bags) to track system performance for later reanalysis. This typically required another 20 to 40 minutes per day and was also not considered lost time.

Gozani, et al
Docket 47475

MULTI-SENSOR EXPLOSIVE DETECTION SYSTEM

APPENDIX C

**CERTIFICATE OF MAILING
BY "EXPRESS MAIL"**

Express Mail Mailing Label No.
B03803631W

Date of Deposit 1-10-90

I hereby certify that this paper
or fee is being deposited with
the United States Postal Service
"Express Mail Post Office to
Addressee Service" under 37
CFR 1.10 on the date indicated
above and is addressed to the
Hon Commissioner of Patents and
Trademarks, Washington, D.C. 20231

Bryant R. Gold
(Typed or printed name of person mailing)

(Signature of person mailing)

5.0 LAX-UNITED TEST

Between the first airport test and the second, a number of small modifications were made to the system, primarily in software. These changes made it easier to produce more detailed information about the bag distribution (length, width, etc.). The improvements in the decision module were also incorporated. Difficulties which occurred during the operation of the system were noted so that permanent fixes could be developed. During this test, the difference in bag distribution between domestic and international luggage was developed.

5.1 LAX Installation

The second test installation for the Cf-based system was in the Los Angeles International Airport at the United Air Lines gate area 72A in the south end of their luggage make-up area.

The Cf system was located at ground level, but over a large basement baggage room that was no longer being used. The placement of the Cf system had to be such that it would have adequate structural support underneath and still have clearance overhead for forklift maneuverability. Figure 5.1 (SAIC drawing D-FAA-270) shows the plan view of the system installation that met these requirements. Also shown is the placement of the XENIS X-ray system and a 10' x 20' office trailer. Electrical power and phone lines were installed to complete the installation and make ready for the luggage testing.

After testing, the Cf system was removed and returned to the laboratory; however, the office trailer was left intact to be used for testing of the D,D-based EDS scheduled to be installed a short time later.

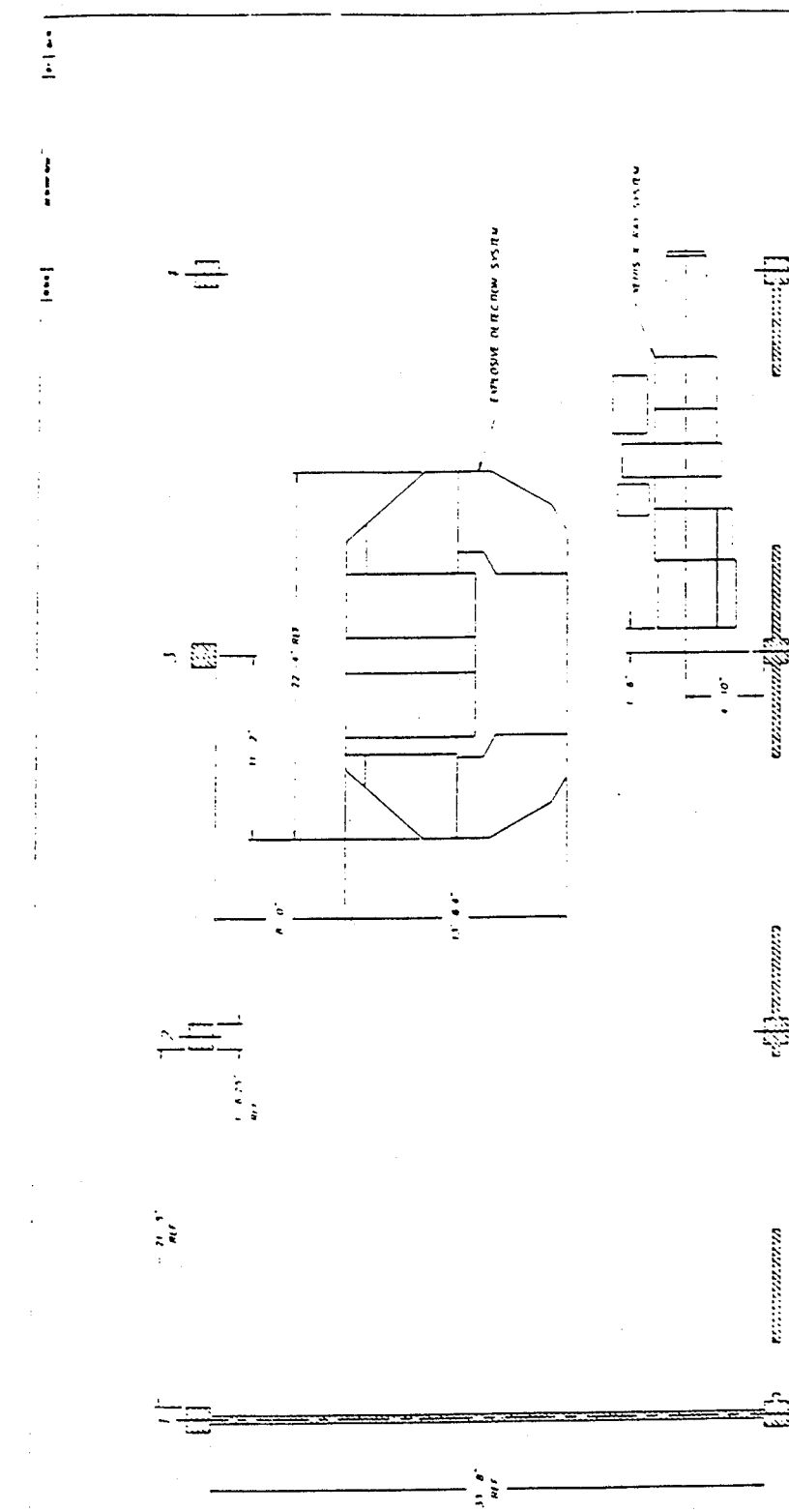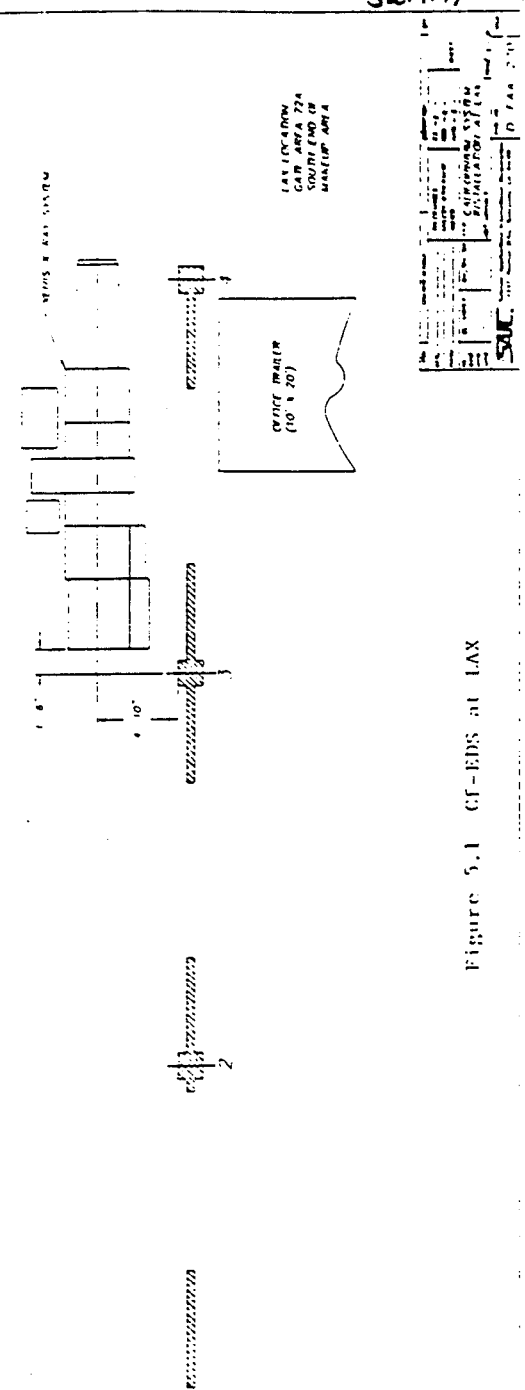
Figure 5.1 CT-EDS at LAX

5.2 Observed Bag Distribution

5.2.1 Statistics of Clean Bags

From August 14 to September 4, approximately 4000 clean bags were run through the system, out of which about 20% were international bags. Tables 5.1 to 5.4 show the weight, length, volume, and grams of nitrogen distribution of these bags.

From the tables, about 90% of the bags fall into a 10 to 50 pound range with 20 to 30 pounds being the mean weight range. Similarly, about 90% of the bags fall within the length range of 15 to 30 inches, with a mean range of 20 to 25 inches. Unlike weight and length, volume distribution is more spread out over large volume ranges. The mean volume range of the distribution is between 4000 to 5000 cubic inches. The grams of nitrogen distribution of LAX clean bags is a little bit easier than the SFIA TWA distribution. Here, almost 61 percent of the bags have less than 300 grams of nitrogen, as opposed to 53% in SFIA TWA. About 35% of the bags contain a 1 to 2 bomb equivalence, and less than 5 percent of the bags contain more than a 2 bomb equivalence.

TABLE 5.1

LAX WEIGHT DISTRIBUTION
14 AUGUST TO 4 SEPTEMBER

| RANGES (LB) | # OF BAGS | PERCENT |
| --- | --- | --- |
| < 10 | 141 | 3.35 |
| 10-20 | 1093 | 25.96 |
| 20-30 | 1311 | 31.13 |
| 30-40 | 974 | 23.13 |
| 40-50 | 456 | 10.82 |
| 50-60 | 162 | 3.85 |
| 60-70 | 50 | 1.19 |
| > 70 | 24 | .57 |
| Total | 4211 | |

TABLE 5.2

LAX LENGTH DISTRIBUTION
14 AUGUST TO 4 SEPTEMBER

| RANGES (IN) | # OF BAGS | PERCENT |
|---|---|---|
| > 5 | 1 | 0.02 |
| 5-10 | 6 | 0.14 |
| 10-15 | 68 | 1.61 |
| 15-20 | 913 | 21.68 |
| 20-25 | 1363 | 32.37 |
| 25-30 | 1498 | 35.57 |
| 30-35 | 334 | 7.93 |
| 35-40 | 24 | 0.57 |
| > 40 | 4 | 0.09 |
| Total | 4211 | |

TABLE 5.3

LAX VOLUME DISTRIBUTION
14 AUGUST TO 4 SEPTEMBER

| RANGES (CU IN) | # OF BAGS | PERCENT |
|---|---|---|
| > 1000 | 15 | 0.36 |
| 1-2000 | 251 | 5.96 |
| 2-3000 | 691 | 16.41 |
| 3-4000 | 735 | 17.45 |
| 4-5000 | 878 | 20.85 |
| 5-6000 | 772 | 18.33 |
| 6-7000 | 524 | 12.44 |
| 7-9000 | 310 | 7.36 |
| 9-11000 | 28 | 0.66 |
| >11000 | 7 | 0.17 |
| Total | 4211 | |

TABLE 5.4

LAX GRAMS OF NITROGEN DISTRIBUTION
14 AUGUST TO 4 SEPTEMBER

| RANGES (GRAMS) | # OF BAGS | PERCENT |
|---|---|---|
| > 300 | 2568 | 60.99 |
| 3-500 | 1117 | 26.53 |
| 5-700 | 361 | 8.58 |
| 7-900 | 102 | 2.42 |
| 9-1100 | 43 | 1.03 |
| > 1100 | 19 | 0.45 |
| Total | 4211 | |

5.2.2  Frequency Block Charts

Frequency block charts are used to represent the overall distributions of bags in any two parameters. In particular, when developing a group classification scheme for the decision algorithm, frequency block charts with nitrogen and volume information can be used to separate high nitrogen density bags from the low ones.

Figures 5.2, 5.3, and 5.4 show the volume versus grams of nitrogen distribution for no simulant, bulk, and sheet simulant cases, respectively. From these figures, the following observations can be made:

i) Most of the non-simulant cases contain less than 300 grams of nitrogen, while almost all of the simulant cases contain more than 300 grams of nitrogen. Thus, 300 grams of nitrogen can be used as a threshold to alarm a bag as an explosive in the data analysis module.

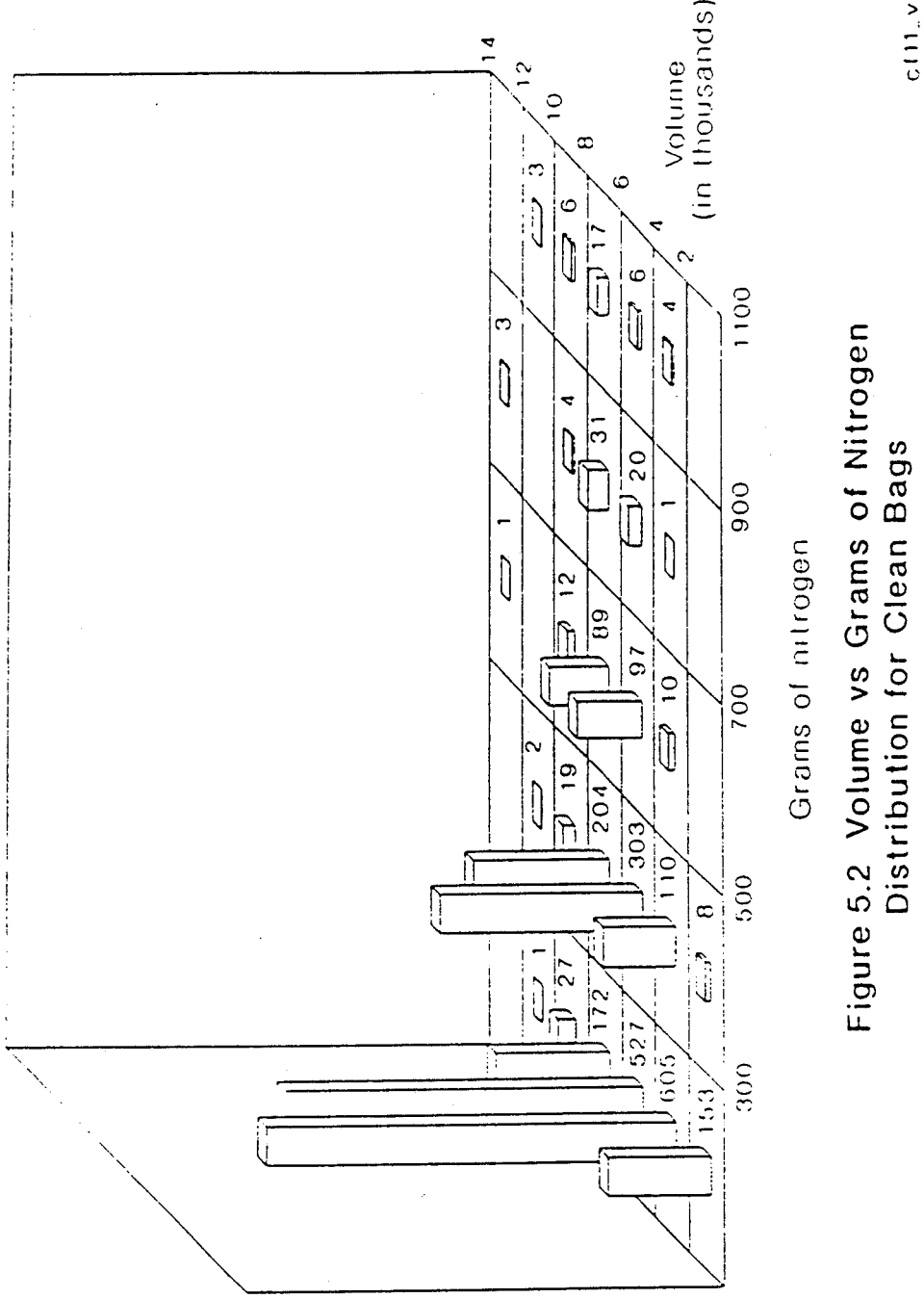
Figure 5.2 Volume vs Grams of Nitrogen Distribution for Clean Bags

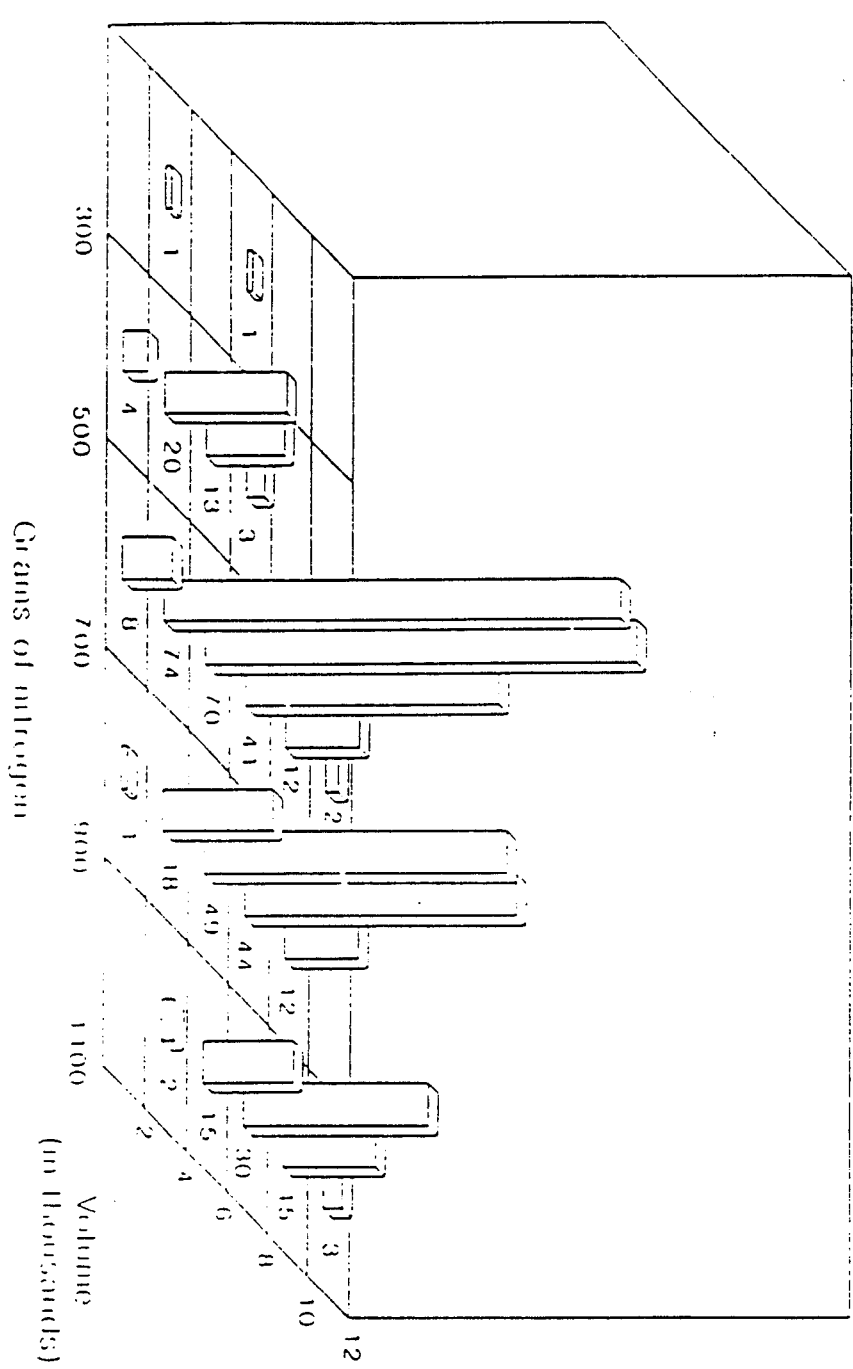
Figure 5.3 Volume vs. Grams of Nitrogen Distribution for Bulk Cases

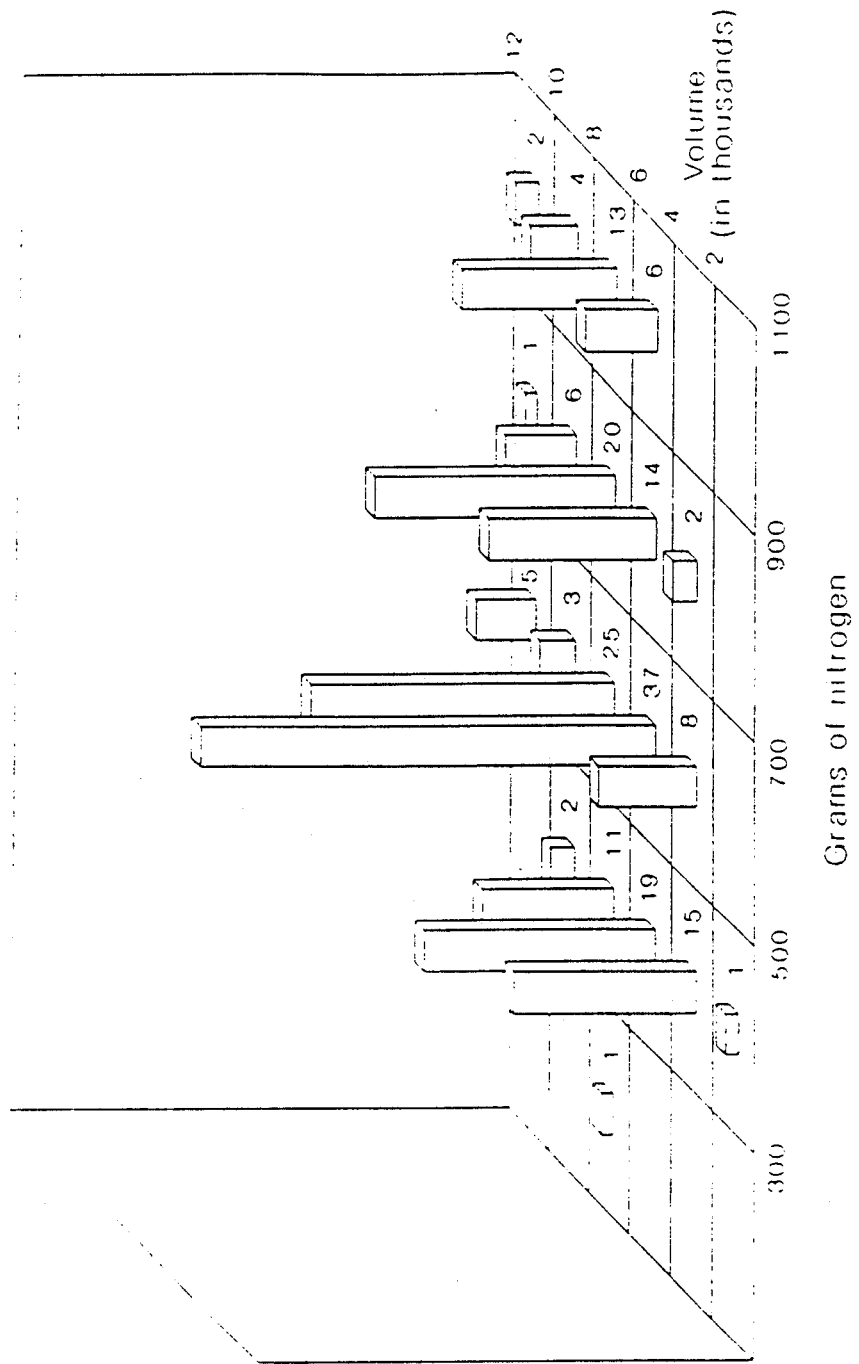
Figure 5.4 Volume vs. Grams of Nitrogen Distribution for Sheet Explosives ii) Most of the overlapped cases between non-simulant and simulant occurred in the 300 to 700 grams of nitrogen range. Consequently, more groups should be classified in these ranges because it is more difficult to differentiate between simulant and non-simulant cases in this region. See Section 5.5 for more details on group classification.

Figures 5.5, 5.6, and 5.7 show the flux versus normalized nitrogen distribution for non-simulant, bulk, and sheet simulant cases, respectively. From these figures, and by comparing with the volume versus grams of nitrogen distributions, the following observations can be made:

i) Most of the non-simulant cases have normalized nitrogen less than 200, while only one simulant case has a normalized nitrogen less than 200.

ii) As with the volume versus grams of nitrogen, most of the non-simulant cases lie at the bottom right-hand side, while the majority of the simulant cases lie at the top left-hand side.

iii) Compared to the volume versus grams of nitrogen distribution, the distribution for the normalized nitrogen and the flux seems to have less deviation of data points. That's because normalized nitrogen and flux are more reliable parameters than grams of nitrogen and volume.

5.2.3 Distribution of Simulant Classes

During the period from August 17 to September 4, 1987, a total of 6392 passenger bags passed through the system, out of which 4296 cases were clean, 1480 cases were bulk, and 616 cases were sheet explosives. Table 5.5 shows the distribution of simulant classes during that period.

5-9

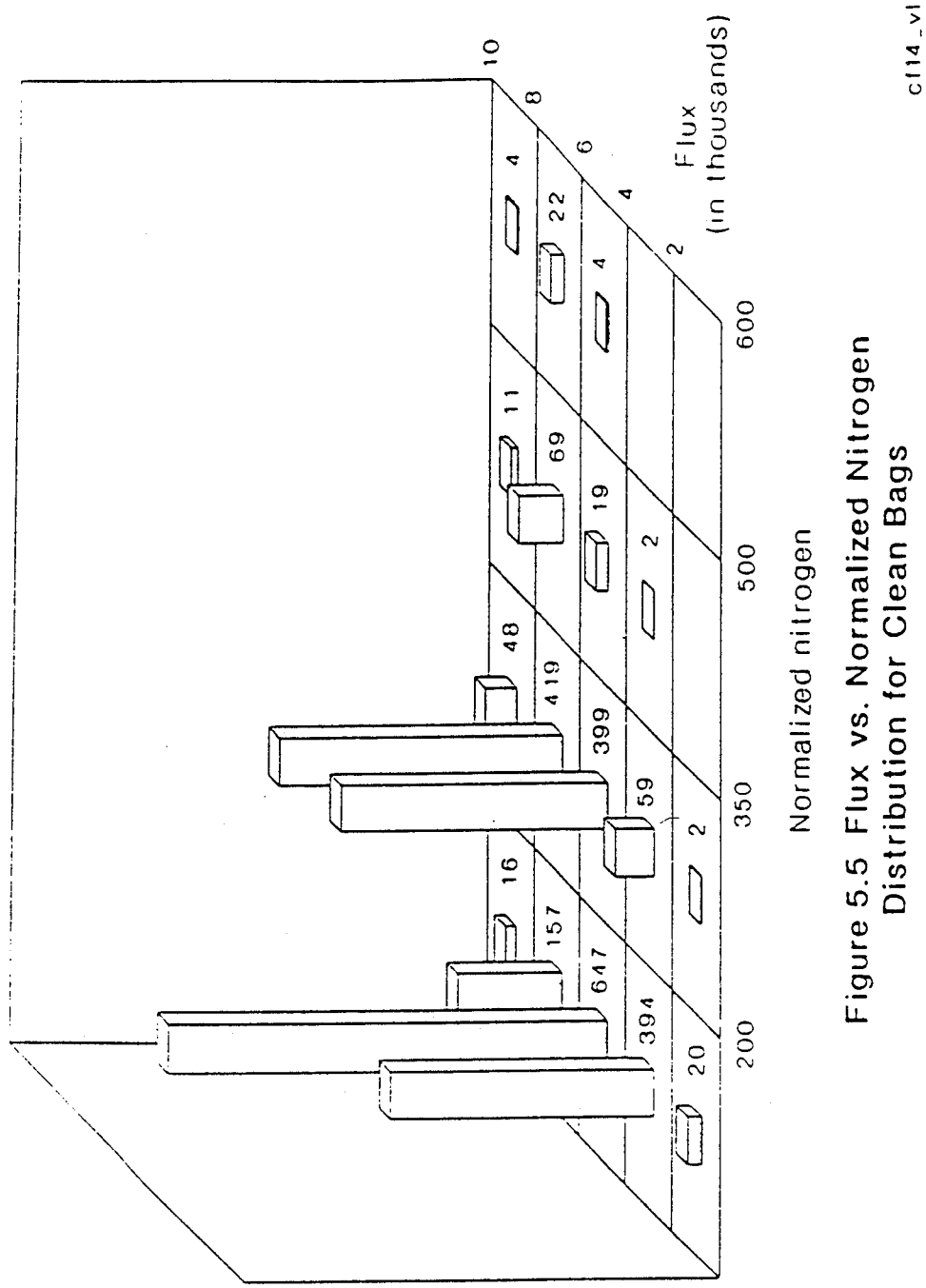
Figure 5.5 Flux vs. Normalized Nitrogen Distribution for Clean Bags

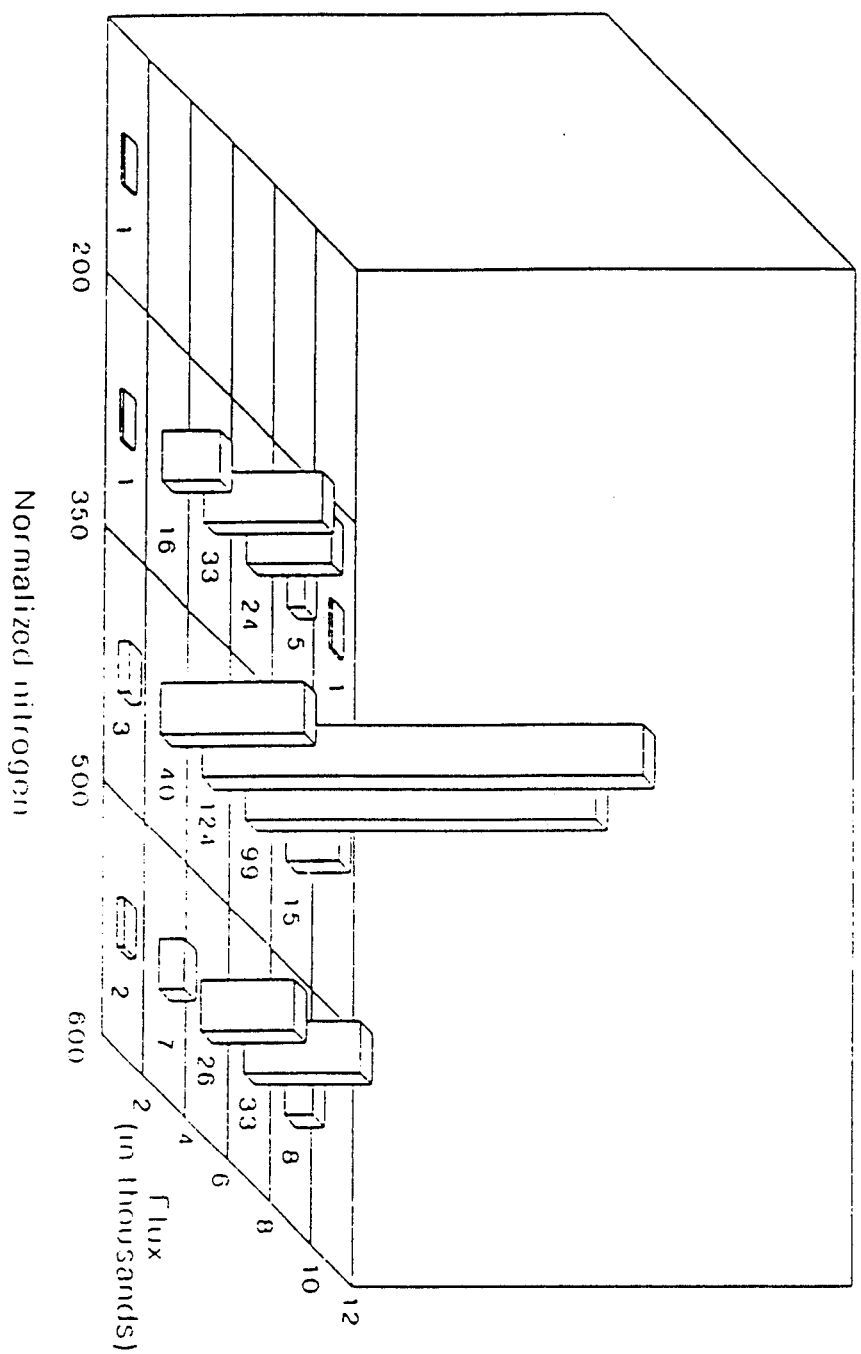
Figure 5.6 Flux vs. Normalized Nitrogen Distribution for Bulk Cases

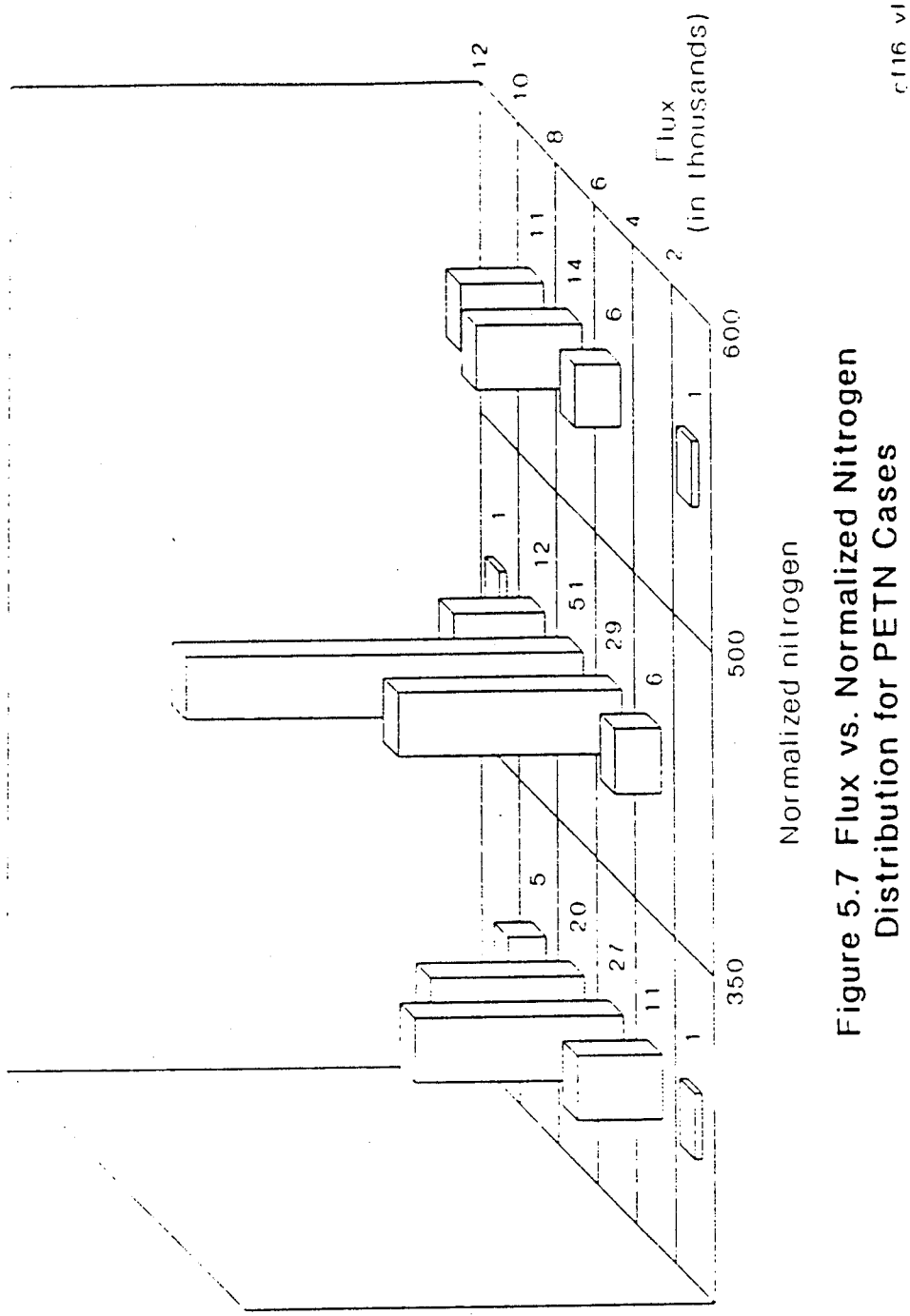
Figure 5.7 Flux vs. Normalized Nitrogen Distribution for PETN Cases

Table 5.5

Distribution of Simulant Classes (8/17 - 9/4)

| CLASS | SIMULANT TYPE | # OF CASES | % OF TOTAL |
|-------|---------------|------------|------------|
| 2 | Domestic | 3269 | 51.1 |
| 3 | C4 | 386 | 6.0 |
| 4 | Water Gel | 725 | 11.3 |
| 5 | International | 799 | 12.5 |
| 6 | PETN Sheet | 616 | 9.6 |
| 7 | Dynamite | 369 | 5.8 |
| 8 | Military | 34 | .5 |
| 9 | Reruns | 194 | 3.0 |
|   |   | 6392 |   |

5.2.4   Distribution of Groups

Group classification, which is explained in more detail in Section 5.5, is a very important part of decision algorithm because it separates high density bags from low density bags. A frequency distribution of groups can show the relative number of bags between no-simulant, bulk, and sheet explosives. Table 5.6 shows the group distribution of LAX data for the last week of testing. From the table, one can see that group 1 contains most of the non-simulant cases. In groups 2 to 5, most of the cases are still non-simulant, while in groups 6 to 10 most of the cases have simulants.

TABLE 5.6

LAX GROUP DISTRIBUTION FOR DISCRIMINANT ANALYSIS

| GROUP | NO SIM | BULK | SHEET | % NO SIM | % BULK | % SHEET |
|---|---|---|---|---|---|---|
| 1 | 1467 | 0 | 0 | 42.83 | 0.00 | 0.00 |
| 2 | 40 | 60 | 26 | 1.17 | 1.75 | 0.76 |
| 3 | 241 | 58 | 51 | 7.04 | 1.69 | 1.49 |
| 4 | 184 | 16 | 27 | 5.37 | 0.47 | 0.79 |
| 5 | 270 | 13 | 18 | 7.88 | 0.38 | 0.53 |
| 6 | 37 | 188 | 48 | 1.08 | 5.49 | 1.40 |
| 7 | 60 | 94 | 66 | 1.75 | 2.74 | 1.93 |
| 8 | 25 | 52 | 13 | 0.73 | 1.52 | 0.38 |
| 9 | 39 | 133 | 37 | 1.14 | 3.88 | 1.08 |
| 10 | 38 | 105 | 19 | 1.11 | 3.07 | 0.55 |

5.3 Background Correction Model

No new SCM model was needed for this installation, as the model described in Section 4.3 was sufficient (no major changes were made to the system hardware between these two tests). A few detectors were replaced for reasons ranging from poor resolution to unstable gain. After replacement, a series of measurements were made with empty cavity and suitcases. The counting rates of all regions were compared to the same cases acquired during the SFIA-TWA installation. The counting rates agreed within 2% for most cases. Hence, no effort was made to revise the background model that was present in Section 4.3 above.

5.4 EDS Problem Highlights

5.4.1 Introduction

The Cf and D,D field operators kept a daily log of the problems encountered in the field. The two systems were tested at San Francisco (SFIA) and Los Angeles (LAX) International Airports, with each test running typically over a three month period. As the Cf and D,D are similarly designed, most problems that occurred were not unique to either system, with the exception of the neutron generator (discussed in the Final Report for the DD project). Therefore the problem highlights for each system are combined in the discussion below.

5.4.2 Biases and Specifications

The daily logs for both systems were more specific for operating procedure and hardware problems, and less specific for software problems. The software problems were fixed immediately when found, and were thus non-chronic. Although international, domestic, and cargo tests were not combined for data analysis, in the problem highlights no specific distinction was made. Bag jams and light beam problems caused the highest loss of running time. Bag jams were divided into two types: software (from the light beam) or hardware related. A hardware jam occurred when either a strap or tag caught between the conveyor and the transition plate and the bag became physically jammed in the cavity, or when a bag became stuck diagonally in the cavity. A software jam occurred when a tag or strap passed in front of the light beam before or after the bag, causing a multiple triggering of the light beam. When this occurred, the software thought there were two bags in the system, so when only one bag exited the system, the software assumed the other "bag" was still in the cavity. The software interpreted this condition as a jam.

Another common problem was VAX crashes. A VAX crash resulted in a complete system shutdown. The average shutdown time was about seventy minutes, which included time spent restabilizing the detectors. In the SFIA test, two out of three VAX crashes were a result of faulty serial line controllers. A VAX crash sometimes followed an MCA lock-up message and jammed light screen, due to CAMAC error. This type of crash is suspected to be caused by an AC-power fault.

There were problems with MCA lock-ups, which caused the computer-generated stabilization cycle (STAB) to fail in its search for peaks. The problems were at times cleared by cycling the ADC right hand switch, or the bin, off and on.

Detector malfunctions also occurred. Three of the 60 detectors were disabled during the test period. During system teardown, the detector failures were traced to cabling difficulties.

Some other frequent problems (often manifested as Repeats) were due to nitrogen counts out of bounds, STAB interference, and timing errors. The timing errors often occurred on the second bag after a reset. STAB interference was caused by the system software erasing the MCAs while a data acquisition for a bag was happening.

Occasionally the XENIS system drained power to the rest of the system. This drain primarily affected the CAMAC interface, which was the interface for the light beams and other peripheral units. This was traced to the XENIS compressor, which would sometimes trip the main circuit breaker when it was turned on. Other power fluctuations were suspected, but did not occur during those times that the AC powerline monitor was operating.

Belt misalignment was much less of a problem during LAX than it was during the SFIA-TWA test, with only one serious misalignment occurring.

5.5 CF-LAX Decision Algorithm

The CF-LAX decision algorithm was developed using a 3-way discriminant analysis and a group structure based on grams of nitrogen and volume.

5.5.1 Performance Summary

The overall on-line performance using the CF-LAX decision algorithm is shown below:

Table 5.7

Performance Summary (8/17 to 9/4/87)

|  | % | # of bags |
|---|---|---|
| PFA (Domestic Only) | − 4.98% | 3269 |
| PFA (International Only) | − 6.75% | 799 |
| PFA (Military Bags) | − 36.36% | 33 |
| PFA (TOTAL) | − 5.58% | 4068 |
| PFA (RECYCLE) | − 56.71% | 194 |
| PD (BULK) | − 95.55% | 1480 |
| PD (PETN) | − 78.41% | 616 |
| PD (TOTAL) | − 91.82% | 2096 |

Here, the "PFA (RECYCLE)" rate is the percentage of false alarms which alarm again when run through the system a second time.

5.5.2 Domestic Versus International/Military Bags

Overall, false alarm rates for international and military bags were higher than for domestic bags. This is because international/military and domestic bags are packed differently. Most of the international bags that false-alarmed contained leather, wool, silk clothing, mutiple shoes, or food material such as cheese, meat, and canned food. Similarly, most of the military bags that false-alarmed contained wool uniforms and heavy leather boots. These materials contain a considerable amount of nitrogen. Table 5.8 shows the nitrogen distribution of domestic and international bags. Figure 5.8 also shows the graph of the distribution, comparing domestic to international luggage.

The table and graph show that international bags appear more frequently in the higher nitrogen ranges than the domestic bags. Consequently, it is more difficult to differentiate between simulants and the suitcases. Unfortunately, due to the small number of cases, the same detailed comparison cannot be made for the military bags.

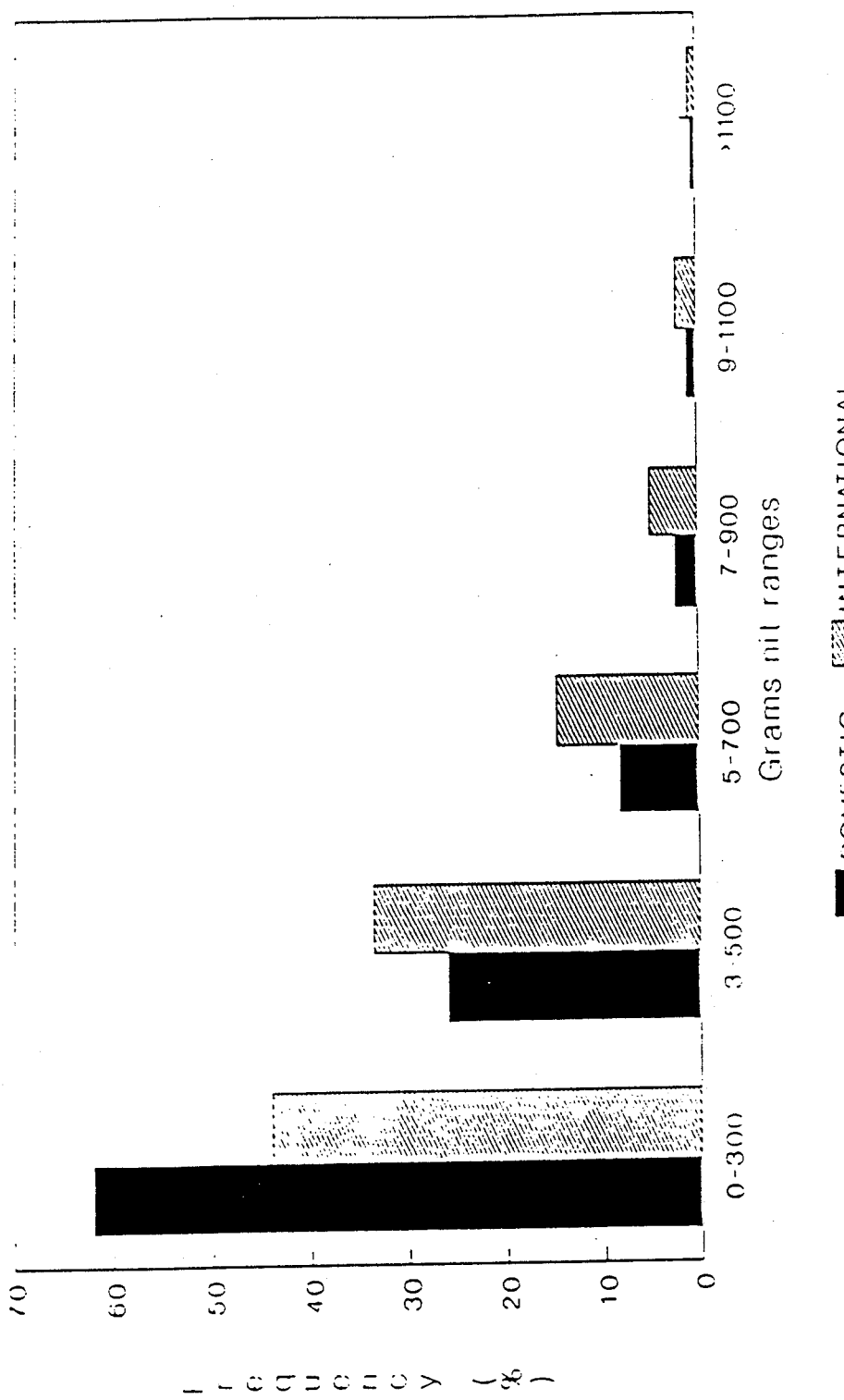
Figure 5.8 Domestic Vs. International Nitrogen Distribution

Table 5.8

Nitrogen Distribution of Domestic and International Bags

| NITROGEN RANGE (GRAMS) | DOMESTIC (%) | INTERNATIONAL (%) |
|---|---|---|
| 0 - 300 | 62.04 | 44.06 |
| 3 - 500 | 26.09 | 33.57 |
| 5 - 700 | 8.20 | 14.69 |
| 7 - 900 | 2.27 | 4.90 |
| 9 -1100 | 0.96 | 2.10 |
| > 1100 | 0.44 | 0.70 |

5.5.3 Recycled Bags

Only 110 cases out of 194 (54.74%) recycled cases realarmed at LAX. It appears that half of the recycled bags are borderline cases and a small change in measurement could effect the decision. A study of 63 cases of the recycled bags were done by comparing the features of a false alarm bag with its corresponding rerun features. Approximately 44% of the cases rerun had a change in group. 27% of the group change was due to a significant change in volume, 54% due to a change in grams of nitrogen, and the remaining 16% had no significant change in volume or grams of nitrogen. From these figures, it appears that the decision algorithm was sensitive to some measurements which may have had a considerable margin of error.

5.5.4 Group Classification

Each bag measurement at LAX was first categorized into one of ten groups based on grams of nitrogen content and volume. The purpose of this categorization was to separate the bags into groups of different nitrogen density ranges so that it would be easier to discriminate high nitrogen density bags from the low ones.

The performance of the CF-LAX decision algorithm by group is shown in Table 5.10

TABLE 5.10

GROUP DEFINITIONS FOR CF-LAX

1) Nit : 0 - 250.0 grams
   Vol : 0 - 99999.0 cu in

2) Nit : 250 - 500.0 grams
   Vol : 0 - 3000.0 cu in

3) Nit : 250 - 500.0 grams
   Vol : 3000 - 5000.0 cu in

4) Nit : 250 - 500.0 grams
   Vol : 5000 - 6000.0 cu in

5) Nit : 250 - 500.0 grams
   Vol : 6000 - 7000.0 cu in

6) Nit : 500 - 700.0 grams
   Vol : 0 - 5000.0 cu in

7) Nit : 500 - 700.0 grams
   Vol : 5000 - 7000.0 cu in

8) Nit : 500 - 700.0 grams
   Vol : 7000 - 99999.0 cu in

9) Nit : 700 - 99999.0 grams
   Vol : 0 - 7000.0 cu in

10) Nit : 700 - 99999.0 grams
    Vol : 7000 - 99999.0 cu in

As expected, both false alarm and detection rates are high for high nitrogen, low volume groups (2,6,9), because it is difficult to differentiate between simulant and background nitrogen for high nitrogen density bags.

5.5.5 LAX Discriminant Algorithm

After the bag data is categorized into one of several nitrogen density groups, the discriminant analysis is applied to a set of features extracted from each bag. The discriminant model used in CF-LAX is very similar to the one used in SFIA-TWA. It is a 3-way discriminant model with a different separation function for each nitrogen density group. The only difference is that the CF-LAX model uses more features (i.e., 15 in CF-LAX vs. 10 in SFIA-TWA) in the discriminant algorithm. See Appendix E, Tables 3 and 4, for more details on the features selected and for the sample coefficients.

What is claimed is:

1. An explosive detection system comprising:
   (a) a source of neutrons;
   (b) a detector array comprising a plurality of gamma ray detectors, each of said gamma ray detectors providing a detection signal in the event a gamma ray is captured by said detector, and at least one neutron detector, said neutron detector providing a neutron detection signal in the event a neutron is captured by said neutron detector;
   (c) means for irradiating an object being examined with neutrons from the neutron source and for positioning the detector array relative to the object so that gamma rays emitted from the elements within the object as a result of said neutron irradiation are detected by the gamma ray detectors of said detector array; and
   (d) parallel distributed processing means responsive to the detection signals of said detector array for discriminating between objects carrying explosives and objects not carrying explosives, said parallel distributed processing means including an artificial neural system (ANS), said ANS having a parallel network of processors, each processor of said parallel network of processors including means for receiving at least one input signal, and means for generating an output signal as a function of said at least one input signal.

2. The explosive detection system as set forth in claim 1 further including spectral correlation means for removing noise from the gamma ray detection signals generated by said gamma ray detectors, whereby only gamma rays having a selected energy level are accepted by said parallel distributed processing means.

3. The explosive detection system as set forth in claim 1 further including X-ray means for generating an electron density image of said object, said means for utilizing said electron density image in combination with the detection signals from said detector array to discriminate between objects carrying explosives and objects not carrying explosives.

4. The explosive detection system as set forth in claims 1, 2, or 3 wherein said parallel network of processors includes a plurality of layers of said processors, a first layer of said processors receiving as an input signal a detection signal from one of said plurality of detectors, a last layer of said processors providing a plurality of output signals that classify said objects as objects carrying explosives and objects not carrying explosives.

5. The explosive detection system as set forth in claim 4, further including means for applying an adjustable weighting factor to the at least one input signal of each processor, whereby the output signals that classify said objects can be adjusted to properly classify said objects through adjustment of said weighting factors.

6. The explosive detection system as set forth in claims 1, 2 or 3 wherein said parallel network of processors includes a plurality of layers of said processors, a first layer of said processors receiving as an input signal a feature signal derived from a selected combination of said detector signals, a last layer of said processors providing a plurality of output signals that classify said objects as objects carrying explosives and objects not carrying explosives.

7. The explosive detection system as set forth in claim 6 further including means for applying an adjustable weighting factor to the at least one input signal of each processor, whereby the output signals that classify said objects can be adjusted to properly classify said objects through adjustment of said weighting factors.

8. An explosive detection system comprising:
   (a) a source of neutrons;
   (b) at least one detector array comprising a plurality of gamma ray detectors, each of said detectors providing a detection signal in the event a gamma ray is captured by said detector;
   (d) a neutron detector;
   (c) means for bombarding an object being examined with neutrons from the neutron source and for positioning the detector array relative to the object so that gamma rays emitted from the elements within the object as a result of said neutron bombardment are detected by the gamma ray detectors of said detector array; and
   (d) parallel distributed processing means responsive to the detection signals of said detector array and neutron detector for discriminating between objects carrying explosives and objects not carrying explosives, said parallel distributed processing means comprising a parallel network of processors, each processor of said parallel network of processors including means for receiving at least one input signal, and means for generating an output signal as a function of said at least one input signal, said parallel network of processors including a plurality of layers of said processors, a first layer of said processors receiving as an input signal a feature signal derived from a selected combination of said detection signals, a last layer of said processors providing a plurality of output signals that classify said objects as either objects having a high probability of carrying explosives or objects having a high probability of not carrying explosives.

9. Apparatus for non-invasively detecting explosives in an object under investigation comprising:
   means for generating thermal neutrons;
   means for irradiating said object with said thermal neutrons, the interactions of said thermal neutrons with atomic nuclei within said object giving rise to the emission of gamma rays, said gamma rays having an energy level characteristic of the nuclear species contained in said object;
   gamma ray detection means for detecting emitted gamma rays having an energy level characteristic of at least one element and for roughly determining the location within said object from which the detected gamma rays originated, the detection of said gamma rays and their source location thereby providing a measure of the density distribution of said at least one element within said object;
   neutron detection means for detecting neutrons that pass through said object without interacting with atomic nuclei, the detection of said neutrons thereby providing a measure of the density distribution of all materials within said object, including said at least one element;
   image means responsive to said gamma ray and neutron detection means for generating a three-dimensional density image of said at least one element within said object; and
   an artificial neural system, said artificial neural system including recognition means responsive to said gamma ray and neutron detection means for recognizing a pattern of detected gamma rays and neutrons indicative of an explosive.

10. Explosive detection apparatus as set forth in claim 9 further including:
means for generating at least one two-dimensional electron density image of said object; and
means for combining said at least one element density image and said electron density image and for determining whether said combined image indicates the presence of explosives within said object.

11. Explosive detection apparatus as set forth in claim 10 wherein said electron density image generation means includes means for generating two two-dimensional electron density images of said object, a first electron density image lying in a first plane, and a second electron density image lying in a second plane that is orthogonal to said first plane.

12. Explosive detection apparatus as set forth in claim 9 wherein said recognition means of said artificial neural system includes means for automatically adjusting the patterns it recognizes as belonging to explosives based on detected patterns of gamma rays and neutrons from objects containing known explosives.

13. Explosive detection apparatus as set forth in claim 9 or 10 wherein said gamma ray detection means includes means for rejecting background noise in the detected gamma rays, said background noise including the detection of gamma rays emitted from non-explosive elements.

14. Explosive detection means as set forth in claim 13 wherein said means for rejecting background noise includes spectral correlation means for measuring background noise at a first location in the detected gamma ray spectrum and subtracting said background noise from a second location in the gamma ray spectrum, said second location in the gamma ray spectrum corresponding to gamma rays resulting from neutron interaction with nitrogen nuclei.

15. Apparatus for non-invasively detecting explosives in an object under investigation comprising:
means for generating thermal neutrons;
means for irradiating said object with said thermal neutrons, the interactions of said thermal neutrons with atomic nuclei within said object giving rise to the emission of gamma rays, said gamma rays having an energy level characteristic of the nuclear species contained in said object;
gamma ray detection means for detecting emitted gamma rays having an energy level characteristic of at least one specific element and for roughly determining the location within said object from which the detected gamma rays originated, the detection of said gamma rays and their source location thereby providing a measure of the density distribution of said at least one specific element within said object;
neutron detection means for detecting neutrons that pass through said object without interacting with atomic nuclei, the detection of said neutrons thereby providing a measure of the density distribution of all materials within said object, including said at least one element;
X-ray means for generating at least one two-dimensional electron density image of said object; and
determining means for combining said measure of the density distribution of all materials within said object, including said at least one specific element, with said electron density image, and for determining whether said combined measure and image indicate the presence of explosives within said object, said determining means including an artificial neural system, said artificial neural system having recognition means responsive to said gamma ray and neutron detection means for recognizing a pattern of detected gamma rays and neutrons indicative of an explosive.

16. Explosive detection apparatus as set forth in claim 15 wherein said electron density image generation means includes means for generating two two-dimensional electron density images of said object, a first electron density image lying in a first plane, and a second electron density image lying in a second plane that is orthogonal to said first plane.

17. Explosive detection apparatus as set forth in claim 15 wherein said recognition means of said artificial neural system includes means for automatically adjusting the patterns it recognizes as belonging to explosives based on detected patterns of gamma rays from objects containing known explosives.

18. Explosive detection apparatus as set forth in claim 15 wherein said artificial neural system is further responsive to the electron density images obtained from said X-ray means.

19. Explosive detection apparatus as set forth in claim 15 wherein said gamma ray detection means includes means for rejecting background noise in the detected gamma rays, said background noise including the detection of gamma rays emitted from non-explosive elements.

20. Explosive detection apparatus as set forth in claim 19 further including neutron detection means for detecting neutrons that pass through said object without interacting with atomic nuclei, the detection of said neutrons thereby providing a measure of the density distribution of all materials within said object, including nitrogen, hydrogen, and chlorine.

21. Apparatus for non-invasively detecting explosives in an object under investigation comprising:
means for generating thermal neutrons;
means for irradiating said object with said thermal neutrons, the interactions of said thermal neutrons with atomic nuclei within said object giving rise to the emission of gamma rays, said gamma rays having an energy level characteristic of the nuclear species contained in said object;
gamma ray detection means for detecting emitted gamma rays having an energy level characteristic of at least one specific element and for roughly determining the location within said object from which the detected gamma rays originated, the detection of said gamma rays and their source location thereby providing a measure of the density distribution of said at least one specific element within said object;
neutron detection means for detecting neutrons that pass through said object without interacting with atomic nuclei, the detection of said neutrons thereby providing a measure of the density distribution of all materials within said object, including said at least one element;
an artificial neural system, said artificial neural system including recognition means responsive to said gamma ray detection means for recognizing a pattern of detected gamma rays and neutrons indicative of an explosive, said recognition means including means for automatically adjusting the patterns it recognizes as belonging to explosives based on detected patterns of gamma rays and neutrons from objects containing known explosives;

image means responsive to said gamma ray detection means for generating a three-dimensional density image of said at least one specific element within said object;

determining means responsive to said artificial neural system and said image means for determining whether said three-dimensional density image of said at least one specific element density image indicates the presence of explosives within said object.

22. Explosive detection apparatus as set forth in claim 21 wherein said gamma ray detection means includes means for rejecting background noise in the detected gamma rays, said background noise including the detection of gamma rays emitted from non-explosive elements.

23. Explosive detection means as set forth in claim 22 wherein said means for rejecting background noise includes spectral correlation means for measuring background noise at a first location in the detected gamma ray spectrum and subtracting said background noise from a second location in the gamma ray spectrum, said second location in the gamma ray spectrum corresponding to gamma rays resulting from neutron interaction with nuclei.

24. Apparatus for non-invasively detecting explosives in an object under investigation comprising:

means for generating thermal neutrons;

means for irradiating said object with said thermal neutrons, the interactions of said thermal neutrons with atomic nuclei within said object giving rise to the emission of gamma rays, said gamma rays having an energy level characteristic of the nuclear species contained in said object;

gamma ray detection means for detecting emitted gamma rays having an energy level characteristic of at least one specific element and for roughly determining the location within said object from which the detected gamma rays originated, said gamma ray detection means including means for rejecting background noise in the detected gamma rays, said background noise including the detection of gamma rays emitted from non-explosive elements, the detection of said gamma rays and their source location thereby providing a measure of the density distribution of said at least one specific element within said object;

neutron detection means for detecting neutrons that pass through said object without interacting with atomic nuclei, the detection of said neutrons thereby providing a measure of the density distribution of all materials within said object, including said at least one element;

determining means responsive to said measure of the density distribution of the materials, including said at least one specific element, within said object for determining whether said object likely contains an explosive, said determining means including an artificial neural system.

25. Explosive detection means as set forth in claim 24 wherein said means for rejecting background noise within said gamma ray detection means includes spectral correlation means for measuring background noise at a first location in the detected gamma ray spectrum and subtracting said background noise from a second location in the gamma ray spectrum, said second location in the gamma ray spectrum corresponding to gamma rays resulting from neutron interaction with nuclei.

* * * * *

UNITED STATES PATENT AND TRADEMARK OFFICE
CERTIFICATE OF CORRECTION

PATENT NO. : 5,078,952　　　　　　　　　　　　　　Page 1 of 2

DATED : January 7, 1992

INVENTOR(S) : Gozani, et al.

It is certified that error appears in the above-identified patent and that said Letters Patent is hereby corrected as shown below:

Title page, Abstract: Line 31, change "a" to --an--. IN THE
　　　　　Column 3, line 9, change "type" to --types--.
Column 4, line 25, change "Mev" to --MeV--. Column 4, line 34, change "applicant's" to --applicants'--. Column 8, line 58, change "form" to --from--. Column 9, line 4, change "verses" to --versus--. Column 9, line 18, after "source" insert--.--. Column 10, line 13, change "thorough" to --through--. Column 10, line 40, change "detective" to --detector--. Column 11, line 18, after "(BaF$_2$)" insert --.--. Column 11, lines 59, 62, 64, 65, change "germinate" to --germanate--. Column 14, line 47, change "Mev" to --MeV--. Column 14, line 49, change "as" to --an--. Column 15, line 45, change "the" to --The--. Column 19, line 5, change "subset" to --subsets--. Column 20, line 18, change "of" to --on--. Column 20, line 24, change "an" to --a--. Column 20, line 31, change "it" to --if--. Column 20, line 68, change "th" to --the--. Column 21, line 19, change "these" to --those--. Column 22, line 17, change "ca" to --can--. Column 23, line 19, change "applicants'prior" to --applicants' prior--. Column 23, line 25, change "a" to --an--. Column 23, line 40, delete "of".
In Claim 3, column 185, line 37, change "said" to --and--.
In Claim 8, column 186, lines 10, 18 change "(d)" to --(c)--.
In Claim 8, column 186, line 11, change "(c)" to --(d)--.

UNITED STATES PATENT AND TRADEMARK OFFICE
CERTIFICATE OF CORRECTION

PATENT NO. : 5,078,952

DATED : January 7, 1992

INVENTOR(S) : Gozani, et al

It is certified that error appears in the above-identified patent and that said Letters Patent is hereby corrected as shown below:

Claim 13, Column 187, line 23, change "claim" to --claims--.

Signed and Sealed this

Tenth Day of August, 1993

Attest:

MICHAEL K. KIRK

Attesting Officer

Acting Commissioner of Patents and Trademarks